(12) United States Patent
Marino

(10) Patent No.: US 9,514,493 B2
(45) Date of Patent: *Dec. 6, 2016

(54) SYSTEM OF SYSTEMS FOR MONITORING GREENHOUSE GAS FLUXES

(71) Applicant: Planetary Emissions Management, Inc., Cambridge, MA (US)

(72) Inventor: Bruno D. V. Marino, Brunswick, ME (US)

(73) Assignee: PLANETARY EMISSIONS MANAGEMENT, INC., Cambridge, MA (US)

( * ) Notice: Subject to any disclaimer, the term of this patent is extended or adjusted under 35 U.S.C. 154(b) by 562 days.

This patent is subject to a terminal disclaimer.

(21) Appl. No.: 14/040,206

(22) Filed: Sep. 27, 2013

(65) Prior Publication Data

US 2014/0172323 A1    Jun. 19, 2014

Related U.S. Application Data

(63) Continuation of application No. 12/698,460, filed on Feb. 2, 2010, now Pat. No. 8,595,020.

(60) Provisional application No. 61/149,122, filed on Feb. 2, 2009.

(51) Int. Cl.
*G06Q 10/00* (2012.01)
*C01B 31/14* (2006.01)
(Continued)

(52) U.S. Cl.
CPC .............. *G06Q 50/00* (2013.01); *G01N 21/00* (2013.01); *G01N 21/3504* (2013.01);
(Continued)

(58) Field of Classification Search
CPC .............. G01B 21/00; G01B 33/0004; G01B 21/3504; G01B 21/39; G06Q 50/00; G06Q 40/04; G06Q 10/30; G06Q 30/018

See application file for complete search history.

(56) References Cited

U.S. PATENT DOCUMENTS 5,317,156 A    5/1994  Cooper et al.
5,394,236 A    2/1995  Murnick
(Continued)

FOREIGN PATENT DOCUMENTS

JP    3238109 A     10/1991
JP    04-027854 B2   1/1992
(Continued)

OTHER PUBLICATIONS

Japanese Office Action issued by the Japan Patent Office for Application No. 2014-149944 dated Jun. 16, 2015 (5 pages).
(Continued)

*Primary Examiner* — Matthew G Marini
*Assistant Examiner* — Leo T Hinze
(74) *Attorney, Agent, or Firm* — Wilmer Cutler Pickering Hale and Dorr LLP

(57) ABSTRACT

A system of systems to monitor data for carbon flux, for example, at scales capable of managing regional net carbon flux and pricing carbon financial instruments is disclosed. The system of systems can monitor carbon flux in forests, soils, agricultural areas, body of waters, flue gases, and the like. The system includes a means to identify and quantify sources of carbon based on simultaneous measurement of isotopologues of carbon dioxide, for example, industrial, agricultural or natural sources, offering integration of same in time and space. Carbon standards are employed at multiple scales to ensure harmonization of data and carbon financial instruments.

25 Claims, 33 Drawing Sheets

(51) Int. Cl.
| | |
|---|---|
| G06Q 50/00 | (2012.01) |
| G01N 21/3504 | (2014.01) |
| G06Q 30/00 | (2012.01) |
| G01N 21/00 | (2006.01) |
| G01N 33/00 | (2006.01) |
| G06Q 40/04 | (2012.01) |
| G01N 21/39 | (2006.01) |

(52) U.S. Cl.
CPC ......... *G01N 33/0004* (2013.01); *G06Q 10/30* (2013.01); *G06Q 30/018* (2013.01); *G06Q 40/04* (2013.01); *G01N 21/39* (2013.01); *Y02P 60/30* (2015.11); *Y02W 90/20* (2015.05)

(56) References Cited

U.S. PATENT DOCUMENTS

| | | | |
|---|---|---|---|
| 5,747,809 | A | 5/1998 | Eckstrom |
| 5,783,445 | A | 7/1998 | Murnick |
| 5,818,580 | A | 10/1998 | Murnick |
| 5,864,398 | A | 1/1999 | Murnick |
| 6,164,129 | A | 12/2000 | Shin et al. |
| 7,154,595 | B2 | 12/2006 | Paldus et al. |
| 7,426,489 | B2 | 9/2008 | van Soestbergen et al. |
| 7,616,305 | B2 | 11/2009 | Murnick |
| 8,595,020 | B2 | 11/2013 | Marino |
| 2007/0224085 | A1 | 9/2007 | Tooley |
| 2007/0250329 | A1 | 10/2007 | Richards et al. |
| 2008/0015975 | A1 | 1/2008 | Ivchenko et al. |
| 2008/0015976 | A1 | 1/2008 | Sandor et al. |
| 2008/0059206 | A1 | 3/2008 | Jenkins |
| 2008/0221750 | A1 | 9/2008 | Baraty |
| 2008/0228628 | A1 | 9/2008 | Gotthelf et al. |
| 2008/0228630 | A1 | 9/2008 | Gotthelf et al. |
| 2008/0228632 | A1 | 9/2008 | Gotthelf et al. |
| 2008/0228665 | A1 | 9/2008 | Gotthelf et al. |
| 2009/0273781 | A1 | 11/2009 | Clegg et al. |
| 2010/0198736 | A1* | 8/2010 | Marino ............... G01N 21/3504 705/308 |

FOREIGN PATENT DOCUMENTS

| | | |
|---|---|---|
| JP | 11-094737 A | 4/1999 |
| JP | 2000-505558 A | 5/2000 |
| JP | 2002-286638 A | 10/2002 |
| JP | H07-020054 A | 1/2007 |
| WO | WO-99/42814 A1 | 8/1999 |

OTHER PUBLICATIONS

Murnick, D. E. and Okil, J. O., "Use of the optogalvanic effect (OGE) for isotope ratio spectrometry of $^{13}CO_2$ and $^{14}CO_2$," Isotopes in Environmental and Health Studies, vol. 41, No. 4 pp. 363-371 (Dec. 2005).

Adler, Ben. Apr. 26, 2010. Senate Energy Bill Could Halt California's Emission Reduction Efforts. http://capradio.org/articles/2010/04/26/senate-energy-bill-could-halt-california's-emission-reduction-efforts. 3 pages.

Air Resources Board, State of California. ARB 2009 http://www.arb.ca.gov/cc/factsheets/ab32factsheet.pdf, 2 pages (2009).

Allison C.E., Francey R.J., White J.W.C, Vaughn B.H., Wahlen M., Bollenbacher A., Nakazawa T. What have we learnt about stable isotope measurements from the IAEA Classic? In: Report of the eleventh WMO/IAEA meeting of experts on carbon dioxide concentration and related tracer measurement techniques, Tokyo, Japan, Sep. 25-28, 2001, MO/GAW Report No. 148, Geneva, pp. 17-30 (2003).

Allison, C.E., Francey R.J., and Steele, L.P. The International Atomic Energy Agency circulation of laboratory air standards for stable isotope comparisons: aims, preparation and preliminary results. In: Isotope aided studies of atmospheric carbon dioxide and other greenhouse gases Phase II (IAEA-TEDOC-1269). IAEA, Vienna, Austria, pp. 5-23 (2002).

Amico di Meane, E., Plassa, M., Rolle, F., Sega, M. Metrological traceability in gas analysis at I.N.Ri.M: gravimetric primary gas mixtures. Accred Qual Assur 14:607-611 (2009).

Amundson, R., Sanderman, J., and Yoo, K. Environmental and geological controls on the soil carbon cycle in a changing world (in Geological Society of America, 2008 annual meeting, Anonymous,) *Abstracts with Programs—Geological Society of America* (October, vol. 40(6):24 (2008).

ASTM D6866-08. Active Standard: D6866-08. Standard Test Methods for Determining the Biobased Content of Solid, Liquid, and Gaseous Samples Using Radiocarbon Analysis. ASTM, 2 pages (2008).

Barford, C., Steven C. Wofsy, Michael L. Goulden, J. William Munger, Elizabeth Hammond Pyle, Shawn P. Urbanski, Lucy Hutyra, Scott R. Saleska, David Fitzjarrald, and Kathleen Moore. *Science* 294: 1688-1691 DOI: 10.1126/science.1062962, 4 pages (2001).

Becker, J.F., Sauke, T.B., Loewenstein, M. Appl. Opt. 31: 1921, 7 pages (1992).

Bonan, G. B. A land surface model (LSM version 1.0) for ecological, hydrological, and atmospheric studies: Technical description and user's guide, 150 pp., Natl. Cent. for Atmos. Res., Boulder, Colo., 156 pages (1996).

Bradley, L.C., Soohoo, K.L., Freed, C. Absolute frequencies of lasing transitions in nine CO2 isotopic species. IEEE Journal of Quantum Electronics vol. QE-22, No. 2, 34 pages (1986).

Broecker, W. Radiocarbon. In: Treatise on Geochemistry, Elsevier, 18 pages, 2007.

Brown, M.A., Levine' M.D., Short, W., Koomey. J.G., Energy Policy 29(14): 1179-1196 (2001).

Canadell, J., Quere C., Raupach M., Field C., Buitenhuis E., Ciais P., Conway T., Gillett N., Houghton R., Marland G. Contributions to accelerating atmospheric CO2 growth from economic activity, carbon intensity and efficiency of natural sinks. PNAS early edition, 10.1073, 5 pages (2007).

Capoor, K., and Ambrosi. 2007. State and Trends of the Carbon Market 2007. World Institute, Washington, DC, 2007, 52 pages.

Chicago Climate Exchange 2010. http://www.chicagoclimatex.com/content.isf?id=781. 2 pages.

Ciais P., and four others. A Large northern hemisphere terrestrial CO2 sink indicated by the 13C/12C ratio of atmospheric CO2. Science 269(5227): 1098-1102 (1995).

Convery' F.J. and Redmond, L. Market and Price Developments in the European Union Emissions Trading Scheme. *Rev Environ Econ Policy* 1: 88-111 (2007).

Coplen T.B. et al., and five others. New Guidelines for delta $^{13}C$ measurements. Anal. Chem. 78: 2439-2441 (2006).

Coplen, T.B. New manuscript guidelines for the reporting of stable hydrogen, carbon, and oxygen isotope-ratio data. *Geothermics* 24(5-6):707-712 (1995).

Davis, W. Carbon-14 production in nuclear reactors. ORNL/NUREG/TM-12, 42 pages (1977).

Dias, C.M. and 4 others. 14C content in vegetation in the vicinities of Brazilian nuclear power reactors. J. Env. Radio. 99(7): 1095-1101 (2008).

Diaz, David. Mar. 3, 2010. "California Moves Carbon Offset Goalposts." http://www.forestcarbonportal.com/content/california-moves-carbon-offset-goalposts. Page 3.

Ellerman, D.A. and Joskow, P.L. The European Union's Emissions Trading System in Perspective. MIT, 64 pages, May 2008.

European Search Report for European Patent Application No. 10736564.5 mailed Nov. 25, 2013. 9 pages.

European Union Emissions Trading Scheme. www.euets.com. 45 pages 2009.

Flesch, T.K., Wilson, J.D., Harper, L.A., Crenna, B.P., Sharpe, R.R. Deducing ground-to-air emissions from observed trace gas concentrations: a field trial. J. Appl. Meteorol. 43, 487-502 (2004).

Fluxnet. http://www.fluxnet.ornl.gov/fluxnet/index.cfm., 1 page, retrieved Jun. 14, 2012.

Freed C. CO2 Isotope Lasers and their applications in tunable laser spectroscopy. Chapter 4, pp. 63-165 in "Tunable Lasers Handbook", 103 pages (Academic Press, 1995, F.J. Duarte, Editor).

(56) References Cited

OTHER PUBLICATIONS

Freed, C. Ultrastable CO2 Lasers. The Lincoln Laboratory Journal. vol. 3(3): 479-500 (1990).

Friedmann, S.J, Geological Carbon Dioxide Sequestration Elements vol. 3, pp. 179-184, (2007).

Galik, S.C., Mobley, M.L., Richter, D. A virtual "field test" of forest management carbon offset protocols: in influence of accounting. Mitig. Adapt Strage Glob Change 14:677-690 (2009).

Gitzinger C. and 3 others. Technical Report: Verifications under the terms of article 35 of the euratom treaty. Finnish National Monitoring Network for Environmental Radioactivity. FI—Jul. 2002, 45 pages (2007).

Global view. NOAA. http://www.esrl.noaa.gov/gmd/ccgg/globalview/, 1 page (2010).

Granier, A. et al. "The Carbon Balance of a Young Beech Forest." Functional Ecology. No Month Listed. 200, 14, pp. 312-325. 14 pages.

Graven, H.D. and 5 others. Vertical profiles of biospheric and fossil fuel-derived CO2 and fossil fuel CO2: CO ratios from airborne measurements of delta 14C, CO2 and CO above Colorado, USA. Tellus 61B, 536-546 (2009).

Grell, G., Dudhia, J., and Stauffer, D. A description of the fifth-generation Penn State/NCAR mesoscale model (MM5), Natl. Cent. for Atmos. Res., Boulder, Colo., 1 page (1995).

Guillian, E.H. Far field monitoring of rogue nuclear activity with an array of large anti-neutrino detectors. Earth, Moon, and Planets 99: 309-330 (2006).

Gulden, M.L., et al., and 4 others. Measurements of carbon sequestration by long-term eddy covariance: methods and a critical evaluation of accuracy. Global Change Biology 2: 169-182 (1996).

Ha-Duong, M., and Loisel R. Zero is the only acceptable leakage rate for geologically stored CO2: an editorial comment Climatic Change 93:311-317 (2009).

Hamilton, K., Sjardin, M., Marcello, M., and Xu, G. Forging a Frontier: State of the Voluntary Carbon Markets 2008. A report by Ecosystem Marketplace & New Carbon Finance, May 2008, 78 pages.

Heimann, M. and Maier-Reimer, E. On the relations between the oceanic uptake of carbon dioxide and its carbon isotopes. Global Biogeochemical Cycles, 10: 89-110 (1996).

Hsueh, D.Y., and 6 others. Regional patterns of radiocarbon and fossil fuel-derived CO2 in surface air across North America. Geophys. Res. Lttrs. vol. 34, L02816, doi:10.1029/2006GL027032 (2007).

Humphries, S.D., A. R. Nehrir, C. J. Keith, K. S. Repasky, L. M. Dobeck, J. L. Carlsten, and L. H. Spangler, "Testing carbon sequestration site monitor instruments using a controlled carbon dioxide release facility," Appl. Opt. 47, 548-555 (2008).

Hurley, P.J., Physick, W.L., Luhar, A.K. TAPM: a practical approach to prognostic meteorological and air pollution modeling. Environ. Model. Software 20, 737-752 (2005).

Hämäläinen, K M; Jungner, H; Antson, O; Räsänen, J; Tormonen, K; Roine, J. Penn State/NCAR mesoscale model (MM5), Natl. Cent. for Atmos. Res., Boulder, Measurement of Biocarbon in Flue Gases Using 14C Radiocarbon, vol. 49(2): 325-330 (2007).

International Search Report and Written Opinion for International Application No. PCT/US2010/022864 mailed Jul. 29, 2010, 8 pages.

IPCC. Climate Change 2007 and 2008—The Physical Science Basis, 22 pages (2008).

IPCC. Contribution of Working Group I to the Fourth Assessment Report of the IPCC (ISBN 978 0521 88009-1), 22 pages (2007).

Kallman, C.T. Detection technology in the $21^{st}$ century: the case of nuclear weapons of mass destruction. US Army War College, Carlisle, PA, 36 pages (2008).

Keeling, C. D. The Suess effect: 13Carbon-14Carbon interrelations. Environment International vol. 2: 229-300 (1979).

Keeling, C.D. The concentration and isotopic abundances of atmospheric carbon dioxide in rural areas. *Geochem. et Cosmochem. Acta* 13 (322-334) (1958).

Korashi, J. and 4 others. A simple and reliable monitoring system for 3H and 14C in radioactive airborne effluent. J. Radio. Nuc. Chem. 268(3): 475-479 (2006).

Kosovic, B. Monache, L.D., Cameron-Smith, P., Bergman, D., Grant, K., Guilderson, T. Toward regional fossil fuel CO2 emissions verification using WRF-CHEM. $9^{th}$ WRF users workshop, Boulder, CO. Jun. 26, 2008, 17 pages.

Lai, C.T., Schauer, A.J., Owensby, C., Ham, J.M., Helliker, B., Tans, P.P., Ehleringer, J.R. Regional CO2 fluxes inferred from mixing ratio measurements: estimates from flask air samples in central Kansas, USA. Tellus vol. 58b, pp. 523-536 (2006).

Leuning, R., Etheridge, D., Luhar, A., Dunse, B. Atmospheric monitoring and verification technologies for $CO_2$ geosequestration. Intl J. Greenhouse Gas Controls 2: 401-414 (2008).

Levin, I., Kormer, B., Schmidt, M., Sartorius, H., A novel approach for independent budgeting of fossil fuel CO2 over Europe by 14CO2 observations. Geo. Res. Letters vol. 30 (23), 2194, 5 pages (2003).

Levin, I., J. Schuchard, B. Kormer, K.O. Munnich. The continental European Sues effect. *Radiocarbon* 31:431-440 (1989).

Levin, I., R.. Graul, N.B.A. Trivett. Long term observations of atmospheric CO2 and carbon isotopes at continental sites in Germany. *Tellus* 47B:23-34 (1995).

Levin, I., Rodenbeck, C. Can the envisaged reductions of fossil fuel CO2 emissions be detected by atmospheric observations? Naturwissenschaften 95: 203-208 (2008).

Lewicki, J. L., G.E. Hilley, M.L. Fischer, L. Pan, C.M. Oldenburg, L. Dobeck, and L. Spangler, Eddy covariance observations of surface leakage during shallow subsurface CO2 releases, Journal of Geophysical Research—Atmospheres, 114, D12302, 13 pages (2009).

Libby W. F., Anderson E. C., and Arnold J. R. Age determination by radiocarbon content: worldwide assay of natural radiocarbon. Science 109, 227-228 (1949).

Lloyd, J. and 12 others. Vertical profiles, boundary layers, and regional flux estimates for CO2 and its 13C/12C ratio for water vapor above a forest/bog mosaic in central Siberia. Global Biogeochemical Cycles, 15(2): 267-284 (2001).

Matsumoto, K., and 30 others. Evaluation of ocean carbon cycle models with data-based metrics. Geophys. Res. Lett. 31, L07303, doi: 10.1029/2003GL018970, 4 pages (2003).

McNichol, A.P. and 3 others. The rapid preparation of seawater total CO2 for radiocarbon analysis at the national ocean sciences AMS facility. Radiocarbon 36(2): 237-246 (1994).

Midwest Greenhouse Gas Accord. www.midwesternaccord.org., 4 pages 2009.

Murnick, D.E., Dogru, O., and Ilkmen, E. Intracavity optogalvanic spectroscopy: An analytical technique for14C analysis with subattamole sensitivity. Analytical chemistry 80(13):4820-4824 (2008).

Murnick, D. E., Dogru, O, Ilkman, E. Laser based $^{14}C$ counting, an alternative to AMS in biological studies. Nuclear Instruments and Methods in Physics Research Section B: Beam Interactions with Materials and Atoms vol. 259(1): 786-789 (2009).

Murnick, D., Dogru, O., Ilkmen E. Nuclear Instruments and Methods in Physics Research B 259 786-789 (2007).

Murnick, D.E., and Peer, J. Science 263: 945-947 (1994).

O'Leary, M. H. Carbon isotopes in photosynthesis. BioScience, 38, 328-336 (1988).

Oldenburg, C.M., Lewicki, L.L., and Hepple, R.P. Near-surface monitoring strategies for geologic carbon dioxide storage verification. Earth Science Division, Ernesto Orlando LBNL, ReportLBNL-54089, pp. 1-54 (2003).

Pacala S. W. Letter Reporting on the Orbiting Carbon Observatory. Committee on Methods for Estimating Greenhouse Gas Emissions; National Research Council, 9 pages (2009).

Park, J.H. and 6 others. Isotopic fractionation during pretreatment for accelerator mass spectrometer measurement of (D3C)2O containing 14C produced bhy nuclear reaction. J. Radio. Nuc. Chem. 275(3): 627-631 (2008).

Parton, W., and 10 others. Observations and modeling of biomass and soil organic matter dynamics for the grassland biome worldwide. Glob. Biogeochem. Cycles 7:109-131 (1993).

(56) References Cited

OTHER PUBLICATIONS

Peters, W. and 15 others. An atmospheric perspective on North American carbon dioxide exchange: Carbon Tracker. Proc. Natl. Acad. Sci. USA, 48, 18925-18930 (2007).
Randerson J.T., and 4 others. Seasonal and latitudinal variability of troposphere delta 14CO2: Post bomb Contributions from fossil fuels, oceans, the stratosphere, and the terrestrial biosphere. Global Biogeochemical Cycles, vol. 16(4): 1112, 19 pages (2002).
Raupach, M., Marland G., Ciais P., Quere C., Canadell J., Klepper G., Field C. Global and regional drivers of accelerating CO2 emissions. PNAS, 104(24):10288-10293 (2007).
Reddy, C.M., Demello, J.A., Carmicheal, C.A., Peacock, E.E., Xu, L. Arey, S.J. Determination of biodiesel blending percentages using natural abundance radiocarbon analysis: testing the accuracy of retail biodiesel blends. Environ. Sci. Technol. 42, pp. 2476-2484 (2008).
Regional Greenhouse Gas Initiative. www.RGGI.og., 1 page 2009.
Riley W. and 7 others. 2008: Where do fossil fuel carbon dioxide emissions from California go? An analysis based on radiocarbon observations and an atmospheric transport model. Journal Geophysical Research. vol. 113, G04002, doi:10.1029/2007JG000625, 16 pages (2007).
Roussel-Debet, S. and 4 others. Distribution of carbon 14 in the terrestrial environment close to French nuclear power plants. J. Env. Radioactivity 87(3): 246-259 (2006).
Rozanski, K. 1991. International Atomic Energy Agency Consultants' Group Meeting on C-14 Reference Materials for Radiocarbon Laboratories, Feb. 18-20, 1991. Report by K. Rozanski, Section of Isotope Hydrology, IAEA, Vienna (1991).
Saleska, S.R., Shorter, J.H., Herndon, S., Jimenez, R., McMannus, J.B., Munger, J.W., Nelson, D.D., Zahniser, M.S. What are the instrumentation requirements for measuring the isotopic composition of net ecosystem exchange of CO2 using eddy covariance methods? Isotopes in Env. Health Studies vol. 42(2), pp. 115-133 (2006).
Salon, D., Sperling D., Meier, A., Murphy, S., Gorham, G., Barrett, J. City carbon budgets: Aligning incentives for climate-friendly communities. Institute of Transportation Studies, University of California, Davis, Research Report UCD-ITS-RR-08-17, 21 pages (2008).
Schlesinger, W.H. Carbon sequestration in soils: some cautions amidst optimism. Agriculture, Ecosystems and Environment vol. 82: (1-3) 121-127 (2000).
Scott, M.E. et al., and 11 others. Future needs and requirements for AMS 14 C standards and reference materials. Nuclear Instruments and Methods in Physics Research B 223-224: 382-387 (2004).
Scott, N.A., and 6 others. Changes in carbon storage and net carbon exchange one year after an initial shelterwood harvest at Howland Forest, ME. Environmental management 33(1): S9-S22, 6 pages (2004).
Staber, S., Flamme S., Fellner J., Methods for determining the biomass content of waste. Waste Management and Research 26: 78-87 (2008).
Steffen W., et al. The Terrestrial Carbon Cycle: Implications for the Kyoto Protocol. Science 280: 1393-1394, 8 pages (1998).
Stork, A., Witte, R., and Fuhr, F. 14CO2 measurement in air: literature review and a new sensitive method. Env. Sci. and Technology 31(4), 7 pages, 1997.
Stuiver, M.,and Polach, H.A. Discussion: Reporting of 14C data. Radiocarbon 19(3):355-363 (1977).
Tans, P.P., P.S. Bakwin, and D.W. Guenther. A feasible global carbon cycle observing system: a plan to decipher today's carbon cycle based on observations. *Global Change Biology* 2:309-318 (1996).

Tuniz, C. Accelerator Mass Spectrometry. Radiation Physics and Chemistry vol. 61(3-6): 317-322 (2001).
Turnbull J.C., and 5 others. Comparison of 14CO2, CO and SF6 as tracers for recently added fossil fuel CO2 in the atmosphere and implications for biological CO2 exchange. Geophysical Research Letters, vol. 33, L01817, 5 pages (2006).
Turnbull, J.C. et al., A new High precision 14CO2 time series for North American continential air. J. Geophysical Research Res. 112, D1130, 10 pages (2007).
Tuzson, B. and 5 others. QCLAS. A compact isotopologue specific analyzer for atmospheric CO2. Geophysical Res. Abstracts 10 (EGU2008-A-07132) 2 pages (2008).
Uchida, M., and 9 others. Ecosystem-scale carbon isotope ratios of respired CO2 in cool-temperate deciduous forests under Asian monsoon climate. Journal of Geophysical Research vol. 113. G02015, 14 pages (2008).
UNFCCC: http://unfccc.int/methods_science/redd/items/4531.php, 2 pages (2008).
Updegraff, K., Zimerman, P.R., Price, M., Capehart, W.J. C-Lock: An online system to standardize the estimation of agricultural carbon sequestration credits. Fuel Processing Technology 86:1695-1704 (2005).
Urbanski, S. and 8 others. Factors controlling CO2 exchange on timescales from hourly to decadal at Harvard Forest. J. Geophys. Res. 112, G02020, doi:10.1029/2006JG000293, 25 pages (2007).
US Climate Change Science Program 2007. Synthesis and Assessment Product 2.2: The First State of the Carbon Cycle Report, 14 pages (2007).
Venteris, E.R. and 8 others. A new digital geologic model for carbon sequestration planning in the Appalachian and Michigan basins. Geological Society of America, Abstracts with programs, vol. 38(4): 14, 2 pages (2006).
Werner, A, Brand, W. Referencing strategies and techniques in stable isotope ratio analysis. Rapid Communications in Mass Spectrometry 15: 501-519 (2001).
West, T.O., and Marland, G. Net carbon flux from agricultural ecosystems: methodology for full carbon cycle analyses. Environ. Pollut. 116(3): 439-44 (2002).
Western Climate Initiative. www.westernclimateinitiative.org. 2009.
Widory, D. Combustibles, fuels and their combustion products: a view through carbon isotopes. Combustion Theory and Modelling vol. 10 (5) pp. 831-841 (2006).
World Meteorological Organization . Global Atmosphere Watch Report, ed. Miller, J.B. (World Meteorological Organization, Geneva), No. 168 (2007).
Yim, M, and Caron, F. Life cycle and management of carbon14 from nuclear power generation. Progress in Nuclear Energy 48: 2-36 (2006).
Zobitz, J.M., and 5 others. Integration of process-based soil respiration models with whole ecosystem CO2 measurements. Ecosystems 11:629-642 (2008).
Zoe, L., and 6 others. Testing Lagrangian atmospheric dispersion modelling to monitor $CO_2$ and $CH_4$ leakage from geosequestration. Atmospheric Environment 43: 2602-2611 (2009).
Zoe" Loh, Ray Leuning, Steve Zegelin, David Etheridge, Mei Bai, Travis Naylor, David Griffith, Masarie, K.A., Langenfelds, R.L., Allison, C.E., Conway, T.J., Dlugokemcky, E.J., Francey, R.J., Novelli, P.C., Steele, L.P., Tans, P.P., Vaughn, B., White, J.W.C. NOAA/CSIRO flask air intercomparison experiment: a strategy for directly assessing consistency among atmospheric measurements made by independent laboratories. J. Geo. Res. vol. 186 (D17), pp. 20445-20464 (2001).
Zwaan B., and Gerlagh R. Effectiveness of CCS with time-dependent CO2 leakage. Energy Procedia 1: 4977-4984 (2009).

* cited by examiner

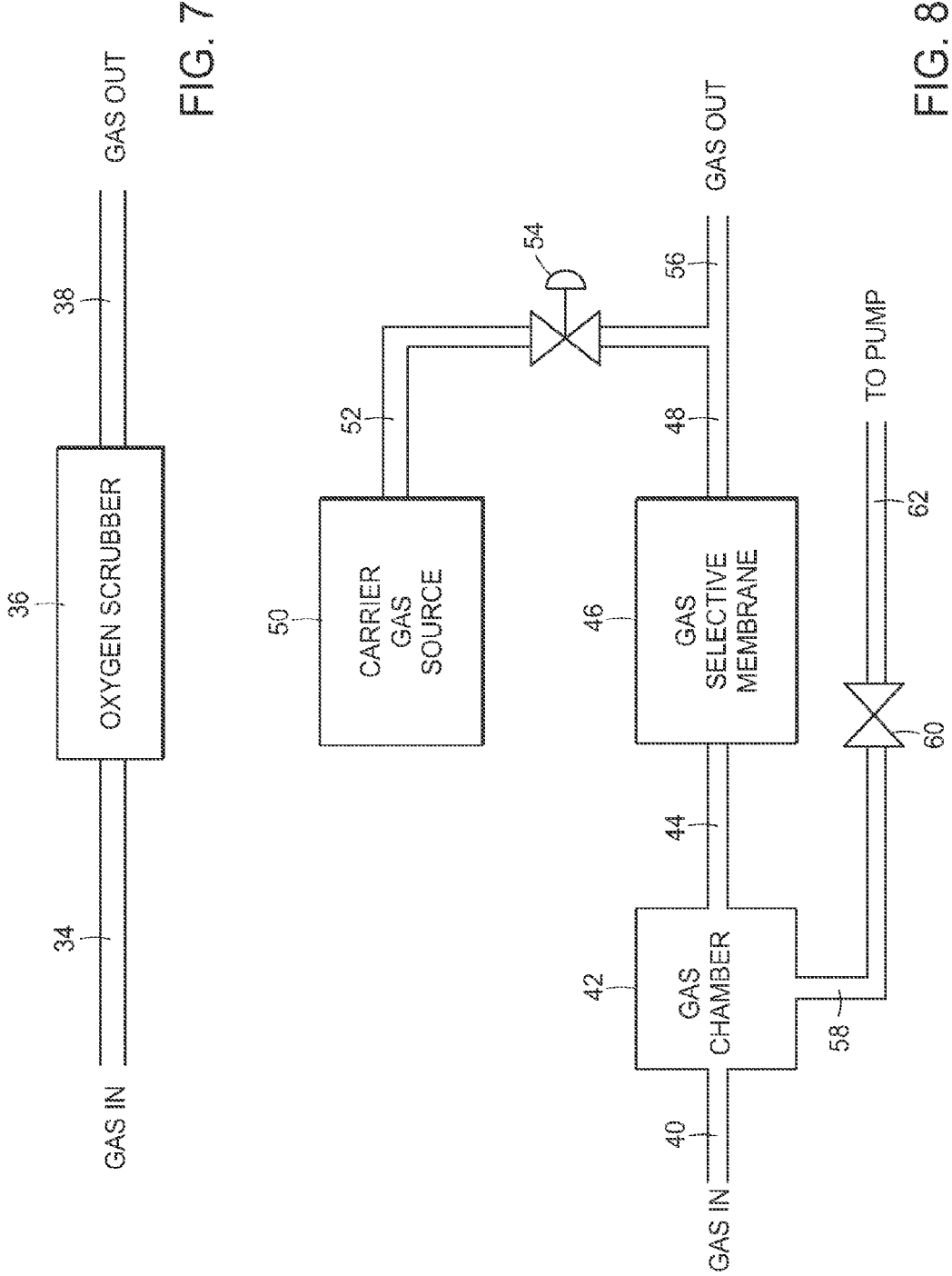

SYSTEM OF SYSTEMS FOR MONITORING GREENHOUSE GAS FLUXES

CROSS REFERENCE TO RELATED APPLICATIONS

The disclosure claims the benefit of the earlier filing date of U.S. Nonprovisional patent application Ser. No. 12/698,460, filed Feb. 2, 2010, now U.S. Pat. No. 8,595,020, issued Nov. 26, 2013, which claims the benefit of U.S. Provisional Patent Application No. 61/149,122, filed on Feb. 2, 2009, the contents of which is incorporated by reference herein in its entirety.

TECHNICAL FIELD

The disclosure relates generally to a geographic-scale standardized system for the measurement, integration, and analysis of data for greenhouse gas sources that can be used to support carbon trading and carbon management policy.

BACKGROUND

The emergence of a market-based trading system for greenhouse gases (GHG) (e.g., IPCC 2007), specifically as embodied in atmospheric $CO_2$, presents a technically more demanding and project specific approach relative to studies of the global carbon cycle (Tans et al., 1996; Steffen et al., 1998). Cost-effective, high precision and carbon specific monitoring underpins not only our understanding of the carbon dynamics of the planet (e.g., full carbon budget) but is also the basis of a new and rapidly emerging carbon economy with discrete geographically defined projects representing partial (local and regional) carbon budgets (Capoor and Ambrosi 2007). An accounting of the carbon burden emitted at local, regional, country-wide and global scales is mirrored in regulatory approaches to reduce, avoid and otherwise diminish current sources as well as show negative carbon results through carbon sequestration.

Specifically, the December 1997 Kyoto Protocol specified emissions target and timetables for industrialized nations and market-based measures for meeting those targets (see Anderson, J. W. 1998, The Kyoto Protocol on Climate Change: Resources for the Future) and the need to quantify carbon fluxes was needed to implement the Kyoto Protocol. WO 99/42814 generally describes measurement of isotopes of $CO_2$ in order to determine and monitor global and regional carbon emissions from natural and anthropogenic sources. However, WO 99/42814 only described such systems in broad terms and did not provide any details regarding how specific implementations should be carried out. Notably, even over a decade since the passage of the Kyoto Protocol, no experimental or commercial system currently exists that combines systems for measuring and monitoring both $^{13}C$ and $^{14}C$ in one instrument. Particularly, no reliable and geographic-scale system for the direct measurement, monitoring, verification and accounting of carbon for the purposes of carbon trading is available since the introduction of the Kyoto Protocol (1997).

SUMMARY OF THE INVENTION

The present disclosure provides a system of systems allowing for the first time the integration of carbon flux from both natural and manmade carbon emissions, producing a dual carbon accounting system in which biogenic or natural and fossil/industrial emissions are quantified separately for the purposes of carbon trading. Thus, trading of carbon may be refined as a two-carbon approach (e.g., fossil fuel C and biogenic C), recognizing that both ecosystem function and anthropogenic actions may be differentially priced according to the efficiency of carbon reduction and other factors (e.g., ecological function) afforded by each at any given location and over any given time period. To-date, carbon pricing mechanisms do not account for the two types of carbon even though they are inter-connected reflecting man made and biogenic carbon dynamics.

A system of systems is disclosed that allows for real time, quantitative analysis of isotopologues of atmospheric gases providing for component identification and quantification, such as carbon dioxide ($CO_2$), methane ($CH_4$) and nitrous oxide ($N_2O$). A system of systems is described that collects atmospheric gases, analyzes the gases for isotopic composition using isotopic analyzers and according to requirements for sampling frequency, and harmonizes data across sampling sites using standards and/or global references. Data are provided to a central location and provide isotope-based data products according to specific embodiments and use of conversion methods that result in metric tons of carbon appropriate for carbon trading exchanges. Such products in the case of $CO_2$ can result in a two carbon system (e.g., biogenic and fossil carbon) for trading that can be applied by industries, states, regions, governments, greenhouse gas exchanges, verification bodies for greenhouse gas treaties and by other stakeholders for use in carbon budget analysis, carbon pricing and carbon management.

The disclosure also provides details for the design of a three cell laser system that is calibrated within the instrument, and also can be inter-calibrated with other instruments, e.g., across a landscape in at least some instances, each instrument can be referenced to known global standards, ensuring geographic comparability of data, and thus monetary equivalence when such data are used for carbon trading either as a continuous live trading scheme or as a discontinuous trading scheme. Thus the disclosure represents capability far beyond the capability of a single instrument for either $^{13}C$ or $^{14}C$. Such single analysis determinations are currently the standard for the monitoring of carbon isotopologues and do not address the necessary components to understand nor use the data for purposes of carbon trading.

One aspect of the disclosure involves a system of systems to effectively measure, monitor, report, verify, analyze and monetize data for source terms of greenhouse gases such as carbon budgets reflecting both fossil and biogenic carbon for a given area and over a given period of time with a given frequency of sampling.

Another aspect of the disclosure provides an integrated, multi-isotope ratio instrument for the determination of the concentration and isotopic ratios of one or more isotopologues of a component in a gas, such as carbon dioxide in an ambient air stream. In certain embodiments, integrated, near-simultaneous multi-isotope ratio instrument for the determination of the concentration and isotopic ratios is provided. Relevant isotopologues include without limitation $^{12}C$, $^{13}C$ and $^{14}C$; in some embodiments the measurement of the relevant carbon isotopologues utilizes a three cell laser system.

Another aspect of the disclosure provides a field deployable instrument capable of near-simultaneous and precise measurement of the concentration and isotope ratios of a component in a gas mixture drawn from any source, ranging from point sources such as a flue stack or extracted gas from the ocean, to open spaces of any kind over land or water anywhere on Earth.

Another aspect of the disclosure provides a method employing the system of systems to measure, monitor, identify, report, verify, analyze and make available to carbon exchanges $CO_2$ emissions data based on geographically discrete ensembles of analyzers for large areas of forest, agriculture, water bodies, natural preserves and otherwise non-industrial sources, while providing for the same from industrial and other anthropogenic activities. Placements of such discrete ensembles are determined by use of the system of systems in various initial configurations with selection of one or more preferred configurations for specified measurement and monitoring protocols. Thus, the system of systems is integral in determining the optimal application of the system of systems; without such a system of systems no such effective measuring, monitoring, verification and accounting of carbon can be realized. In the above cases, the disclosure provides for quantitatively defining the fossil and biogenic contributions in a way that has not been reported.

Another aspect of the disclosure provides an instrument or groups of instruments capable of being controlled and queried remotely, as well as providing data in real time via signal transmission to any number of data centers, control points or electronic greenhouse gas trading platforms.

Another aspect of the disclosure provides an instrument capable of near-simultaneous and multiple species analysis of isotopologues of a gas that provides such analysis in a non-destructive manner with respect to the sample thus allowing the same gas stream to be used in additional analyzers of any type, including soil, dissolved inorganic carbon and other forms of carbon of interest. Such simultaneous analyses can be performed on time scales of 1 second or less to hours depending on the time constants of the biological and physical processes to be measured and monitored.

Another aspect of the disclosure provides an instrument that can be expanded to include a variety of other sensors and sampling technologies as they become available and integrated within the three cell system.

Another aspect of the disclosure provides a method employing the system of systems to measure, monitor, identify, report, verify, analyze and provide to carbon exchanges $CO_2$ emission data for a variety of carbon emissions, ranging from industrial sources including discrete point locations, industrial complexes and over large areas of land where such industrial sources may be situated.

Another aspect of the disclosure includes employing one or more universal sealed reference cells for each isotopologue such as $^{12}C$, $^{13}C$ and $^{14}C$ ratios that are or can be made identical for each isotopologue and distributed uniformly within an ensemble(s) of instruments, providing for real time inter-comparability of measurements taken by all instruments across time and space.

Still another aspect of the disclosure includes employing an ensemble of instruments across a defined area each with a sealed standard reference cell in which each instrument measures the isotope ratios of carbon dioxide in the reference cell and in a stream of air or other gas and is compared with other instruments in the ensemble and then with an external master reference gas sealed-cell (e.g. primary reference). A master reference gas sealed-cell may be maintained at a central reference(s) facility ensuring comparability of isotopic data across space and time in real time and providing verification for live carbon trading and monetization across all forms of financial settlement involving carbon derivatives. Such master reference gas sealed cell shall be linked to one or more international gas standards for $^{12}C$, $^{13}C$ and $^{14}C$ ratios providing a network of inter-comparable data sets to be used for carbon trading, managing carbon budgets at a variety of scales and to better understand the global carbon cycle.

Still another aspect of the disclosure includes the transmission of isotopic data in real time via telemetry of any type to a central data collection point where it is analyzed, aggregated and summarized according to time and space coordinates that are then used as inputs in appropriate models. Such models and data result in a total mass of carbon emissions for a given area and time period providing market based carbon trading units such as metric tons of carbon.

Still another aspect of the disclosure includes generating an isotope based equivalency for carbon emissions units, e.g., a two-carbon or dual carbon accounting for biogenic and fossil derived carbon as means to monetize with precision the carbon source amount, and to interface with greenhouse gas exchanges or other trading mechanisms to support carbon pricing, trading and verification of the value of carbon based financial instruments and compliance with carbon emissions regulatory frameworks. Such an interface could consist of models of the atmosphere, including real time meteorological, data, soil, oceans, specific ecosystems and or a variety of models with coupled components of the aforementioned types. The results of data-model fusion are actual mass of carbon fluxes defined spatially and temporally that can be used to calculate carbon units as metric tons for trading.

Still another aspect of the disclosure provides a method of deploying the system of systems for measurement, reporting and verification of carbon emissions sources and quantities at discrete sites within a facility, or within local, regional, state, national and country-wide landscapes, or according to geographical treaty provisions, or across any land or water area on the surface, subsurface or airspace of the planet Earth.

Still another aspect of the invention provides for a method to directly compare ground-based and satellite-based measurements of carbon. In such an embodiment, a satellite may house a sealed cell primary reference standard as well as analytical devices to measure relevant portions of the light spectrum to detect carbon emissions. As the satellite passes over a region with an ensemble of multi-isotopic analyzers the satellite born sealed reference cell will ensure a single baseline for all analyzers in the path of the satellite sensing spectrum, thus offering a direct, real time comparison between the two methods (e.g., ground based, space based). This embodiment could also be used to verify and/or correct baseline features of ensembles whenever the satellite crosses the geographic locations of multi-isotopic analyzers.

In various embodiments, the system of systems, components and related methods may be used with a gas, liquid or solid sample, provided that the solid or liquid sample is first converted into a gas via heating, combustion or other suitable means. In certain embodiments, a method for providing measurements of concentration and isotope ratio of a component in a sample gas mixture, includes the following: A sample gas mixture is loaded into an instrument capable of measuring gas concentration and into an instrument capable of measuring gas isotope ratio. Measurements of gas concentration and gas isotope ratio are performed on said sample gas mixture. In some embodiments, the method further includes removing an interfering species from said gas mixture. In some embodiments, the component of said sample gas mixture is carbon dioxide and said interfering gas species is oxygen. In some embodiments, the method further includes increasing or decreasing the concentration of the component, e.g., carbon dioxide, of the sample gas mixture in order to improve the precision of the measurements. In some embodiments the measurement of gas concentration and measurement of gas isotope ratio are performed substantially simultaneously in a three cell laser system for each of the relevant forms of carbon ($^{12}CO_2$, $^{13}CO_2$, $^{14}CO_2$).

Certain embodiments provide an apparatus for providing measurements of concentration and isotope ratio of a component in a sample gas mixture. The apparatus includes a device for measuring concentration of the component in the sample gas mixture; a device for measuring isotope ratio of the component in the sample gas mixture; and a means to load the sample gas mixture into the concentration measuring device and into the isotope ratio measuring device. In some instances, the concentration measuring device is an infrared gas analyzer. In some embodiments, the isotope ratio measuring device is a laser-based device. In some embodiments, the apparatus further comprises a means to remove one or more interfering species from the sample gas mixture prior to measurement of the component. In some instances, the component of the sample gas mixture is $CO_2$ and the interfering species is oxygen. In some embodiments, the means to remove the interfering gas species comprises one or more chemical scrubbers, or a gas selective membrane, or a means to cryogenically separate the interfering gas species from the component of said sample gas mixture. In some embodiments, the apparatus further comprises a means for increasing or decreasing the concentration of the component of the sample gas mixture in order to improve the precision of the measurements. In some embodiments, the means for increasing the concentration of the component comprises a gas selective membrane, or a cryogenic trap, and the means to decrease the concentration comprises dilution of a sample gas with an inert gas such as nitrogen within an expandable control volume such as a stainless steel bellows. Certain embodiments provide an apparatus for providing simultaneous measurements of concentration and isotope ratio for multiple species of carbon, for example, the simultaneous measurement of the carbon 13 and carbon 14 isotope ratios as compared to $^{12}C$, with a three cell laser system as referred to above.

Certain embodiments provide a method or apparatus as described above for use in a combined analytical system, wherein data results from the system are used to create, manage and monetize carbon budgets. In some instances, the system includes a geographic network of devices. In some embodiments, the network covers a specific industrial site, a nation, a state, a region, a country, boundaries of greenhouse gas treaty or treaties, or any other defined area selected for measuring and monitoring. In some instances results are obtained over the area to reduce uncertainty in carbon trading. An anti-fraud means can be employed to verify carbon emissions reductions by various entities. Means can be provided to comply with any voluntary or mandated emissions reduction policy or to verify multi-national treaties for reduction in carbon emissions. In some embodiments, means are provided to reduce uncertainty in the transaction of any carbon based financial instrument by replacing estimation of carbon emissions with actual real time measurements.

In still other embodiments, the system of systems may include external sealed cell reference gases linked to international reference gases in various configurations separated from field analyzers but used to compare the primary standard with standards used in the field devices via any form of telemetry. In still other embodiments, an external sealed reference cell can be space born in a satellite or space station in which carbon emissions sensors in the satellite offer comparison with ground based multi-isotopic analyzers on the ground that overlap with the satellite ground footprint or to provide an additional reference gas for all multi-isotopic analyzers that communicate and compare data as the space-born reference signal passes over ensembles of multi-isotopic analyzers.

Another aspect of the invention provides a predetermined, desired, or optimal density of the analyzers and measurement frequency distributed throughout the geographic region of interest for the particular application of interest. Measuring, monitoring, analysis, and verification of the carbon flux can provide further insights into the optimal density of the analyzers and measurement frequency of the analyzers.

In certain embodiments, system of systems for generating tradable products that separately quantify biogenic and fossil carbon in forest air is described. The system of systems can include a carbon data collection for collecting carbon flux data in a forest and a data processing system for converting the measured amounts of $^{12}C$, $^{13}C$, and $^{14}C$ isotopes to tradable products that separately quantify biogenic and fossil carbon in the forest. The carbon data collection system for collecting carbon flux data in a forest includes an array of analyzers placed in predetermined representative locations throughout a forest, where each analyzer includes a $^{12}C$ laser device, a $^{13}C$ laser device, a $^{14}C$ laser device, a sample chamber to measure the individual amounts of $^{12}C$, $^{13}C$, and $^{14}C$ isotopes contained in a forest air sample, and a timer to allow measurements of $^{12}C$, $^{13}C$, and $^{14}C$ isotopes at a rate of at least 1 Hz, or 10 Hz, or 50 Hz, or 100 Hz, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the forest air to the data processing system.

In certain embodiments, a method for generating tradable products that separately quantify biogenic and fossil carbon in forest air is described. The method includes (a) placing an array of analyzers at predetermined representative locations throughout a forest, where each analyzer comprises a $^{12}C$ laser device, a $^{13}C$ laser device, a $^{14}C$ laser device, and a sample chamber; (b) collecting forest air samples in the sample chambers of the analyzers and measuring the individual amounts of $^{12}C$, $^{13}C$, and $^{14}C$ isotopes contained in the samples at a rate of at least 1 Hz, or 10 Hz, or 50 Hz, or 100 Hz; (c) obtaining a standard reference baseline with a standard reference gas module; (d) calibrating the measured amounts of $^{12}C$, $^{13}C$, and $^{14}C$ isotopes from each of the analyzers based on the standard reference baseline; (e) sending the measured amounts of $^{12}C$, $^{13}C$, and $^{14}C$ isotopes in the forest air samples to a data processing system; and (f) converting the measured amounts of $^{12}C$, $^{13}C$, and $^{14}C$ isotopes in the data processing system to tradable products that separately quantify biogenic and fossil carbon in the forest.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{13}C$, and $^{14}C$ isotopes contained in the global reference sample so that the measured amounts of $^{12}C$, $^{13}C$, and $^{14}C$ isotopes in the forest air samples can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations throughout the forest.

In certain embodiments, the predetermined representative locations include borders of discrete forest areas, wherein said borders include a region, a state, a group of states, a border configuration defining a greenhouse gas treaty or other convention that requires monitoring greenhouse gases.

In certain embodiments, the predetermined representative locations include above the forest canopy, below the forest canopy and at the forest floor.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the forest.

In certain embodiments, system of systems for generating tradable products that separately quantify biogenic and fossil carbon in soil is described. The system of systems can include a carbon data collection for collecting carbon flux data in soil and a data processing system for converting the measured amounts of $^{12}C$, $^{13}C$, and $^{14}C$ isotopes to tradable products that separately quantify biogenic and fossil carbon in the soil. The carbon data collection system for collecting carbon flux data in a soil includes an array of analyzers placed in predetermined representative locations throughout the soil, where each analyzer includes a $^{12}C$ laser device, a $^{13}C$ laser device, a $^{14}C$ laser device, a sample chamber to measure the individual amounts of $^{12}C$, $^{13}C$, and $^{14}C$ isotopes contained in a soil sample, and a timer to allow measurements of $^{12}C$, $^{13}C$, and $^{14}C$ isotopes at a rate of at least 1 Hz, or 10 Hz, or 50 Hz, or 100 Hz, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the soil to the data processing system.

In certain embodiments, a method for generating tradable products that separately quantify biogenic and fossil carbon in soil is described. The method includes (a) placing an array of analyzers at predetermined representative locations throughout a soil, where each analyzer comprises a $^{12}C$ laser device, a $^{13}C$ laser device, a $^{14}C$ laser device, and a sample chamber; (b) collecting soil samples in the sample chambers of the analyzers and measuring the individual amounts of $^{12}C$, $^{13}C$, and $^{14}C$ isotopes contained in the samples at a rate of at least 1 Hz, or 10 Hz, or 50 Hz, or 100 Hz; (c) obtaining a standard reference baseline with a standard reference gas module; (d) calibrating the measured amounts of $^{12}C$, $^{13}C$, and $^{14}C$ isotopes from each of the analyzers based on the standard reference baseline; (e) sending the measured amounts of $^{12}C$, $^{13}$, and $^{14}C$ isotopes in the soil samples to a data processing system; and (f) converting the measured amounts of $^{12}C$, $^{13}C$, and $^{14}C$ isotopes in the data processing system to tradable products that separately quantify biogenic and fossil carbon in the soil.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{13}C$, and $^{14}C$ isotopes contained in the global reference sample so that the measured amounts of $^{12}C$, $^{13}C$, and $^{14}C$ isotopes in the soil samples can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations throughout the soil.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the soil.

In certain embodiments, the measured amount fossil carbon relative to the measured biogenic carbon can indicate damage in the soil.

In certain embodiments, system of systems for generating tradable products that separately quantify biogenic and fossil carbon in an agricultural area is described. The system of systems can include a carbon data collection for collecting carbon flux data in agricultural area and a data processing system for converting the measured amounts of $^{12}C$, $^{13}C$, and $^{14}C$ isotopes to tradable products that separately quantify biogenic and fossil carbon in the agricultural area. The carbon data collection system for collecting carbon flux data in the agricultural area includes an array of analyzers placed in predetermined above-ground and sub-surface locations in an agricultural area, where each analyzer includes a $^{12}C$ laser device, a $^{13}C$ laser device, a $^{14}C$ laser device, a sample chamber to measure the individual amounts of $^{12}C$, $^{13}C$, and $^{14}C$ isotopes contained in the above-ground and sub-surface location samples, and a timer to allow measurements of $^{12}C$, $^{13}C$, and $^{14}C$ isotopes at a rate of at least 1 Hz, or 10 Hz, or 50 Hz, or 100 Hz, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the agricultural area to the data processing system.

In certain embodiments, a method for generating tradable products that separately quantify biogenic and fossil carbon in an agricultural area is described. The method includes (a) placing an array of analyzers at predetermined representative above-ground an sub-surface locations in an agricultural area, where each analyzer comprises a $^{12}C$ laser device, a $^{13}C$ laser device, a $^{14}C$ laser device, and a sample chamber; (b) collecting samples of carbon gas in the above-ground and sub-surface locations in the sample chambers of the analyzers and measuring the individual amounts of $^{12}C$, $^{13}C$, and $^{14}C$ isotopes contained in the samples at a rate of at least 1 Hz, or 10 Hz, or 50 Hz, or 100 Hz; (c) obtaining a standard reference baseline with a standard reference gas module; (d) calibrating the measured amounts of $^{12}C$, $^{13}C$, and $^{14}C$ isotopes from each of the analyzers based on the standard reference baseline; (e) sending the measured amounts of $^{12}C$, $^{13}C$, and $^{14}C$ isotopes in the above-ground and sub-surface samples to a data processing system; and (f) converting the measured amounts of $^{12}C$, $^{13}C$, and $^{14}C$ isotopes in the data processing system to tradable products that separately quantify biogenic and fossil carbon in the agricultural area.

In certain embodiments, the above-ground locations can include 0 to 20 meters above the ground. In some other embodiments, the sub-surface locations can include 0 to 100 meters below the surface.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{13}C$, and $^{14}C$ isotopes contained in the global reference sample so that the measured amounts of $^{12}C$, $^{13}C$, and $^{14}C$ isotopes in the agricultural area samples can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations throughout the agricultural area.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the agricultural area.

In certain embodiments, system of systems for generating tradable products that separately quantify biogenic and fossil carbon in a body of water is described. The system of systems can include a carbon data collection for collecting carbon flux data in a body of water and a data processing system for converting the measured amounts of $^{12}C$, $^{13}C$, and $^{14}C$ isotopes to tradable products that separately quantify biogenic and fossil carbon in the body of water. The carbon data collection system for collecting carbon flux data in a soil includes an array of analyzers placed in predetermined representative locations throughout the body of water, where each analyzer includes a $^{12}C$ laser device, a $^{13}C$ laser device, a $^{14}C$ laser device, a gas stripping device capable of stripping dissolved gases from the body of water, a sample chamber to measure the individual amounts of $^{12}C$, $^{13}C$, and $^{14}C$ isotopes contained in dissolved gas stripped from the body of water sample, and a timer to allow measurements of $^{12}C$, $^{13}C$, and $^{14}C$ isotopes at a rate of at least 1 Hz, or 10 Hz, or 50 Hz, or 100 Hz, or at least once an hour, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the body of water to the data processing system.

In certain embodiments, a method for generating tradable products that separately quantify biogenic and fossil carbon in a body of water is described. The method includes (a) placing an array of analyzers at predetermined representative locations throughout a body of water, where each analyzer comprises a $^{12}C$ laser device, a $^{13}C$ laser device, a $^{14}C$ laser device, and a sample chamber, and a gas stripping device capable of stripping dissolved gases from the body of water; (b) collecting water samples in the analyzers; (c) stripping dissolved gases from the water samples; (d) collecting the gases in the sample chambers of the analyzers and measuring the individual amounts of $^{12}C$, $^{13}C$, and $^{14}C$ isotopes contained in the samples at a rate of at least 1 Hz, or 10 Hz, or 50 Hz, or 100 Hz, or at least once an hour; (e) obtaining a standard reference baseline with a standard reference gas module; (f) calibrating the measured amounts of $^{12}C$, $^{13}C$, and $^{14}C$ isotopes from each of the analyzers based on the standard reference baseline; (g) sending the measured amounts of $^{12}C$, $^{13}C$, and $^{14}C$ isotopes in the samples of dissolved gases in the body of water to a data processing system; and (h) converting the measured amounts of $^{12}C$, $^{13}C$, and $^{14}C$ isotopes in the data processing system to tradable products that separately quantify biogenic and fossil carbon in the body of water.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{13}C$, and $^{14}C$ isotopes contained in the global reference sample so that the measured amounts of $^{12}C$, $^{13}C$, and $^{14}C$ isotopes in the water samples can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations throughout the body of water.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the body of water.

In certain embodiments, the data processing system tracks the measured amounts of $^{12}C$, $^{13}C$, and $^{14}C$ isotopes over a period of time to monitor change of nutrients in the body of water.

In certain embodiments, system of systems for generating tradable products that separately quantify biogenic and fossil carbon in flue gases is described. The system of systems can include a carbon data collection for collecting carbon flux data from flue gases and a data processing system for converting the measured amounts of $^{12}C$, $^{13}C$, and $^{14}C$ isotopes to tradable products that separately quantify biogenic and fossil carbon in the flue gases. The carbon data collection system for collecting carbon flux data from flue gases includes an array of analyzers placed in predetermined representative locations exposed to flue gases, where each analyzer includes a $^{12}C$ laser device, a $^{13}C$ laser device, a $^{14}C$ laser device, a sample chamber to measure the individual amounts of $^{12}C$, $^{13}C$, and $^{14}C$ isotopes contained in a flue gas sample, and a timer to allow measurements of $^{12}C$, $^{13}C$, and $^{14}C$ isotopes at a rate of at least 1,440 times a day, 1 Hz, or 10 Hz, or 50 Hz, or 100 Hz, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the flue gases to the data processing system.

In certain embodiments, a method for generating tradable products that separately quantify biogenic and fossil carbon in flue gases is described. The method includes (a) placing an array of analyzers at predetermined representative locations exposed to flue gases, where each analyzer comprises a $^{12}C$ laser device, a $^{13}C$ laser device, a $^{14}C$ laser device, and a sample chamber; (b) collecting flue gas samples in the sample chambers of the analyzers and measuring the individual amounts of $^{12}C$, $^{13}C$, and $^{14}C$ isotopes contained in the samples at a rate of at least 1,440 times a day, 1 Hz, or 10 Hz, or 50 Hz, or 100 Hz; (c) obtaining a standard reference baseline with a standard reference gas module; (d) calibrating the measured amounts of $^{12}C$, $^{13}C$, and $^{14}C$ isotopes from each of the analyzers based on the standard reference baseline; (e) sending the measured amounts of $^{12}C$, $^{13}C$, and $^{14}C$ isotopes in the samples of flue gas to a data processing system; and (f) converting the measured amounts of $^{12}C$, $^{13}C$, and $^{14}C$ isotopes in the data processing system to tradable products that separately quantify biogenic and fossil carbon in the flue gases.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{13}C$, and $^{14}C$ isotopes contained in the global reference sample so that the measured amounts of $^{12}C$, $^{13}C$, and $^{14}C$ isotopes in the flue gas samples can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations exposed to flue gases.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the flue gases.

In certain embodiments, the data processing system tracks the measured amounts of $^{12}C$, $^{13}C$, and $^{14}C$ isotopes over a period of time to monitor reduction of combustion of fossil carbon in accordance with regulatory or voluntary emission guidelines.

In certain embodiments, system of systems for generating tradable products that separately quantify biogenic and fossil carbon near a nuclear power plant is described. The system of systems can include a carbon data collection for collecting carbon flux data from flue gases and a data processing system for converting the measured amounts of $^{12}C$, $^{13}C$, and $^{14}C$ isotopes to tradable products that separately quantify biogenic and fossil carbon near the nuclear power plant. The carbon data collection system for collecting carbon flux data near a nuclear power plant includes an array of analyzers placed in predetermined representative locations near a nuclear power plant, where each analyzer includes a $^{12}C$ laser device, a $^{13}C$ laser device, a $^{14}C$ laser device, a sample chamber to measure the individual amounts of $^{12}C$, $^{13}C$, and $^{14}C$ isotopes contained in discharges of the nuclear power plant, and a timer to allow measurements of $^{12}C$, $^{13}C$, and $^{14}C$ isotopes at a rate of at least 1 Hz, or 10 Hz, or 50 Hz, or 100 Hz, a standard reference gas module for obtaining a standard reference baseline and calibrating the measured amounts of the $^{12}C$, $^{13}C$, and $^{14}C$ isotopes from each of said analyzers based on the standard reference baseline and a telemetry device for sending measured amounts of $^{12}C$, $^{13}C$, and $^{14}C$ isotopes in the discharges of the nuclear power plant to the data processing system.

In certain embodiments, a method for generating tradable products that separately quantify biogenic and fossil carbon near nuclear power plant is described. The method includes (a) placing an array of analyzers at predetermined representative locations near a nuclear power plant, where each analyzer comprises a $^{12}C$ laser device, a $^{13}C$ laser device, a $^{14}C$ laser device, and a sample chamber; (b) collecting samples of discharges of the nuclear power plant in the sample chambers of the analyzers and measuring the individual amounts of $^{12}C$, $^{13}C$, and $^{14}C$ isotopes contained in the samples at a rate of at least 1 Hz, or 10 Hz, or 50 Hz, or 100 Hz; (c) obtaining a standard reference baseline with a standard reference gas module; (d) calibrating the measured amounts of $^{12}C$, $^{13}C$, and $^{14}C$ isotopes from each of the analyzers based on the standard reference baseline; (e) sending the measured amounts of $^{12}C$, $^{13}C$, and $^{14}C$ isotopes in the samples of discharge of the nuclear power plant to a data processing system; and (f) converting the measured amounts of $^{12}C$, $^{13}C$, and $^{14}C$ isotopes in the data processing system to tradable products that separately quantify biogenic and fossil carbon in the discharges of the nuclear power plant.

In certain embodiments, each analyzer includes a standard reference gas module so that a standard reference baseline can be obtained at each analyzer.

In certain embodiments, the system of systems further includes a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample, and a calibration system for standardizing the measured amount of $^{12}C$, $^{13}C$, and $^{14}C$ isotopes from the analyzers of the data collection system based on said measured amounts of $^{12}C$, $^{12}C$, $^{13}C$, and $^{14}C$ isotopes contained in the global reference sample so that the measured amounts of $^{12}C$, $^{13}C$, and $^{14}C$ isotopes in the discharges of the nuclear power plant can be standardized based on measured amounts of $^{12}C$, $^{13}C$, and $^{14}C$ isotopes in a global reference sample. In certain embodiments, the global reference sample can be located in a satellite.

In certain embodiments, at least 25, 50, 75, or 100 analyzers are placed at predetermined representative locations near the nuclear power plant.

In certain embodiments, the data processing system can further include one or more conversion systems parameterized for biogenic and fossil fuel carbon to convert the measured amounts of $^{12}C$, $^{13}C$, and $^{14}C$ isotopes in the data processing system to tradable products that separately quantify biogenic and fossil carbon in the discharges of the nuclear power plant.

BRIEF DESCRIPTION OF THE FIGURES

FIG. 7 is a block diagram of an embodiment of a sample conditioning unit as incorporated in the apparatus of FIG. 6.

FIG. 8 is a block diagram of another embodiment of a sample conditioning unit as incorporated in the apparatus of FIG. 6, such sample conditioning unit utilizing a gas selective membrane.

DETAILED DESCRIPTION

Figure 1:
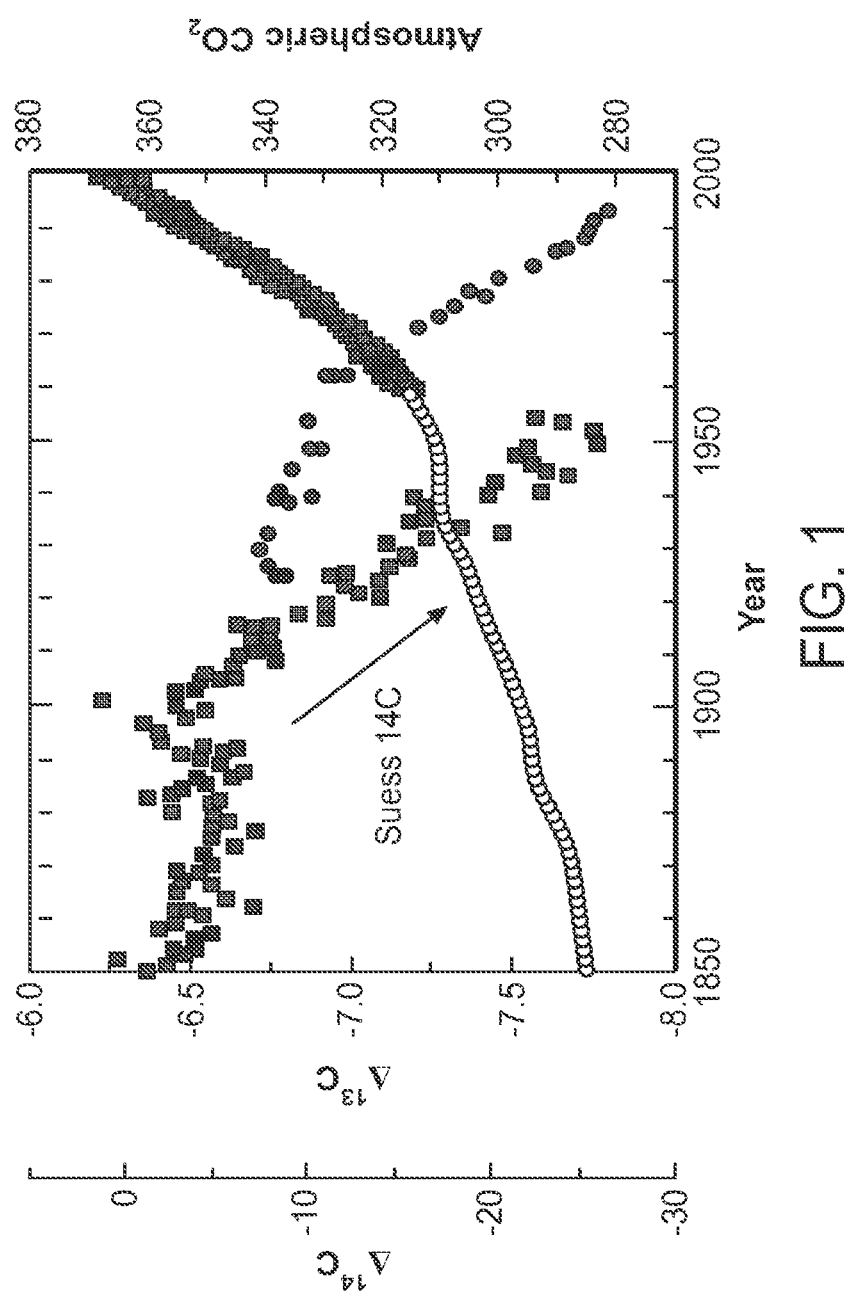
FIG. 1 is a summary graph of the concentrations of $^{14}CO_2$, $^{13}CO_2$ and $CO_2$ concentration spanning the years 1850 to 2000, as derived from a variety of sources (Kosovic 2008).

Long Recognized Needs for Direct Measuring and Monitoring of Carbon Emissions not Met Currently, carbon emissions as gaseous carbon dioxide are largely estimated from a variety of secondary data including amount of fuel burned, combustion efficiencies and economic data. Carbon inventories, required under the United Nations Framework Convention on Climate Change, are self-reported and essentially un-verified (Ellerman and Joskow 2008). Actual measurements of total carbon dioxide in the atmosphere are made by a number of stakeholders but do not reveal the source or type of emissions and may not be directly tied to individual sources of $CO_2$ which are varied in origin and magnitude (e.g., oceanic, forests, industry, carbon capture and storage). Indeed, the level of monitoring and appropriate technologies needed to integrate emissions data to support financial markets were not envisioned in the pre-Kyoto period of regulatory compliance. The brief history of the European Union Emissions Trading Scheme (Convery and Redman 2007) has shown that direct measuring, monitoring, reporting, verification and monetization requirements have not been successfully met as evidenced by price fluctuations, difficulties in placing caps and recognition that estimates of emissions fluxes can be as high as 10% of total emissions (Kosovic, 2008) and potentially much higher at sub-continental scales and sub-annual scales (e.g., Turnbull et al., 2006). Moreover, the Kyoto accord was not designed to incorporate carbon flux from natural sources, such as the world's forests and oceans, with industrial emissions, due to an inadequate measuring, monitoring and reporting network for $CO_2$ flux that requires diagnostic carbon species representing ecosystem function. Thus, even though the importance and need for measuring and monitoring large scale carbon exchange, such as carbon sequestration in forests, has long been acknowledged, no such system is in place. Under current operating protocols direct measurements of carbon emissions resulting from fossil fuel combustion or from natural biogenic sources are not used to enforce treaty provisions or to quantify the potential of forest carbon sequestration.

Both sides of the emerging carbon markets (e.g., bid (buyer) and ask (seller)) require quantification of the traded carbon entity for credible pricing and market support while global scale data are required to assess the effectiveness of carbon markets as a response to climate change and uncertainties in biospheric performance (e.g., Canadell et al., 2007; Raupach et al., 2007, US Climate Change Science Program 2007). Thus, effective multi-scale measuring and monitoring would be an independent means to verify Kyoto commitments as specified by the Kyoto Protocol or by other protocols, greenhouse gas treaties or conventions (e.g., Regional Greenhouse Gas Initiative 2009), to integrate carbon budgets across the landscape, as well as quantify carbon flux of planetary surfaces within the region of carbon management. However, despite a long standing need and the recognized importance of such a monitoring system, no scalable carbon accounting system based on direct measurement is available.

Potential of Rare Forms of Carbon to Meet Measuring and Monitoring Needs

Rare forms of carbon, namely, $^{13}C$ and $^{14}C$, are key to differentiating biogenic from fossil derived $CO_2$ yet these rare forms of carbon are not widely used due to difficulty in making rapid, reliable, comparable and verified measurements. Rare forms of carbon are diagnostic by virtue of their concentrations in $CO_2$ and in the manner in which these forms are fractionated by biological and physical processes (Keeling 1979; Graven et al., 2009). A means to making reliable and comparable measurements of the rare forms of carbon widespread in the planetary environment (e.g., field sites worldwide) would provide a foundation for quantitative carbon metrics through time and space and the basis for carbon pricing and trading.

While concentrations of $CO_2$ can be measured with high precision and are widespread, now represented by some 252 stations from 57 countries (WMO 2009; Peters et al., 2007). concentration measurements alone do not provide a full deconvolution of the sources and sinks of this greenhouse gas. Thus, an intrinsic partial carbon accounting creates uncertainty in resulting budgets used to assess project performance, placing caps (for cap and trade routines) and ultimately determination of the pricing of carbon in a variety of markets. However, rare forms of carbon, specifically carbon isotopes, intrinsic to and embedded in carbon dioxide dynamics at all scales in the biosphere and atmosphere offer a means to identify specific carbon dioxide sources, such as from fossil fuels, as well as provide data on the functioning of the natural carbon cycle within a defined landscape. The data representation and data rate (e.g., continuous, daily, weekly, monthly) for the rare forms of carbon, such as $^{13}CO_2$ and $^{14}CO_2$, are minimal in comparison to $CO_2$ concentration data (Tans et al. 1996); $^{14}CO_2$ data are particularly limited.

Although determination of the isotopologues of $CO_2$ ($^{13}C$, $^{14}C$) can offer valuable constraints on relevant carbon source/sink terms (e.g., Tans et al., 1996; Turnbull et al., 2010; Graven et al., 2009; Riley et al., 2008), a feasible "system of systems" required to measure, monitor, report, verify, account and manage carbon budgets and related financial instruments based on actual measurements of carbon isotopologues is not available. Rather, isotopologues are typically individually acquired at specific locations using different instrumentation and methods. They are determined primarily by discrete single analyses of flask samples that are subsequently analyzed by high vacuum magnetic sector isotope ratio mass spectrometers (IRMS) at considerable cost and time (e.g., Tans et al., 1996; Vaughn et al., 2010). Or, in the case of atmospheric $^{14}CO_2$ analyses, such analyses are performed using a variety of β-emitter detectors and accelerator mass spectrometers (AMS) according to sample size and treatment (e.g., Stork et al., 1997; Tuniz 2001).

Direct, rapid (e.g., range from sub-second data to longer as required)) and widespread measurement of $^{14}C$ in atmospheric $CO_2$ would provide unequivocal and quantitative data for fossil fuel sources. Such analyses could be linked to internationally recognized standards representing standard reference material (e.g., Stuiver and Polach 1977), for use as primary standards as well as global reference frameworks for $^{14}CO_2$ and $^{13}CO_2$ (Boaretto et al., 2002; Vaughn et al., 2010). The composition of the atmosphere with respect to $^{13}CO_2$ and $^{14}CO_2$ is well understood from a global perspective as reflected in the Seuss Effect (Levin et al., 1989; 1995; Keeling 1979), however, widespread analysis of $^{14}CO_2$ will serve as independent verification of fossil fuel based emissions on a variety of scales, particularly at local and regional scales important to track emissions from specified areas (Turnbull et al., 2006). The large difference in the natural abundances of the rare forms of carbon (e.g., $^{13}C$ 1.1%; $^{14}C$ $10^{-10}$%) are reflected both in the instrumentation used, the difficulty of making reliable measurements and the data rate for each species. The data rate or sampling rate (e.g., number of samples per day or samples per second) for high precision $^{13}C$ and $^{14}C$ measurements is quite small compared to data collected for total $CO_2$ concentration, resulting in far too few measurements to support carbon trading. Thus, despite the long-felt need and established scientific validity of isotopic measurements, there are no widely distributed and integrated analyzers upon which to base a method or methods to directly link carbon emissions data with carbon trading and carbon management.

Thus, a system that offers direct, rapid, simultaneous, multi-scale and multi-isotopic analytical capability for the important isotopologues of $^{13}C$ and $^{14}C$, and that could operate in the field on a continuous or near continuous basis, would be a highly valuable system to measure, monitor, report, verify, account for and manage carbon budgets, carbon trading and planetary climate change. To date, isotopic data have not been used to measure or monitor carbon emissions for the purposes of carbon trading, or to support the use of current carbon or related greenhouse gas financial instruments, or to assess compliance with either regulatory or voluntary emissions frameworks, despite a clear and well recognized need for such a system (UNFCC 2009).

According to a study conducted by the Lawrence Livermore National Laboratory (Kosovic et al., 2008), uncertainties in fuel consumption and oxidation efficiencies, representing the main sources of fossil fuel based $CO_2$, are estimated to be at least ±10%. In the context of the 2008 dollar volume of carbon traded at $129 US billion, the uncertainty could reach ±12.9 billion dollars. Thus, a system of systems that could reduce economic uncertainty would be highly valuable to stakeholders representing buyers and sellers of carbon credits, and assure policymakers and the public that carbon based trading systems are managed properly, are transparent and stable and can be protected from fraud. While it is widely recognized that such a system of systems is needed to reduce economic uncertainty and replace estimation with direct measurement, no such system has been devised or is currently operating.

Carbon Budgets

Deconvolution of Carbon Budgets Using Isotopic Forms of Carbon

Fossil fuel emissions and the resultant changes in carbon budgets are the focus of the Kyoto Protocol mechanisms (e.g., IPCC 2008) and other carbon trading exchanges and platforms. They are the basis for carbon trading and carbon based financial instruments in the EU and the emerging voluntary markets in the US, such as the Chicago Climate Exchange (CCX 2009). Carbon budgets are difficult to construct without information about component sources. Since total $CO_2$ as commonly measured does not provide source or component information, it is clear that isotopic data for the rare forms of carbon as discussed above would be highly valued and of importance in measuring, monitoring, verifying and accounting for fossil fuel emissions.

With respect to carbon 13, this isotope alone does not distinguish fossil fuel $CO_2$ from natural $CO_2$, thus making it impossible to determine either with this isotope alone. The dilution of atmospheric $^{14}CO_2$ with fossil fuel derived $CO_2$ is well known and understood. FIG. 1 (adapted from Kosovic et al., 2008) shows a graph spanning the years 1850 to 2000 for measurements of $^{14}CO_2$ (squares), $^{13}CO_2$ (filled circles) and the atmospheric concentration of $CO_2$ (small open circles) derived from tree rings, ice cores and the modern atmosphere, respectively. The decrease in $^{14}CO_2$ in the atmosphere over this period is directly related to fossil fuel additions linked to increasing $CO_2$ concentrations of the atmosphere. The half life of $^{14}C$ is approximately 5730 years making it an ideal, direct and sensitive tracer for fossil based $CO_2$ emissions. Fossil fuel does not contain $^{14}C$, having long since naturally decayed during the millions of years of coal and natural gas formation. Thus, the addition of fossil fuel $CO_2$ devoid of $^{14}C$ strongly dilutes the modern $^{14}C$ background, which is comprised of natural $^{14}C$ production (Libby et al., 1949) and of $^{14}C$ released from atomic bombs (Randerson et al., 2002). The $^{13}CO_2$ record, shown also as decreasing, is also linked to the fossil fuel record, because plant-based fossil fuels (e.g., coal and natural gas) are depleted in $^{13}C$ with respect to the atmosphere. Measurement of $^{14}CO_2$ concentration of the atmosphere to 2 per mil (‰) precision allows model calculation of about 2 ppm fossil fuel $CO_2$, within a background of 380 ppm, thus defining the fossil fuel input for a given source (Kosovic et al., 2008; Graven et al., 2009; Riley et al., 2008). The graph also clearly shows that $^{13}C$ alone cannot differentiate fossil fuel carbon from biogenic carbon.

Thus, recognizing that $^{14}C$ measurements and $^{13}C$ measurements are rare in comparison to total $CO_2$ measurements, an apparatus and system of systems for $^{13}C$ and $^{14}C$ with acceptable precision and sensitivity to effectively track isotopes in relation to fossil fuel and biogenic emissions in real time is clearly needed and long sought as an important method for verification of fossil fuel emissions and treaty provisions at meaningful spatial scales for management and monetization. However no such system is available or operating.

Figure 2:
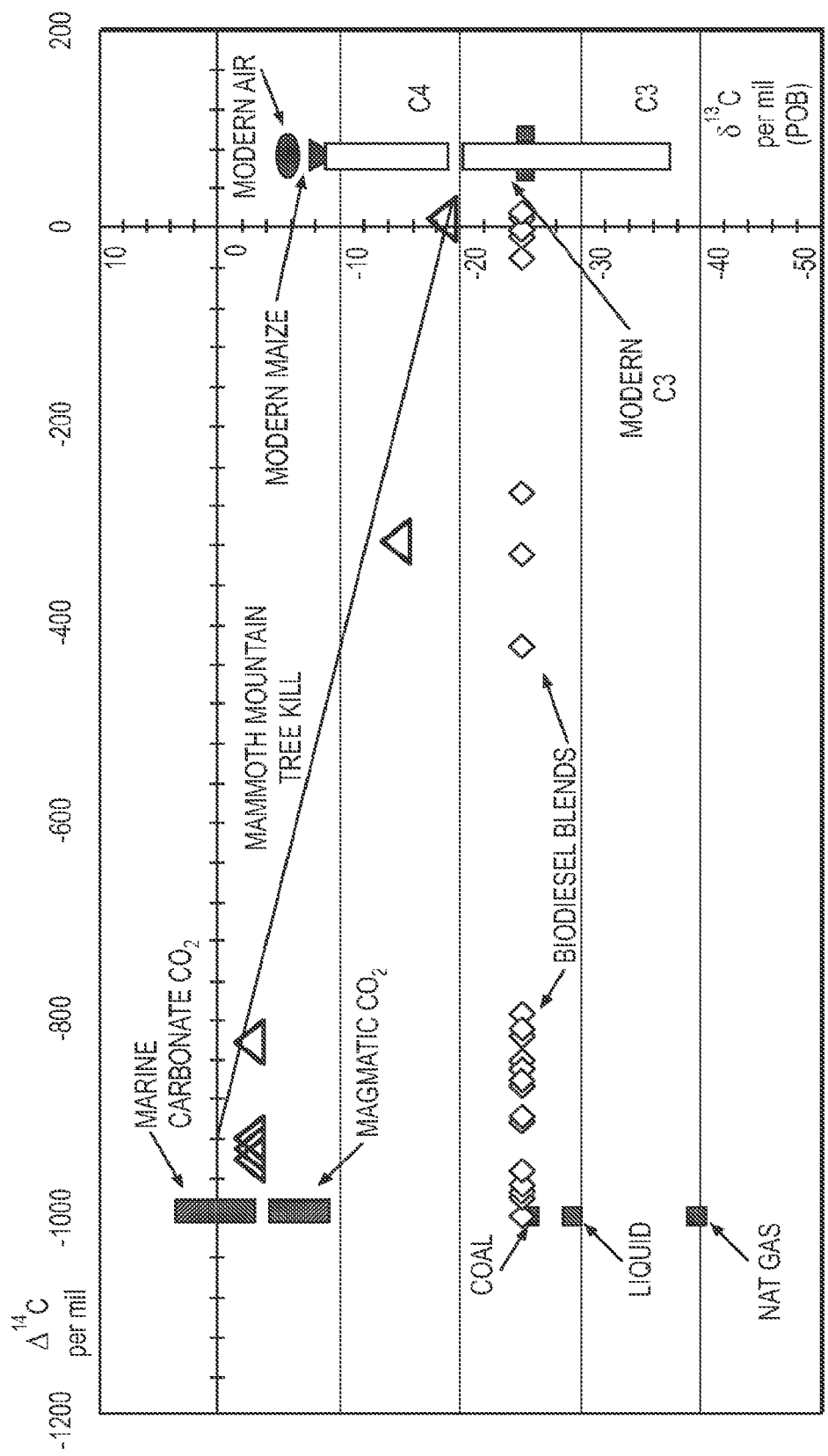
FIG. 2 is a plot of $^{13}C$ versus $^{14}C$ isotope ratios for gaseous emissions of fossil fuels, modern plants and analyses of liquid biofuels with varying concentrations of petrochemical fuels. The $^{13}C$ versus $^{14}C$ data represent relevant source terms in the biosphere reflecting both fossil fuel and biogenic carbon sources as follows. Biodiesel blends (diamonds) (Reddy et al., 2008); Values for natural gas, liquid fuels and coal (filled squares) (Widory 2006); Modern grasses (solid bar) (Riley et al., 2008); Modern maize (filled inverted triangle) (Hsuch et al., 2007); Modern air (oval) (Levin et al., 2003); Open box representing range of modern C4 plants (O'Leary, 1988); Open box representing range of modern C3 plants (O'Leary, 1998); Solid box representing magnetic $CO_2$ (Mary & Jambon, 1987); Open triangles represent soil $CO_2$ from tree kill and normal tree sites in the Mammoth Mountain area (Farrar et al., 1995).

The value of using both $^{13}C$ and $^{14}C$ measurements is illustrated in FIG. 2. The figure shows carbon 13 (y-axis) versus carbon 14 (x-axis) isotope ratios, published as indicated in the detailed descriptions of the Figures. It is observed that modern plants of the C3 type (representing most plants and trees) and fossil fuels and emissions thereof overlap almost entirely with respect to carbon 13 ratios (−20 to −38 per mil, FIG. 2). However, the $^{14}C$ data clearly separate modern from fossil fuel sources with a range from −1000 $\Delta^{14}C$ per mil, representing 100% fossil fuel carbon, to approximately +50 per mil, representing modern background $^{14}C$. Specifically, the value for carbon 13 derived from coal is very similar to that for modern C3 gases in $^{13}C$, but clearly different in $^{14}C$ ratios. As fossil fuel sources are devoid of $^{14}C$ content, all of these sources unequivocally are at 0% $^{14}C$ or register as −1000 $\Delta^{14}C$ per mil when analyzed. Moreover, one can see that carbon emissions from industrial fuels including natural gas and coal are somewhat distinguishable one from the other based on $^{13}C$ but not $^{14}C$. Automobile produced $CO_2$ carbon isotope ratios are also distinct in carbon 13 but not in carbon 14 ratios as indicated by the fossil and modern brackets shown on the graph. Thus, a system of systems capable of measuring both $^{13}C$ and $^{14}C$ composition would be valuable for determining fossil and biogenic components of any gas stream that can be analyzed. For example, biofuel blend compositions (Reddy et al., 2008), increasingly mandated for power production facilities, can be readily verified as to advertised biogenic/fossil fuel compositions (note the diamond symbols in FIG. 2). Thus, a system of systems that provided for the differentiation of fossil fuel derived $CO_2$ and natural or biogenic $CO_2$ would fulfill a long standing and much sought after system to measure, monitor, verify and account for fossil fuel emissions and the potential effects of such emissions on natural ecosystems. However, no such system exists or is currently operating.

Further, one can see that $^{13}C$ and $^{14}C$ ratios can be used to identify sources of natural $CO_2$ in cases where C4 plants (O'Leary 1998) ($^{13}C$ values range from −19 to −11 per mil, FIG. 2) versus C3 plants are concerned (O'Leary 1998). C4 plants are common in dry, arid areas representative of plains and other non-forested areas. Such a distinction would be useful in the monitoring of many ecosystems of the world where evidence of carbon release or uptake by the biosphere in relation to rainfall and shifting C3 versus C4 composition could establish regional climate change forecasts, including in which areas carbon is a sink or a source of $CO_2$ and vice-versa. However, despite the recognized importance of monitoring of such changes in carbon uptake or release, there are no systems of systems currently in use that directly measure such changes.

An additional feature of the graph shown relates to the assessment of ecosystem function as influenced by carbon emissions. The data shown from Mammoth Mountain, a known and well studied area where natural magnetic $CO_2$ is released, represented by open triangles, clearly delineate soil $CO_2$ associated with tree death from soil $CO_2$ in areas of natural ecosystem function. The Mammoth Mountain data clearly show that using both $^{14}C$ and $^{13}C$ data to monitor ecosystem function, as potentially affected by release of $CO_2$ from large scale projects that capture and store $CO_2$ underground, is an effective and sensitive means to measure, monitor, verify and account for such emissions to be used for carbon credits. Carbon capture and storage is viewed widely as a means to manage carbon emissions from coal-based power production (Zwaan and Gerlagh 2009, Friedmann 2007) resulting in carbon credits based on avoidance of carbon emissions. However, no unequivocal means to measure, monitor, assess or to provide or an early warning system for leakage from such carbon capture and storage projects is available, though it is widely acknowledged that such a system is urgently needed (Ha-Duong and Loisel 2009). Thus, it would be highly valuable to have a system of systems with means to integrate natural and industrial/anthropogenic carbon flux resulting in data compatible with carbon based financial instruments. Such a system does not currently exist although such a system is needed to advance the capability for measuring, monitoring, verification and accounting carbon credits based on carbon reduction technologies such as carbon capture and storage.

Currently, networks of gas collection and analysis are managed by governmental entities, such as the National Oceanic Atmospheric Association (NOAA) and Commonwealth Scientific and Industrial Research Organization (CSIRO). The sites for which both $^{13}C$ and $^{14}C$ analyses are conducted by various groups, such as NOAA and CSIRO, are small, at around 20 locations representing primarily oceanic sample sites. For example, Turnbull et al. (2007) utilize measurements from only two locations for a study on the variation of $^{14}CO_2$ in North America. Data results of Turnbull et al. (2007) clearly indicate that a vast increase in the data rate of $^{14}CO_2$ is required for high resolution of carbon emissions. The current program of $^{14}CO_2$ sampling by governmental agencies is thus not sufficient to provide data that can be used to support carbon trading and related markets.

Based on data to date, changes in relative abundances of different isotopologues on the order of $10^{-4}$ or 0.1 per mil have significance in analysis of sources and sinks (Keeling 1958), particularly for $^{13}C$. Moreover, in demanding field studies to adequately determine atmosphere-ecosystem exchange of $CO_2$ in forests, for example, eddy covariance measurements are required (Saleska 2006; Gulden et al., 1996). In this case a very fast response time for analysis of $^{13}CO_2$ on the order of 1 Hertz or less for analysis times with a precision of a minimum of 0.1 per mil $^{13}C$ ratios are required to capture the full biological response over discrete time periods and over diurnal periods of forests to a variety of factors (Saleska et al., 2006). Thus, a fast response time, stability and high precision would also be useful in cases where forest exchanges of $CO_2$ are needed. Currently, as discussed previously, while recognized as important and valuable, forests are not included as offsets under the Kyoto Protocol due to the difficulty of measuring and quantifying forest flux of carbon stored (e.g., Saleska et al., 2006) in the soil and the above ground biomass. Thus, a system of systems that is capable of measuring and quantifying forest carbon flux on a variety of time scales including very fast sampling periods to capture the fine scale and diurnal variations in forest biological response would be important to providing a basis for forest carbon credits under the current Kyoto Protocol and other conventions or treaties allowing inclusion of the forests of the world in carbon managed and carbon reduced paradigms.

Moreover, a reliable and verified accounting of forest flux could also be used to establish carbon trading prices and volumes in any number of voluntary exchanges such as the Gold Standard and others (Hamilton et al., 2008). The addition of monitoring the $^{14}C$ flux of forests has not been used in carbon trading platforms or served as the basis of carbon financial instruments. The addition of $^{14}C$ data in measuring, monitoring, verifying and accounting for carbon storage in forests will provide an additional criteria to constrain carbon flux determinations and indicate the extent to which forests take up fossil fuel emissions, thereby valuing forests to mitigate such emissions. Thus, while the importance and scientific understanding of forest carbon processes are well established and the need for widespread measuring, monitoring, verification and accounting is widely recognized as critical, no such system of systems has been devised or is currently operating.

Data Limited Models for Carbon Emissions Determination

Currently, models for deriving reliable carbon flux are data limited because, as explained above, widespread systems for measuring, monitoring, verification and accounting for carbon isotope ratios are not available. Typically, atmospheric $CO_2$ concentration measurements obtained from ground stations and satellites are integrated with atmospheric circulation models to infer emissions from the land surface in a process referred to as tracer-transport inversion. This approach is inherently difficult using only $CO_2$ concentration data due to the high level of natural variation in $CO_2$ due to ecosystem carbon exchange, seasonality, and complex atmospheric circulation.

However, the isotopic composition of carbon emissions either as fossil fuel derived carbon or resulting from biogenic carbon flux can provide unique data representing a given area (e.g. spatial extent such as square meters, miles, etc.) and a given time period (e.g. temporal definition, daily, monthly, seasonal) of analysis. An ensemble of multi-isotopic analyzers distributed over a defined area is an important component of a system of systems that can provide data for unknown sources of $CO_2$ even with large natural variations of $CO_2$ concentrations. Concentration data for total $CO_2$, $^{13}CO_2$ and $^{14}CO_2$ directly measured in one or more locations are required but not sufficient alone to calculate carbon flux data that can be used for carbon trading and for carbon financial instruments. Typically, models are used in conjunction with data to interpret features of interest and, in the case of carbon trading, final results provided as metric tons carbon or metric ton of carbon equivalents for a defined geographic area, are required. It is widely recognized that due to the paucity of data for the isotopic composition of atmospheric $CO_2$ carbon budgets over a range of scales are limited in spatial and temporal resolution (Pacala et al., 2009; Tans et al., 1996).

However, even though it is widely acknowledged that models are severely limited due to a paucity of isotopic data, a system of systems to provide increased data rate for $^{13}C$ and $^{14}C$ is not available. Current model efforts utilizing the sparse data for $^{13}C$ and $^{14}C$ readily illustrate the limitations of models as needed for the rigorous and reliable accounting for carbon trading (e.g., Kosovic 2008). In addition the placement of $^{13}C$ and $^{14}C$ isotopic analyzers is dependent on a variety of factors including topography, vegetation cover, seasonality and wind patterns. Without a system of systems that can be deployed in the field under a variety of placement locations, strategic placement of isotopic sensors cannot be evaluated. Based on current data, the placement of isotopic analyzers should be such that additions of fossil and biogenic carbon to a given location or area of monitoring is within the detection limits of the analyzers. Thus, high precision, rapid and simultaneous analyses for $^{13}C$ and $^{14}C$ to promote effective measuring, monitoring, verification and accounting cannot be accomplished without a system of systems which is not currently available. Moreover, it is also clear that in order to measure, monitor, verify and account for anthropogenic carbon emissions, sampling stations and ensembles of analyzers should be placed in areas of large emissions, such as cities, specific industries and broad areas that might represent carbon emissions otherwise thought to be sequestered such as in the case of carbon capture and storage. The existing monitoring networks sponsored by a variety of governmental agencies are specifically not designed to measure carbon emissions from large local and regional sources. Such government sponsored sampling locations were chosen to detect natural sources and sinks over large scales such as across oceans and continents. Such data are not, therefore, suited to measure, monitor, verify and account for anthropogenic carbon emissions or serve as a basis for carbon credits (e.g., Vaughn et al., 2010).

Isotopic Mass Balance and Equivalency Relationships for Biogenic and Fossil Derived $CO_2$ in the Atmosphere The determination of one or both of the carbon isotopologues at a given location does not in itself provide sufficient data for determination of the total mass of carbon for either $^{13}C$ or $^{14}C$ that is ultimately desired for carbon trading based on metric tons of carbon. Simple numerical treatments for limited isotopic data are well represented in the scientific literature but are not adequate to meet the needs of carbon trading. Measurements of rare forms of carbon dioxide are provided relative to isotopic standards and are expressed as delta ratios according to the following formulas:

For $^{13}C$ isotope ratios: $\delta^{13}C(\text{per mil ‰}) = [(^{13/12}C \text{ sample}/^{13/12}C \text{ standard}) - 1] \times 1000$ For $^{14}C$ isotope ratios: $d14C(\text{per mil ‰}) = [^{14/12}C \text{ sample}/^{14/12}C \text{ standard}) - 1] \times 1000$.

However, it is widely acknowledged that due to limited spatial and temporal data for $^{13}C$ and $^{14}C$ for a given location or area, such data are too sparse to support the needs of carbon trading. In most simple terms, and as familiar with isotopic mass balance equations by those skilled in the art (e.g., Levin et al., 2003), one can estimate regional fossil fuel $CO_2$ from measured $^{14}CO_2$ and $CO_2$ concentration using the following mass balance equations:

$$CO_{2\ measured} = CO_{2\ biological} + CO_{2\ background} + CO_{2\ fossil\ fuel};\text{ and,}$$

$$CO_{2\ measured}(\delta^{14}C_{measured}+1000‰) = \\ CO_{2\ background}(\delta^{14}C_{background}+1000‰) + \\ CO_{2\ biological}(\delta^{14}C_{biological}+1000‰) + \\ CO_{2\ fossil\ fuel}(\delta^{14}C+1000‰)$$

In the above equations, $CO_2$ measured, is the observed $CO_2$ concentration from a given location or locations, $CO_2$ background, represents the concentration of $CO_2$ at a reference clean air site (e.g., Globalview 2006), $CO_2$ biological, is the regional biogenic component, and $CO_2$ fossil fuel, is the fossil fuel component for the region of the measurements. The $^{14}C/^{12}C$ ratios of these components in the delta notation are, respectively, delta $^{14}C$ measured, delta $^{14}C$ biological and delta $^{14}C$ fossil fuel. Delta $^{14}C$ is the per mil (‰) deviation from the $^{14}C/^{12}C$ ratio from the National Bureau of Standards (NBS) oxalic acid standard activity corrected for decay (Stuiver and Polach 1977).

Thus, solving for $CO_2$ fossil fuel yields the following equation:

$$CO_2 \text{fossil fuel} = [CO_{2\ background} \\ (\delta^{14}C_{background}\delta^{14}C_{biological}) - CO_{2\ measured} \\ (\delta^{14}C_{measured} - \delta^{14}C_{biological})]/\delta^{14}C_{biological} + 1000‰.$$

A similar set of equations can be constructed for $^{13}C$ ratios of atmospheric $CO_2$. In addition a number of models are known to those skilled in the art to calculate total carbon values from isotopic data over time and space, but are too data-limited to provide sufficient information to be used for carbon trading, as emphasized by Kosovic et al. (2008). Levin & Rodenbeck (2008) present data for $^{14}C$ measured by collection of air samples representing two locations and spanning a period from 1985 to 2006. Using an atmospheric transport model TM3 (Heimann 1996) Levin and Rodenbeck (2008) conclude that strong inter-annual variations in $^{14}C$ must be accounted for relative to changing trends in fossil fuel source emissions, and that high precision $^{14}C$ data from a large observational network is desired. Such an observational network is disclosed herein. Thus, despite a recognized need within the model community for vastly increased data for $^{14}C$ that is required to meet the measuring, monitoring, verification and accounting needs of the Kyoto Protocol, no such system of systems is in operation.

Likewise, the scientific literature presents many cases of isolated measurement of $^{13}C$ and $^{14}C$ and related models to elucidate carbon flux in a variety of settings such as forests (e.g., Urbanski et al. 2008; Uchida 2008), discrete locations (e.g., Lai et al. 2006; Graven et al. 2009) and for oceanic carbon flux (Randerson et al., 2002). However, these studies typically do not result in carbon data for purposes of carbon trading. Additionally, the many model approaches utilized do not offer a comparative basis of the results for geographically and widespread discrete locations.

The difficulty in providing a large number of isotopic analyzers situated in grids relevant to the area of interest and that produce comparative data with reference to well known standards is acknowledged by the absence of such systems. The difficulties are many, such as the inherent difficulty in field ready isotopic instrumentation, continuous data collection, landscape scale coverage by numerous instruments and a means to ensure comparative data from all instruments wherever they may be situated, and the like. Thus, such a system of systems accomplishing the aforementioned tasks would be highly desirable and needed to address the requirements presented by widespread carbon trading.

The difficulty in providing isotopic data for large scale models is even more demanding than providing data for limited models as described above. The end result required to yield carbon values in terms of metric tons carbon must be rigorously determined for a defined area and for a defined period of time representing a three dimensional framework. In essence, features of the atmosphere such as mixing and meteorological conditions must be matched to real time fluxes of the $^{13}C$ and $^{14}C$ isotopic species. For example, Peters et al. (2007) describe a large scale, three dimensional model approach for North America that combines daily $CO_2$ concentration from a set of 28,000 carbon mole fraction observations from diverse locations with an atmospheric transport model driven by meteorological fields and a $CO_2$ transport model (Peters et al., 2007). The model results are widely recognized as being highly valuable but does not meet the needs of carbon trading because, as discussed earlier, the $CO_2$ concentration data does not reveal the underlying carbon sources (e.g., fossil fuel $CO_2$ emissions versus biogenic $CO_2$ emissions). Indeed, this approach starkly illustrates the disparity between $CO_2$ concentration data and isotopic data.

As described earlier, approximately 100 locations are currently sampled for carbon isotopes with locations for the collection and analysis for $^{14}C$ being represented by about 25 locations. In addition, in most all cases the $^{13}C$ and $^{14}C$ analyses are not performed in real time, are not continuous, nor are they typically simultaneously determined on the same air sample introducing potential errors. Additional examples of appropriate models include the MM5 model (Grell et al., 1995) useful for atmospheric mesoscale meteorological applications, the LSM1 model (Bonan 1996) representing a large scale land surface model, the TAPM atmospheric model (Hurely et al, 2005) representing areas of hundreds of meters, and the bLs model (Flesch 2004) also utilized for atmospheric mapping over hundreds of meters. An example of the extent to which $^{13}C$ and $^{14}C$ analyses would be needed to determine fossil fuel emissions is provided by the work of Riley et al. (2008). In this work given the absence of $^{14}C$ analyses obtained by direct measurements of air samples, Riley et al. (2008) utilized plant samples as proxies for atmospheric $^{14}C$ representing plants from 128 sites throughout CA. The plant samples were analyzed for $^{14}C$ content using accelerator mass spectrometry. Riley et al. (2008) conclude from their measurements that flows of fossil fuel $CO_2$ from large sources in the State of California are predominantly to the south instead of the east as commonly assumed. Thus, this work provides clear indication of the importance of $^{14}CO_2$ measurements for state wide emissions regulations such as defined by California AB32 (ARB 2010) legislation and for development of larger regional emissions patterns. The use of plant samples by Riley et al. (2008) in lieu of analysis of whole air samples emphasizes the need for a vast increase of $^{14}CO_2$ measurements. However, as described above despite the recognized need for isotopic data of sufficient spatial and temporal coverage that could be used in a variety of models over many scales, the collection of isotopic data enabled by a system of systems to fulfill the model needs is not available.

Thus, a system of systems that could be placed in many locations (e.g., thousands) and for which simultaneous $^{13}C$ and $^{14}C$ measurements could be made continuously offering linkage with 3D models incorporating meteorological and landscape scale ecosystem data would be highly desirable and could provide a vastly improved understanding of carbon budgets for fossil fuel related emissions and biogenic carbon emissions and cycling at many scales ranging from point sources, to cities to states and to regions. Although the importance of such a system of systems is clearly recognized and long sought after, no such system exists due the inherent difficulties in the existing methods for measurement of isotope ratios and their use in frameworks suitable to enable carbon trading.

Laser Based Analysis of Carbon Isotopologues

Isotope ratios of $CO_2$ and other greenhouse gases of interest including $N_2O$ and $CH_4$ are traditionally measured by magnetic sector isotope ratio mass spectrometers (IRMS). These instruments employ a mechanical dual inlet system, require high vacuum and careful sample preparation of discrete, pure gases and offer precision on the order of 0.05 per mil for $^{13}C$ of $CO_2$ (Vaughn et al., 2010). However, magnetic sector devices are not suitable for in situ continuous flow analyses required for field measurements. The natural abundance of $^{13}C$ in the biosphere is approximately 1.1% relative to total carbon. In addition, the measurement of $^{14}C$ composition typically requires a radiometric analysis or an Accelerator Mass Spectrometer (AMS) facility that also relies on isotope specific ion counting as well as high vacuum and low sample throughput (Boaretto et al., 2002). The measurement of $^{14}C$ is technically more demanding as one skilled in the art recognizes due its low natural abundance at approximately $1\times10^{-12}$ relative to total $CO_2$. In both cases, traditional analytical schemes for $^{13}C$ and $^{14}C$ are difficult due to the ease with which isotopic fractionation can occur during gas manipulation from sample collection to sample analysis (Werner & Brand 2001) obscuring the original isotopic signal. Isotopic fractionation can occur due to changes in temperature, pressure, water vapor, instrument performance, instrument standards, and other internal factors that are often specific to individual laboratories.

The need for high precision for both $^{13}C$ and $^{14}C$ ratios is easily understood when considering that the global growth rate and seasonal isotopic variations are small in well mixed air consisting of approximately 1.9 ppm $CO_2$ and 0.025 per mil $^{13}/^{12}C$ (Vaughn et al., 2010). High precision $^{13}C$ isotope ratios can be made with a precision of +−0.01 per mil (1 std deviation) (Vaughn 2010) using traditional isotope ratio mass spectrometers. For $^{14}C$, a change of approximately 2 (e.g., 2.8) per mil represents approximately 1 ppm change in fossil fuel $CO_2$ (e.g., Riley et al., 2008). Thus, the current precision of approximately 2 per mil in $^{14}C$ measurements is sufficient to identify a 1 ppm change in fossil fuel $CO_2$. However, no analyzer is available that continuously and simultaneously analyzes $^{13}C$ and $^{14}C$ with the precision needed and that is field deployable. In addition, samples utilized for $^{13}C$ and $^{14}C$ analyses are consumed during analysis and cannot be re-analyzed a number of times, a shortcoming that limits precision obtainable through repeat analyses of the same sample and/or longer analysis times (Werner and Brand 2001). Thus, traditional high precision methods of analysis for $^{13}C$ and $^{14}C$ are not suited for field deployment and rapid analysis from an instrumentation perspective nor for coordinated use of large numbers of analyzers to support carbon pricing, trading and carbon management. Such a system is recognized as being highly valuable and long sought after and is not available.

Figure 3:
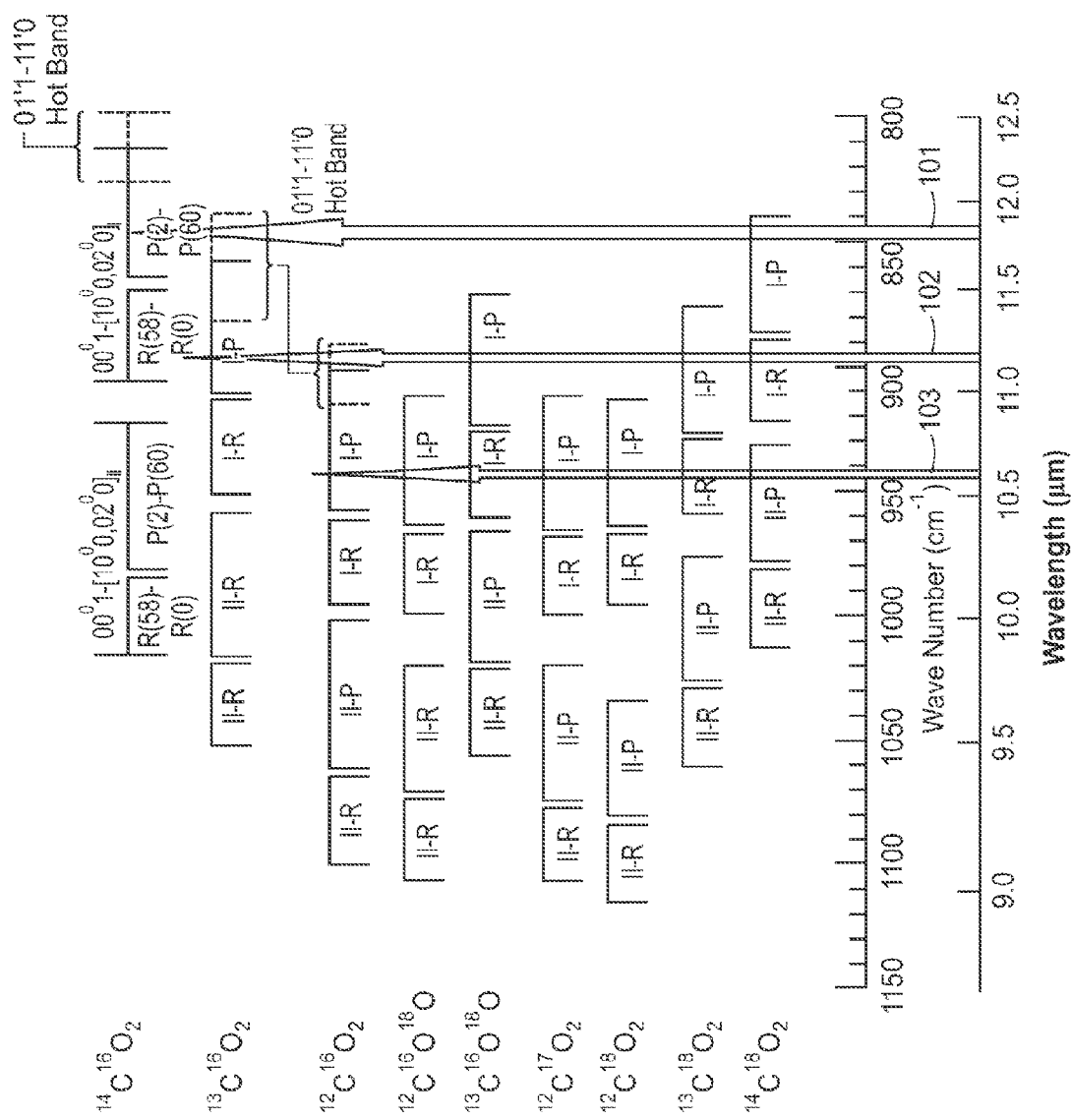
FIG. 3 is an illustration of the wavelengths of excitation for nine isotopologues of $CO_2$. The arrows represent the lasing transitions employed for determination of isotope ratios for $^{14}C^{16}O_2$ 101, $^{13}C^{16}O_2$ 102 and $^{12}C^{16}O_2$ 103.

One approach to avoid many of the shortcomings of isotope ratio mass spectrometry is the use of laser absorption spectroscopy. Laser absorption spectroscopy may also be used to quantify isotopologues of a number of gases including $CO_2$. Laser absorption spectroscopy was first applied to $CO_2$ in the early 1990's (Becker et al., 1992; Murnick and Peer 1994). Laser based approaches are possible due to specific excitation of vibrational-rotational transitions of gas molecules using finely tuned lasers. Thus, laser excitation of the rare species of $CO_2$, for example, can be used to probe and quantify the concentration of such molecules in a gas stream. FIG. 3 illustrates the frequency and wavelength domain of the relevant $CO_2$ isotopologues and the corresponding lasing transitions (Freed 1990). The arrows indicate selected lasing transitions for detection of the isotopologues of $^{14}CO_2$ 101 and $^{13}CO_2$ 102 and for the most abundant form of $CO_2$ ($^{12}CO_2$) 103. The use of laser based analyzers offers the option of employing sealed reference gas cells with standard gases that can be prepared in large quantities from air and additions of $CO_2$ based on high precision gravimetric gas preparation (e.g., Amico di Meane et al., 2009). Such sealed reference gas cells can be deployed in a large number of multi-isotopic analyzers and thus provide a foundation for comparisons between instruments as well as provide a high degree of stability and enable one key element of a system of systems. However, no such use of sealed reference gas cells is in use in a large number of strategically placed multi-isotopic analyzers. As can be appreciated by one skilled in the art of fabrication of sealed $CO_2$ lasers (e.g., LTG Lasers Ontario, Canada) such sealed reference gas cells are achievable in large numbers.

To date, a number of laser based devices have demonstrated successful measurement of the most common isotopologue of $CO_2$, namely $^{13}C^{16}O^{16}O$. Pulsed quantum cascade lasers have been reported to measure $^{13}CO_2$ with a precision of less than 0.1 ‰ with a 20 s averaging time (Tuzson et al., 2008) under ideal laboratory conditions. Cavity ring down laser spectroscopy disclosed by U.S. Pat. No. 7,154,595, published Dec. 26, 2006, and available commercially, reports precision of 0.3 ‰ using the Picarro G1101-I model employing a 10 s averaging time. Aerodyne Research Inc., Billerica, Mass., offers a pulsed quantum cascade laser offering a precision of 0.2 per mil using a 1 s averaging time. A laser based system utilizing a non-optical measurement approach, the opto-galvanic method, is disclosed in U.S. Pat. No. 5,394,236, published Feb. 28, 1995; U.S. Pat. No. 5,783,445, published Jul. 21, 1998; U.S. Pat. No. 5,818,580, published Oct. 6, 1998; U.S. Pat. No. 5,864,398, published Jan. 26, 1999, reporting $^{13}C$ precision of 0.1 ‰ with a 10 s averaging time. Thus, to one skilled in the art of laser spectroscopy, determination of $^{13}CO_2$ ratios is achievable with commercial devices, but are not currently capable of meeting the required precision (e.g., <0.1 per mil) and are not specific for $^{14}CO_2$.

Moreover, the systems described above, with the exception of the optogalvanic methods referenced, rely on an optical detection method of the excited $^{13}C$ isotopologue that is limited in accuracy and precision of such approaches. Specifically, the laser based devices for $^{13}C$ referenced above cannot detect $^{14}C$ due to limitations in detection given that the natural abundance of $^{14}C$ is $1\times10^{-10}$% in the atmosphere. The $^{13}C$ systems described above do not teach a method or approach to detect $^{14}C$ nor to combine a $^{14}C$ system with a $^{12}C$ and $^{13}C$ system. A multi-isotopic analyzer that simultaneously measures $^{13}C$, $^{14}C$ and $^{12}C$ is of obvious importance but is not currently available. In addition, such $^{13}C$ laser based systems that are available now are not deployed with a widely known and distributed $^{13}C$ sealed gas reference cell and are not linked within a system of systems and thus such analyzers operated alone cannot be used to determine carbon fluxes to support carbon trading and carbon financial instruments.

To date, there are no commercially available laser-based systems for the determination of $^{14}C$ in ambient air under continuous flow conditions. Only analyses of discrete air samples ranging from 500 cc to 3 liters (Vaughn et al., 2010) collected in evacuated flasks are utilized with conventional instrumentation. (e.g., Tans et al. 1996). However, a system disclosed in U.S. Pat. No. 7,616,305, published Nov. 10, 2009, and described in Murnick et al., 2008, offers a $^{14}C$ measurement technology. The teachings of U.S. Pat. No. 7,616,305 and of Murnick et al., (2009) are incorporated herein by reference and provide the basis for a feasible $^{14}C$ laboratory system. The system of Murnick disclosed in U.S. Pat. No. 7,616,305 represents a two cell system comprised of a specific laser for $^{14}CO_2$ and $^{12}CO_2$ but does not teach the analysis of $^{14}C$ of $CO_2$ in air but rather the analysis of $^{14}C$ in pure $CO_2$. A precision of approximately 1% (10 per mil) is reported. Murnick et al., (2009) does not teach use of calibration curves for small concentrations of $^{14}CO_2$ in air nor for a standardization with global reference materials, all of which would require specialized protocols and methods that are not obvious to the experimenter based on Murnick et al., 2008 due to complicated behavior of $^{14}CO_2$ and corresponding laser signal with varying concentration of $CO_2$. The difficulty in measuring $^{14}CO_2$ can be readily appreciated given that its natural abundance is approximately $1\times10^{-10}\%$ of all carbon in the atmosphere. Note that a three cell system comprised of $^{12}CO_2$, $^{13}CO_2$ and $^{14}CO_2$ lasers integrated in one system has not been described nor has the analysis of $^{14}CO_2$ in typical air samples been devised, a requirement for the use of said analyzers for analysis of atmospheric composition related to carbon and biogenic emissions.

In cases where both isotopologues ($^{13}C$, $^{14}C$) are determined the measurement of a sample does not ensure that the data obtained can be used for determination of tradable carbon credits. The determination of carbon credits according to biogenic or fossil fuel origin requires a number of analyzers with routine, repeatable and stable calibration, inter-calibration and global reference systems supported by instrument hardware, software and data analysis and synthesis. Thus, an instrument alone capable of measuring one or both isotopologues is not sufficient to reliably provide tradable carbon data. A system of systems approach as described herein is necessary to provide a spatial and temporal framework to collect, analyze, verify and transform carbon flux data into metric tons of $CO_2$ of fossil or biogenic origins over specified areas and over specific time periods. In addition, no method of standardizing reference material that could be used routinely for $^{13}C$ and $^{14}C$ laser based devices regardless of detection system is available. Thus, key components of a system of systems approach to support carbon trading are not available.

Calibration, Inter-Calibration and Global Standardization of Rare Forms of Carbon Typically, as described earlier, isotopologues of carbon are made by discrete measurements obtained by capturing air in an evacuated flask from a variety of locations and analyzed in a small number of laboratories at widespread locations. Such laboratories maintain internal standards and shared sets of standards for both isotopologues ($^{13}C$ and $^{14}C$) that in principal allow inter-comparisons and comparability of data from diverse locations. Such inter-comparisons are needed to construct temporal and spatial trends in isotopologues, however, differences in analytical procedures and preparation of standards in individual laboratories can introduce isotopic variation in accuracy and precision that may obfuscate trends in $^{13}C$ and $^{14}C$ of atmospheric $CO_2$ and require complicated corrections to data sets (e.g., Masarie et al., 2001; Werner and Brand 2001; Rozanski 1991; Vaughn et al., 2010). The conventional system of $^{13}C$ standards program currently could not support active trading of carbon due to the limited number of data and locations. Additionally, errors from each laboratory resulting from processing and analysis of the standards according to individual laboratory practices and according to type of analyzer propagate errors throughout the analyses and databases that result from such analyzers. The analysis of $^{13}C$ ratios by IRMS can be influenced by the presence of $^{17}O$ resulting in a potential shift of 0.03 per mil, and by the presence of $N_2O$ resulting in a shift of approximately 0.22 per mil (Vaughn et al., 2010). Inter-comparisons for $^{13}C$ data across laboratories has shown variance up to 10 times larger than the target precisions (Allison et al., 2002, 2003). Differences may be due to gas handling related to purification of $CO_2$, gas handling related to the analysis of $CO_2$ and/or to specific operation of a variety of isotope ratio mass spectrometers. Thus, standards that are used internally or those that are shared do not provide a rigorous cross instrument comparison, a requirement if data from one or more instruments located in a variety of locations is needed. Thus a system of systems that offers instantaneous measurement of $^{13}C$ by a number of widely located analyzers and that are directly and instantaneously comparable to shared standards would be highly desirable in monitoring, verifying and accounting for variations in $^{13}C$. However despite the long term goal of such a network of high precision and comparable $^{13}C$ and the importance of such a network no such system of systems is available. Such a system of systems would be needed to measure, monitor, verify and account for biogenic carbon as distinguished from fossil fuel carbon for the purposes of carbon trading as related to biogenic carbon flux (e.g., forest carbon sequestration) and for such data requirements for the incorporation of $^{13}C$ data in appropriate models of ecosystems and of meteorological models needed to calculate carbon mass as a function of time and space.

The case for $^{14}C$ standards and inter-calibration are more demanding as smaller samples and more complex instrumentation are required as $^{14}C$ abundance is vastly smaller than that for $^{13}C$ as described above (e.g., 1.1% $^{13}C$ vs. $10^{-10}\%$ $^{14}C$) Samples as small as 0.5 mg total carbon are analyzed in large complex Accelerator Mass Spectrometers and requirements for standards of varying $^{14}C$ composition are difficult to maintain free of $^{14}C$ contamination (Stork et al., 1997). Due to the difficulty and expense in analyzing $^{14}CO_2$ and maintaining an AMS facility a small number of such AMS facilities are available for high precision analyses (e.g., Boaretto et al., 2002). In cases where standards are required that span 0% $^{14}C$, as is the case for fossil fuel $CO_2$ to increasing fractions of modern $^{14}C$ the technical demand in handling gases properly to ensure that no fractionation takes place is very high and to-date has not been introduced into a system of systems as described herein. Isotopic differences can also be related to fractionation during sample concentration (e.g., cryogenic isolation of $CO_2$), gas manipulation, and conversion to graphite and analysis (Werner and Brand 2001). An instrumental method that allows for analysis of $^{14}C$ of both the unknown and a standard reference gas that does not involve sample concentration and manipulation as described above for AMS measurements and that is readily referenced by a large number of related instruments would be highly desirable and of obvious importance, but is not currently available. Thus, as is the case for $^{13}$C, an instrument alone that is capable of measuring $^{14}$C composition of an air sample is not sufficient to support carbon trading and carbon financial instruments. In addition to the difficulty of analyzing $^{14}$C samples using the AMS method large numbers of samples are generally prohibitive due to the high cost per sample ranging from $400 to $600 per sample. A $^{14}$C continuous field analyzer would offer thousands of measurements for a considerably lower cost and in a fraction of the time required for AMS analyses.

The historical data for $^{13}$C and $^{14}$C standardization, all provided by stationary instruments at widespread locations show clear and persistent problems in maintaining worldwide networks of comparable standards, in part due to the expense and expertise required for analysis of the rare forms of carbon Thus, employing such a network based on traditional isotopic analysis and the intrinsic errors in these systems for both $^{13}$C and $^{14}$C for the purposes of carbon trading have not and cannot be assembled due to the high costs, limitations of the instrument networks, instrumentation and the methods used to analyze and maintain standards that can be globally compared. Thus, despite the recognized need and value of such a system, no such system of systems currently exists to support carbon trading and related carbon financial instruments.

As noted above, to date, no experimental or commercial system currently exists that combines systems for measuring and monitoring both $^{13}$C and $^{14}$C in one instrument. Specifically, WO99/42814 does not address a systems of systems incorporating multiple analyzers linked by shared standards and global reference standards that are then used to compute carbon in terms of tradable units such as metric tons C for both biogenic and fossil carbon fluxes. It is further noted that the art of $^{14}$C analyses using laser based methods were not described in sufficient detail to allow one skilled in the art to build such analyzer. The low concentration of $^{14}CO_2$ in the atmosphere being $10^{-10}$% of total $CO_2$ has not been accounted for in WO 99/42814 with respect to methods to analyze such small quantities being a factor of $10^{-9}$ in natural abundance versus $^{13}$C. WO 99/42814 makes reference to U.S. Pat. No. 5,394,236. However, such reference relates to a laser-based device for determination of $^{13}$C and is not applicable to $^{14}$C determinations. $^{13}$C is present at about 1.1% in total $CO_2$ offering readily available options for its analysis. Thus, WO 99/42814 did not have possession of said $^{14}$C analyzer. Further, such $^{13}$C and $^{14}$C analyzers were not employed in a system of systems utilizing integrated components that result in carbon tradable units. WO 99/42814 primarily teaches the combined analysis of $^{13}$C and $^{14}$C but does not extend beyond the analysis stage. As we describe below $^{13}$C and $^{14}$C isotope ratios alone are not sufficient to produce carbon credits for trading on carbon financial platforms.

Importantly, despite the long felt need, it has been realized that implementation of the system described in WO 99/42814 as an actual or commercial system has been especially difficult as different criteria arises based on the different applications. For example, teachings of WO 99/42814 could not be carried out to measure and monitor carbon flux in ocean water as carbon gases had to be stripped from the water, which was neither described nor suggested. Other applications, such as measuring and monitoring carbon in a forest, agricultural area, soil, and the like, prove difficult as proper data sampling rate coupled with the proper spatial density of measurement is neither described nor suggest and was not readily recognizable.

Carbon Trading

Carbon Trading and Carbon Financial Instruments

Currently, carbon based financial instruments are centered on standard units for carbon as expressed in metric tons (1.1 short ton) of $CO_2$-equivalence (mtCO$_2$e) (IPCC 2008). However, direct measurements of the flux of $CO_2$ expressed as metric tons are lacking. In addition, data for carbon expressed in metric tons are used to establish carbon offsets in cases where an offset is generated by the reduction, avoidance or sequestration of greenhouse gas (GHG) emissions achieved by a given project. However, direct measurements confirming the actual number of mtCO$_2$e emissions produced, or confirming by direct measurement the absence of emissions in cases of reduced or avoided emissions (in the case of offsets) are lacking. Estimation of $CO_2$ emissions is used based on fuel consumption (and/or reduction from prior levels) at a given location or number of locations including a trading group, such as the European Union Emission Trading Scheme (IPCC 2008). Thus, in the absence of actual measurements, uncertainty is unknown, representing a fatal problem in the method of quantification of emissions; small source term errors propagate and magnify downstream process errors such as pricing of carbon based financial instruments and their derivatives. Uncertainty reduction can only be achieved by high precision measurements across the landscape of a region or trading area. Currently, there are no such regional measurement stations employing multi-isotopic devices for the rare forms of carbon to be used in the reduction of uncertainty for carbon based financial instruments. Thus, it would be highly desirable to employ a broad-based multi-geographic system to measure, report and verify carbon emissions (reductions of emissions) that are comparable across a trading landscape as large as continents for $CO_2$ and related greenhouse gases. No such system currently is available to reduce uncertainty in carbon-based instruments.

Likewise, existing carbon exchanges, domestic and international, (e.g., Chicago Climate Exchange (CCX), www.chicagoclimatex.com; European Emission Trading System (EUETS), www.ec.eurpa.ed)) do not specify biogenic or fossil forms of carbon data nor direct measurement that are required to support carbon-based financial instruments. The CCX issues tradable Carbon Financial Instrument® (CFI®) contracts to owners or aggregators of eligible projects on the basis of estimated sequestration, destruction or reduction of GHG emissions. All CCX offsets are issued on a retrospective basis, with the CFI vintage applying to the program year in which the GHG reduction took place. Projects must undergo third party verification by a CCX approved verifier. All verification reports are then inspected for completeness by the Financial Industry Regulatory Authority (FINRA, formerly NASD). Offset projects can be registered by Members, Offset Providers and Offset Aggregators. Entities that have significant GHG emissions are eligible to submit offset project proposals only if they have committed to reduce their own emissions to the CCX Emission Reduction Schedule as MembersCCX has developed standardized rules for issuing CFI contracts for the following types of projects including methane (agricultural, coal mine, landfill), soil carbon (agricultural, rangeland management), forestry, renewable energy and ozone depleting substance destruction. However, in all cases of carbon emissions/reduction, direct measurements of the emissions offsets for $CO_2$ are not employed by the CCX or third party verifiers either as total $CO_2$ or as the relevant isotopologues of $CO_2$ (e.g., $^{13}C$, $^{14}C$) (CCX, www.ccx.com). The lack of measurement introduces uncertainty and errors of unknown magnitude, a complication that can affect carbon pricing, market dynamics and facilitate fraud.

In the case of soil carbon, CCX criteria are provided as standard offsets for $CO_2$ on a per acre basis depending on geographic location. For example, soil carbon offsets are issued on a per acre per year basis (CCX, www.ccx.com). The offset issuance rate depends on the region in which the practice is being undertaken. For instance, enrolled producers in Illinois may be issued offsets at a rate of 0.6 metric tons of $CO_2$ per acre per year and producers in central Kansas may be issued offsets at a rate of 0.4 metric tons $CO_2$ per acre per year. The different offset issuance rates are taken to reflect the differing carbon sequestration capacity of the soils in any given location. Thus, estimates are placed on carbon sequestration for land areas without actual measurement. To one skilled in the art of carbon soil and ecosystem dynamics, such a method is flawed and likely propagates substantial errors in estimation of carbon sequestered. Data from instrumented towers located in forests, for example, clearly show wide variations in net carbon flux from year to year and strongly suggest that simple algorithms for hypothetical forests and other land-based ecosystems are likely to be in error (e.g., Urbankski et al., 2007). Likewise, all listed offset projects by the CCX do not specify measuring, monitoring, reporting or verification methods in detail and do not require estimation of errors of assessments. Thus, the CCX as with all major carbon exchanges does not set the standards for actual and direct measuring, monitoring, reporting and verification. These tasks are left to third party verifiers that use a wide range of estimation programs. Stable isotopes are not used for verification purposes and, further, are not linked to a set of international global standards that allows for comparison of carbon flux from different regions of a state, a group of states of from different continents. Thus, current carbon markets are not based on instrumental measurement, standards and global reference systems that are required to capture data, reference signals and spatial and temporal coverage over designated trading regions, but rather estimation with unknown uncertainty. Thus a system of system that corrected the deficiencies listed above would be highly desirable, but is not available.

Existing Use of $^{14}C$ in Standard ASTM Methods $^{14}C$ ratios on solids and gases produced by combustion of solids using traditional scintillation counting methods and Accelerator Mass Spectrometry (AMS) are used in the context of ASTM D-6866 (ASTM 2008) to establish bio-based content of fuels and flue gases that are produced with varying amounts of bio-based source materials, primarily plant biomass (see FIG. 2, biodiesel blends). The gas stream analysis is based on discrete samples of gas collected in evacuated flasks and are not used to assess wide scale fossil fuel contributions but to verify point source emissions for bio-based content relative to specifications. The % biogenic based material and resulting $CO_2$ are designated as carbon neutral and thus does not count towards the carbon emissions cap for a specific industry (Hämäläinen et al. 2007). Specifically, data for $^{13}C$ and $^{14}C$ based on current methodology does not incorporate continuous analysis or linked standards for $^{13}C$ and $^{14}C$ measured together such that measurements are intercomparable wherever they may be made and such that measurements can uniformly and accurately be used to establish carbon trading units and to establish the basis for carbon financial instruments. Thus, the measurement of $^{14}C$ using multi-isotopic analyzers as disclosed herein provides a fundamental advancement over existing single sample analysis for $^{14}C$ as well as expands the value of multi-isotopic analysis as described previously. The use of the ASTM D-6866 provides a fundamental methodology that will be vastly expanded by the teachings disclosed herein.

Thus, based on the descriptions provided in the previous sections it is clear that instrumentation, standards and references and systems level reporting and referencing are not available that specify an equivalency relationship between concentrations of isotopologues in the atmosphere and monetization of emissions or sinks for the purposes of carbon trading and the reduction in uncertainty of errors in the units of carbon traded. Accordingly, a need remains for a means of distinguishing between and quantifying carbon budget components, and a means to inter-compare data across time and spatial scales as well as reference all measurements within a global reference system required for planetary carbon management and carbon trading. Such a system of systems, however, is not currently available based on the efforts of those skilled in the art of isotopic analysis.

An additional approach to quantify carbon emissions is based on space borne measurements of $CO_2$ using a variety of spectrometers. Satellite campaigns such as the Orbital Carbon Observatory (OCO), Greenhouse gas Observing Satellite (GOSAT) and the Atmospheric Infrared Sounder (AIRS) provide diverse measurements of $CO_2$ and other greenhouse gas measurements (Pacala et al., 2009). Each satellite has specific remote sensing capabilities and offer promise to measure fossil fuel emissions. However, satellite approaches cover a small sensor path and area as it travels in space over the Earth. While satellites are highly desirable for greenhouse gas measuring and monitoring, such data cannot support a detailed inventory of emissions to be used for carbon trading according to the requirements for any given location, area and over a given period of time since the satellite is moving according to the pathway designated rather than manipulation of pathways to specific sites with stationary data collection. Moreover, the cost of satellite systems are high and may return a limited number of years of observations requiring launching of new satellites (Pacala et al., 2009). However, a combination of satellite sensor data and ground based observations, such as those from an array of multi-isotopic analyzers with inter-calibration, reference protocols and appropriate models to ensure that data from fossil $CO_2$ emissions are credible would be highly desirable.

An arrangement in which a satellite with $CO_2$ sensors passes over an array or a ensemble of multi-isotopic analyzers allowing cross comparison of ground with satellite data would be highly desirable and of great value in providing additional third party verification for measurement of $CO_2$ emissions. Further, a ground based and satellite integrated measuring program may also offer an additional master reference sealed cell signal to directly compare ground based standard gases in sealed reference cells to a set of such cells carried as part of the satellite payload. Thus, one can ensure that an inter-comparison between satellite on-board carbon sensors and ground based carbon isotopic data are valid. Thus, while integrated ground based and satellite based programs would be highly valuable and recognized as such by those skilled in the art of space based $CO_2$ measurement systems, no such integrated systems are available.

Various embodiments of a system of systems described herein address these difficulties, and provides a new approach that is singular in its application compared to existing technology.

Certain embodiments provide a system allowing for collecting concentration and isotopic data, such as for atmospheric $CO_2$ isotopologues including $^{13}C$, $^{14}C$ and $^{12}C$, from a diverse spatial array of devices that report data in real-time based on shared calibration routines, shared primary and master reference data and routines and that analyze data, combining such data with diverse model approaches to reveal carbon mass for given spatial and temporal project areas. Such derived carbon mass are rendered as metric tons carbon or equivalents and used by financial institutions for carbon trading and/or to guide policy makers. The reporting of data for carbon trading can occur with high frequency enabling real-time financial transactions or with lower frequency and time period averages useful for discontinuous carbon financial transactions. In certain embodiments, a system disclosed herein allows for simultaneous measurement of multi-isotopic species in ambient air, such that source(sink) terms are identifiable, quantifiable and recognized as isotopic equivalents to standard $CO_2$ emissions and offset units, such as a metric ton of carbon or a metric ton of carbon equivalents. The system of systems approach disclosed herein makes use of sealed reference cells being identical and deployed in all analyzers in a given area providing for comparable carbon data across all analyzer locations and time periods of data collection. The importance of this capability can be appreciated by considering the difficulty in constructing carbon budgets without information about the component sources as is evident in current carbon trading mechanisms and approaches that are based on estimation rather than actual measurement.

System of Systems

Figure 4:
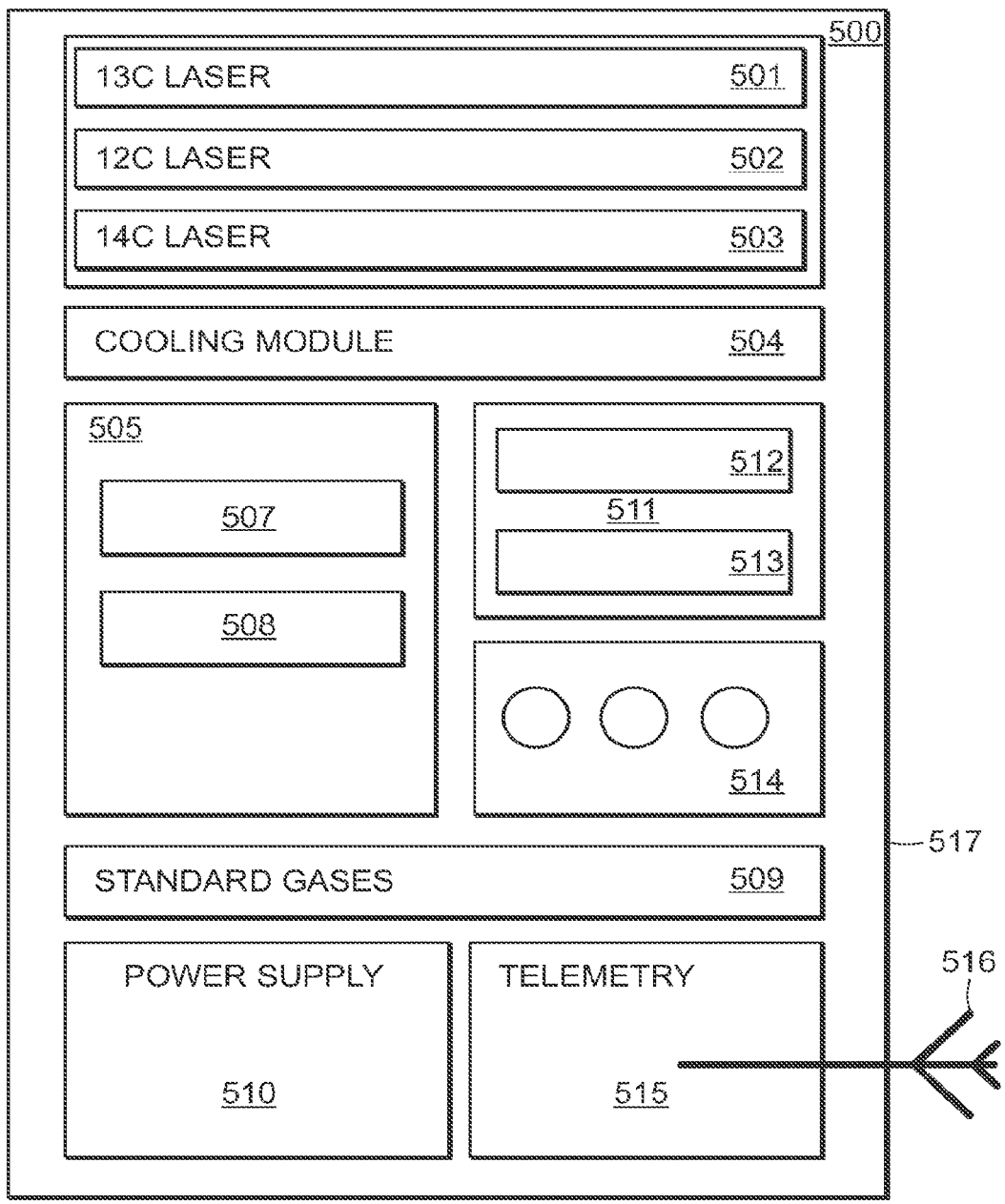
FIG. 4 is a block diagram representing modules of a system according to certain embodiments.

Certain embodiments provide a system of systems for simultaneously maintaining and reporting data on multiple isotopologues. FIG. 4 illustrates a block diagram of the instrument package as a component of a system of systems according to an embodiment. The apparatus includes an all weather housing 517, an optics module 500, housing one or more lasers for each isotopologue including but not limited to a $^{13}C$ laser module 501, a $^{12}C$ laser module 502, and a $^{14}C$ laser module 503, a cooling module 504, a sample module 505, containing one or more sealed reference cells 507 for each isotopologue and one or more sample cells 508, a standard reference gas module 509, a power module 510, a cpu and telemetry module 515 with telemetry antenna 516, a sample pre-conditioning module 511 containing one or more water removal units 512 and one or more particulate removal units 513, and a module serving as a platform for additional sensors 514 as desired to complement isotopic data.

Figure 5:
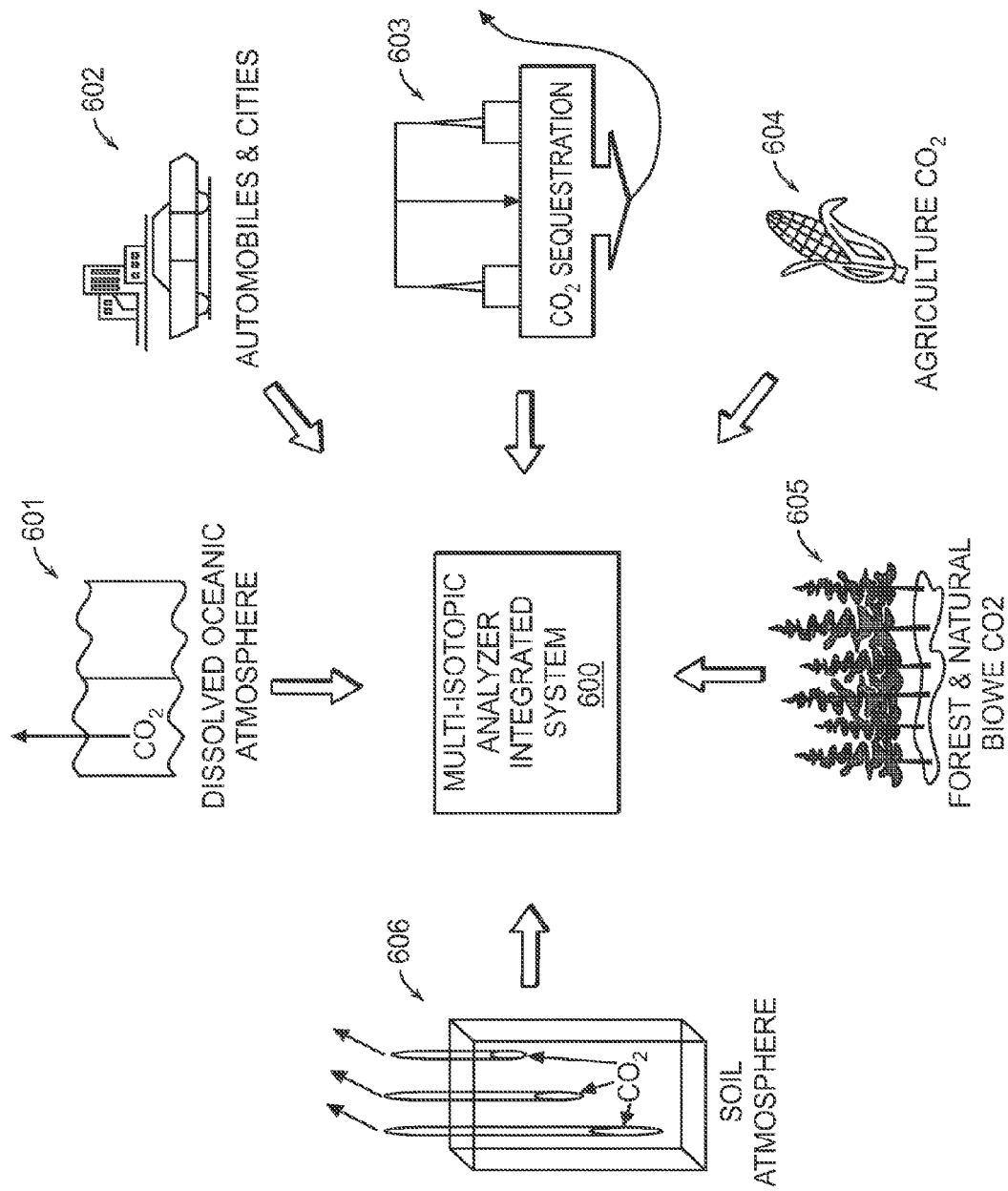
FIG. 5 is an illustration of the typical environments in which isotopic analyses can be carried out for the purposes of quantifying carbon emissions from the dominant sources for the gas to be used for carbon trading.

FIG. 5 illustrates a diagram summarizing exemplary system of systems analysis locations of the instrument package shown in FIG. 4. Typical locations as described are examples and do not preclude other sample locations. The multi-isotopic analyzer 600 can be employed in a variety of locations including on the ocean surface to extract dissolved oceanic gases 601, such as $CO_2$, dissolved in seawater or other bodies of water that may be extracted in situ and admitted to the apparatus, within a city for city-scale measuring and monitoring of industrial (coal, natural gas) and automobile $CO_2$ emissions 602, sampling within the soil atmosphere or on the surface of a soil 606 at vulnerable locations on the planet such as high latitude soils with high carbon content where large scale sampling of the soil atmosphere could be used as an "early warning" system for soil carbon release in response to surface warming of high latitudes, within natural forested areas of the world 605 where large amounts of carbon are tied up in soil, woody and leaf biomass representing either very large potential sinks or sources of $CO_2$ related to global warming and forest management, within agricultural settings 604 to measure carbon flux of agricultural fields that may also serve as source or sink depending on agricultural methods, watering regime and application of fertilizers, and within flue gas from power plant stacks and related $CO_2$ sequestration projects 603 where leakage of fossil fuels from storage locations is key to effective management and development of storage processes.

Figure 6:
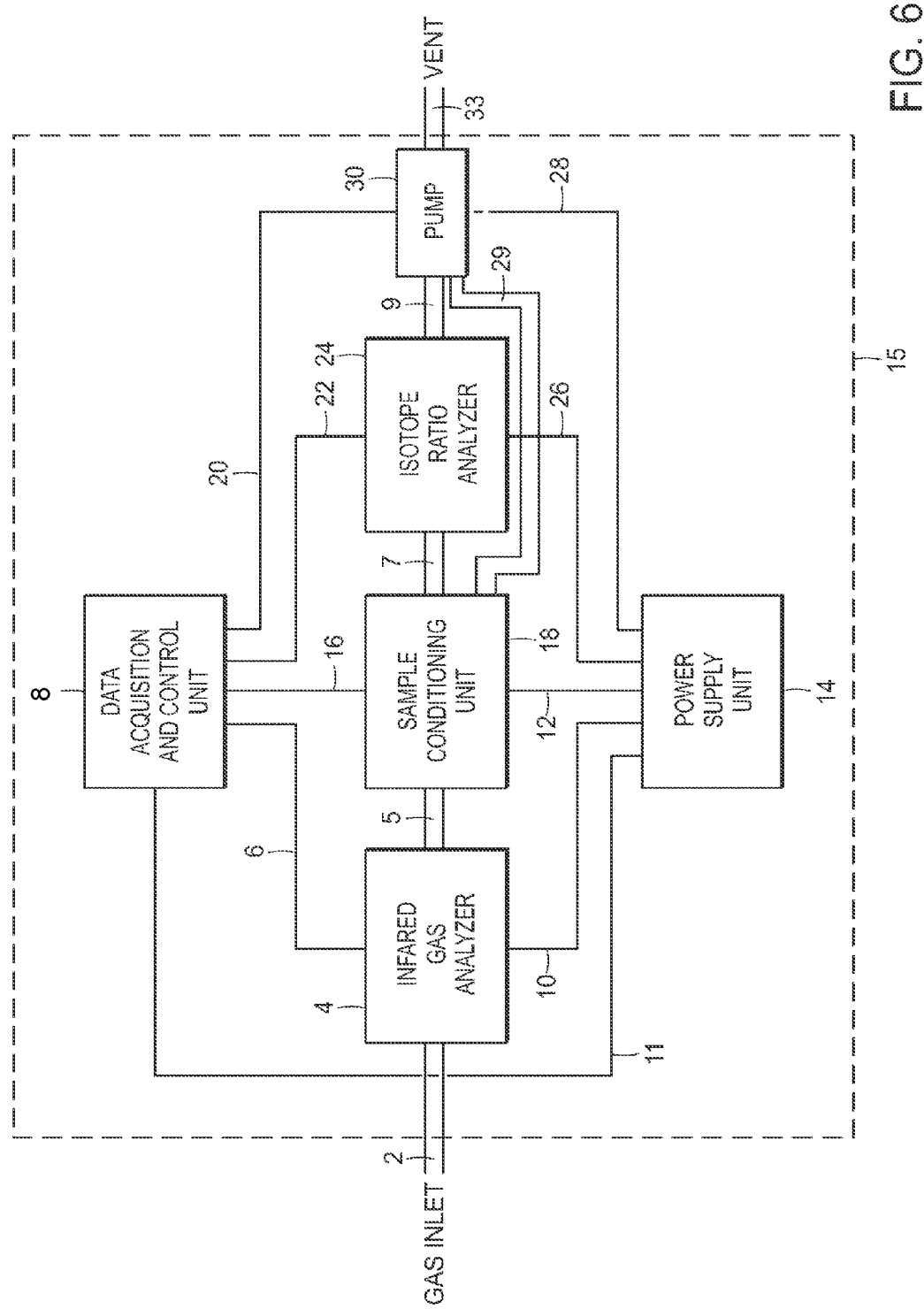
FIG. 6 is a summary block diagram of an apparatus according to certain embodiments. The following reference numerals will be used in FIGS. 6 through 11.
2 gas-tight inlet tube
4 infrared gas analyzer
5 gas-tight coupling tube
6 electrical connection
7 gas-tight coupling tube
8 microprocessor-based data acquisition unit
9 gas-tight coupling tube
10 electrical connection
11 electrical connection
12 electrical connection
14 self contained power supply unit
15 weather hardened container
16 electrical connection
18 sample conditioning unit
20 electrical connection
22 electrical connection
24 isotope ratio analyzer
26 electrical connection
28 electrical connection
29 coupling tube
30 diaphragm pump
33 vent tube
34 gas inlet tube
36 oxygen scrubber
38 gas outlet tube
40 gas inlet tube
42 gas-tight gas chamber
44 gas-tight coupling tube
46 gas selective membrane
48 gas-tight coupling tube tee
50 pure nitrogen source
52 gas-tight coupling
54 flow controlling valve
56 gas outlet tube
58 gas-tight coupling tube
60 vacuum compatible solenoid valve
62 gas-tight coupling tube
64 gas-tight inlet tube
66 vacuum compatible solenoid valve
68 gas-tight coupling tube tee
70 gas-tight coupling tube
72 solenoid valve
74 pure nitrogen source
76 four-port, two position flow switching valve
78 coupling tube
80 coupling tube
82 cryogenic trap
84 gas outlet tube
86 coupling tube
88 stainless steel lid
90 disc
92 gas-tight electrical feed-through
94 open end of U tube
98 open end of U tube
100 stainless steel vent tube
102 solenoid valve
104 gas exhaust tube
106 fiberglass-insulated resistance heating wire
108 stainless steel "U" tube
110 stainless steel cylinder
112 liquid nitrogen dewar
113 sample chamber for unknown measurement (ZnSe windows)
114 carrier gas cylinder or generator
115 stainless steel expandable bellows
116 sample inlet
117 capillary tubing to regulate gas flow into the sample cell

Referring to FIG. 6, in summary a typical system utilizes a pump 30 to draw the sample gas mixture into the system 2. The sample is next passed through a detector to measure the overall concentration of the desired species in question 4. The overall concentration of the desired species can be measured via an infrared gas analyzer 4 or in any other fashion appropriate to the configuration and species being measured.

The sample is then optionally passed through a preconditioner 7. The preconditioner performs one or more of the following operations: particle removal to clean the sample of particulate, component removal to remove one or more component gases from the sample (i.e., components that may interfere with later processing and detection), concentration of the desired species, and addition of a carrier to facilitate processing. In particularly harsh environments, particle filtration may be applied at an earlier position in the sample path.

Still referring to FIG. 6, the system passes the sample to one or more isotope ratio analyzers 24. The analyzer detects the concentration of a predetermined isotope of the desired species. The analyzer may be any conventional isotope analyzer. Some embodiments employ a small and accurate laser based unit. For instance, a laser tuned to emit radiation at a wavelength appropriate for the predetermined isotope of the desired species can be used to excite the isotope species into an excited state (see FIG. 3). Simultaneously, the laser excites a known standard of the isotope species. Any suitable type of detector, such as a photodiode detector or an optogalvanic detector can be used to measure the level of excitation of both the sample and the standard and thus detect the concentration of the isotope. The isotope ratio is calculated by comparing the isotopic species concentration to the total species concentration measured earlier in the path.

Figure 9:
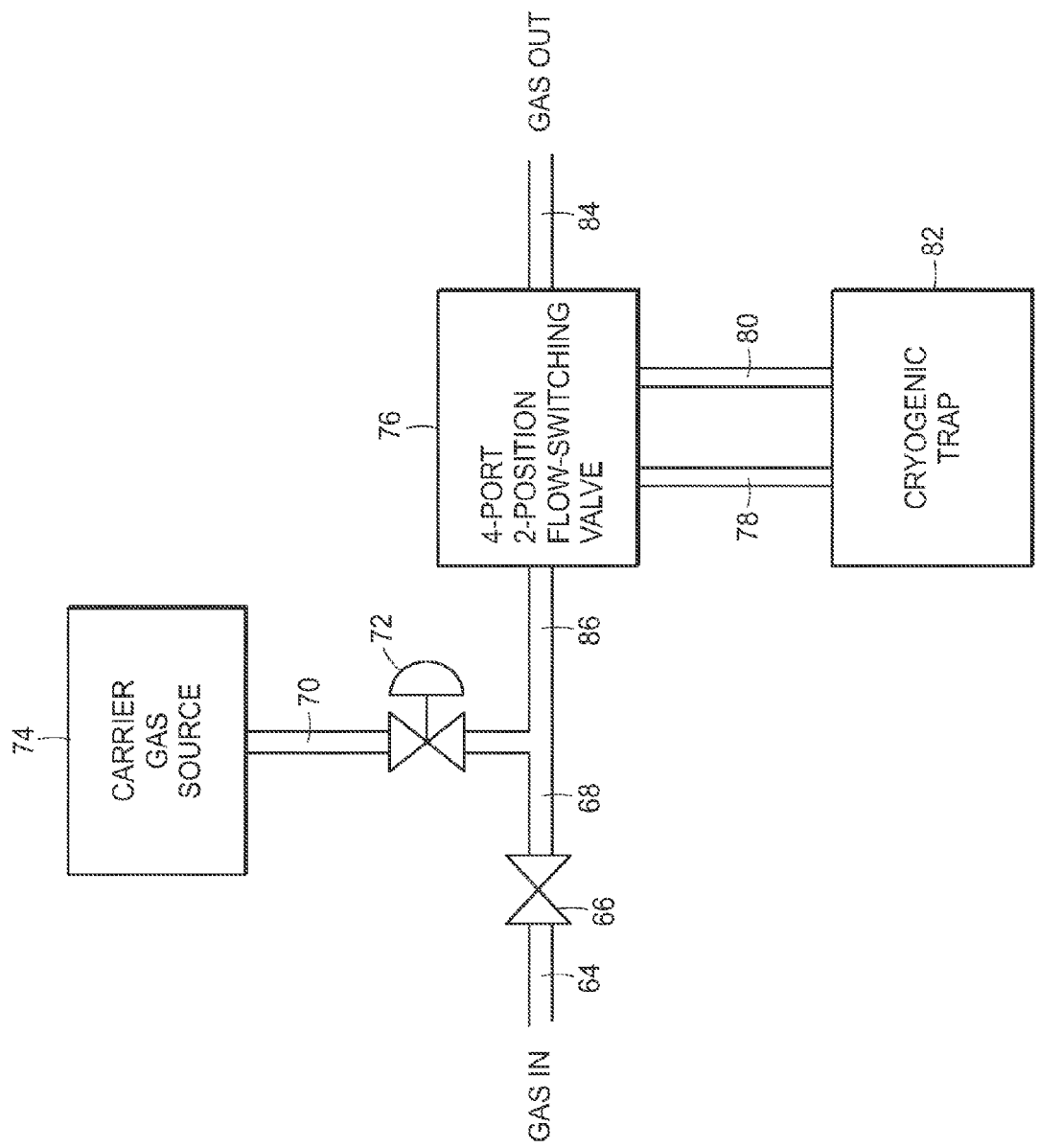
FIG. 9 is a block diagram of an embodiment of a sample conditioning unit as incorporated in the apparatus of FIG. 6, such sample conditioning unit utilizing a cryogenic trap.
Figure 10:
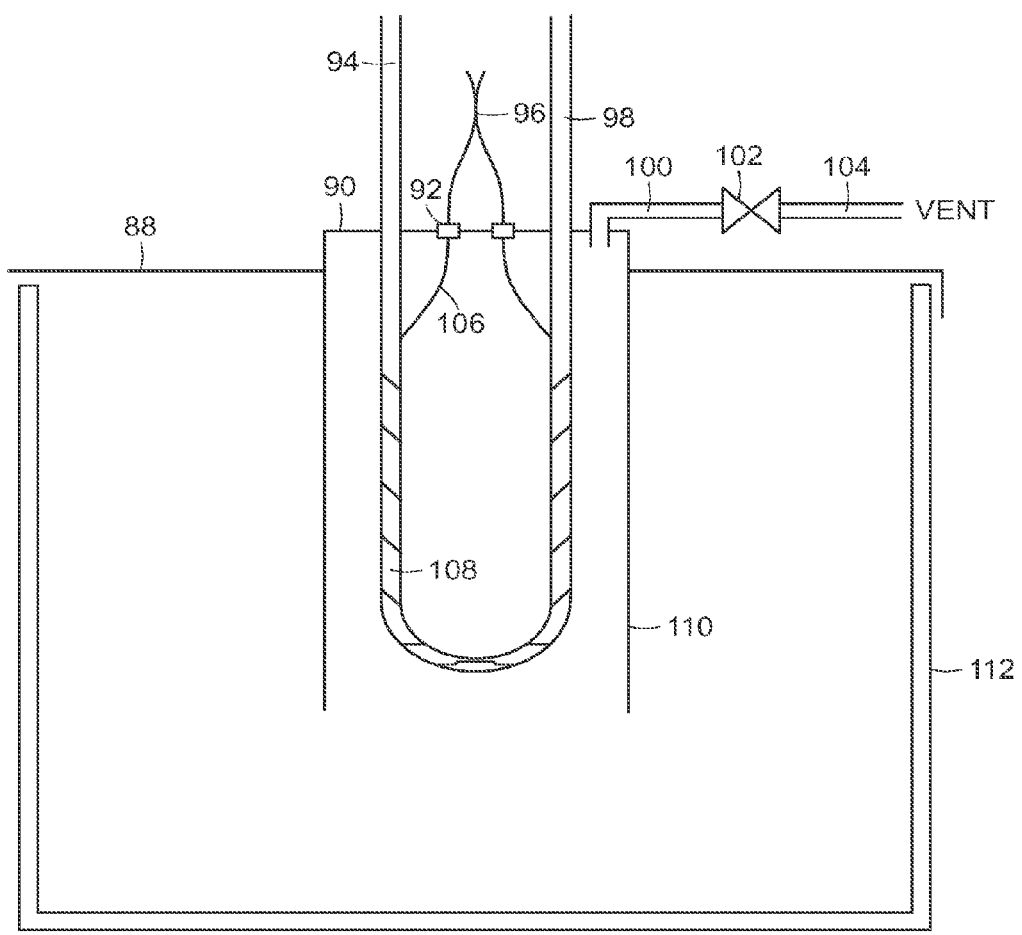
FIG. 10 is a schematic cross-sectional view of an embodiment of a cryogenic trap as incorporated in the sample conditioning unit of FIG. 8.
Figure 11:
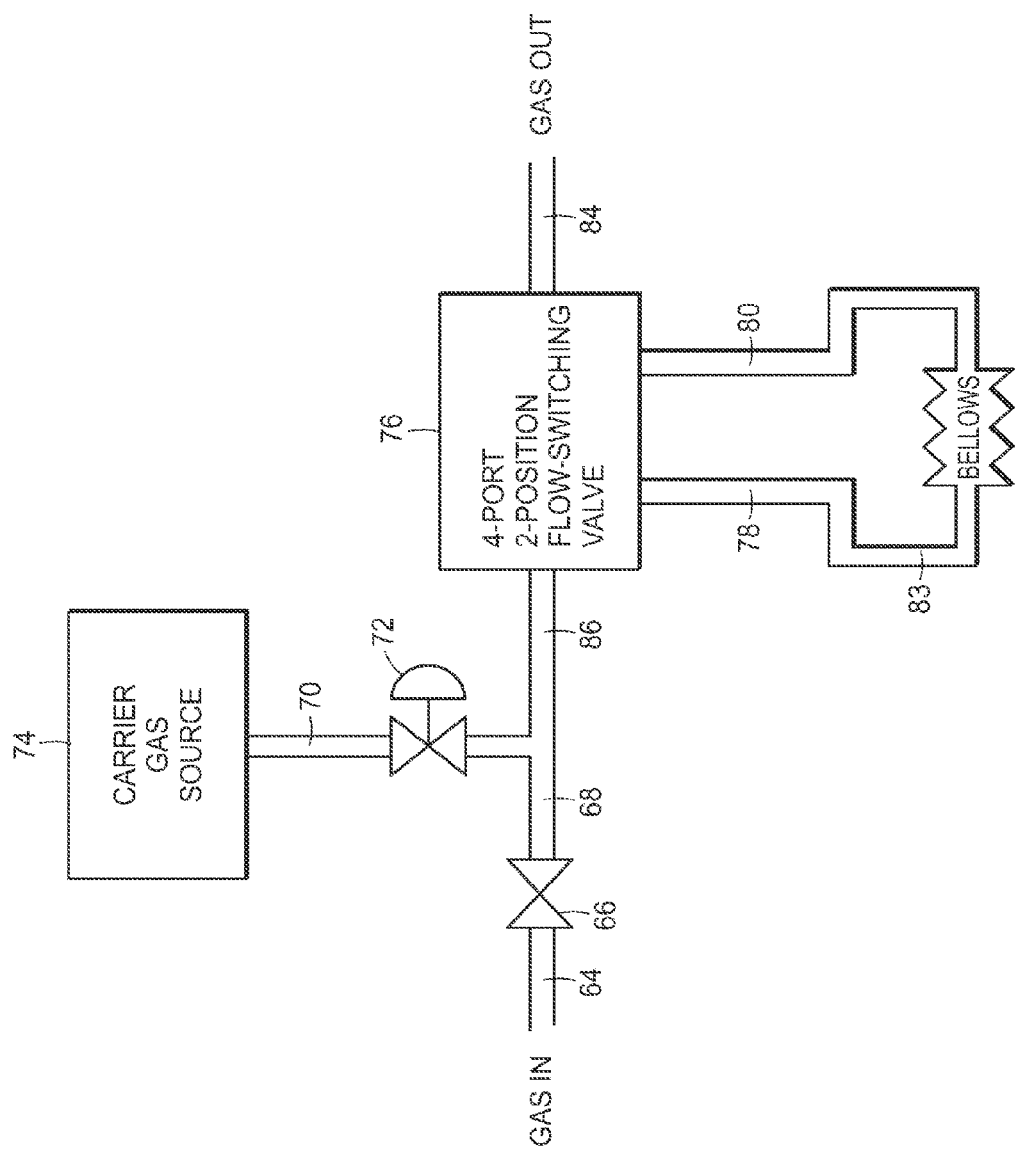
FIG. 11 is a block diagram of an embodiment of a sample conditioning unit as incorporated in the apparatus of FIG. 6, such sample conditioning unit utilizing an appropriate source of carrier gas, such as nitrogen, to provide for dilution of a given sample to increase the accuracy and precision for measurement of $^{13}C$ and $^{14}C$ in a sample.

In some embodiments, one or more detectors, preconditioners and isotope analyzers are combined, allowing the simultaneous measurement of multiple isotope ratios within the sample. They may be configured in a variety of system architectures, with some units operated serially and others operated in parallel. Referring to FIG. 7 one type of preconditioner module 36 may be employed to scrub oxygen from the inlet airstream 34 such as available from Teledyne Instruments, model TAI $O_2$ scrubber, containing copper oxide and aluminum oxide rendering an oxygen free gas 38. Referring to FIG. 8 a gas selective membrane 46 such as that sold by the name of Nafion can be used to remove water vapor from an inlet gas stream 40 that can subsequently be mixed with carrier gas 50 and exiting as gas 56 for analysis. Referring to FIG. 9, a cryogenic trap 82 may be used to concentrate $CO_2$ in some embodiments taking inlet gas 64, mixing as needed with carrier gas 74 and then flowing to trap 82 where liquid nitrogen is introduced to the trap with gas flow operated by a 4 port 2-position flow switching valve 76. Subsequent to trap operation concentrated gas is directed to the gas outlet 84 for analysis. Referring to FIG. 10, the cryogenic trap is composed of stainless steel tubing 94 and is heated after trapping with a resistance wire heater 106. The trap is positioned in a dewar 112 to receive liquid nitrogen for the freezing cycle of the trap operation. Referring to FIG. 11, a stainless steel bellows 83 is used to decrease the concentration of inlet sample gas 64 in cases where the concentration is too high for effective and accurate analysis as measured by a gas concentration analyzer 4 (FIG. 6). The inlet sample is admitted to the bellows in a closed position or compressed position and valves 78 and 80 are closed. Subsequently, the bellows is expanded and carrier gas 74 is admitted allowing the target concentration to be obtained by dilution as determined by gas analyzer 4. Subsequently the gas is allowed to flow to the isotope ratio analyzer 24 via a capillary flow or other means.

In some embodiments, here referring to FIG. 6, the system is controlled by a microprocessor-based data acquisition and control unit 8, such as a personal computer. The data acquisition and control unit controls the operation of each portion of the system, collects measurements, performs data processing and data summary, stores the data and transmits the data. The data acquisition and control unit may also be connected to external sensors so as to measure and monitor conditions external to the system (e.g., weather conditions such as temperature, wind direction, wind speed, pressure and humidity, locational information such latitude and longitude via a global positioning system, and for water based units, water temperature and salinity) and internal to the system (e.g., power condition, temperature, system functionality, etc.) All of the information may be transmitted via a radio transmitter to a central base station that can collect the data, monitor system operations and monitor external conditions. The base station may optionally transmit new programs into the system when the system is configured with a receiver connected to the computer. Typical systems for wireless communications, well known to those skilled in art, and remote operation of instruments include the Supervisory Control and Data Acquisition (SCADA) available from, for example, Omega Engineering, Inc. (www.omega.com) among many other commercially available communication and control architectures.

Finally, the data are employed at spatial and temporal scales and linked with suitable models of the atmosphere and biosphere and/or coupled models of same providing model imposed volumes to integrate carbon fluxes over temporal and spatial scales needed to monetize data in the context of carbon trading and exchanges. The end result is a unique isotope characterized carbon emission unit based on standards and references in which both biogenic and fossil fuel components of atmospheric $CO_2$ can be quantified and thus monetized on suitable greenhouse gas and/or carbon trading exchanges.

In certain embodiments, the system is designed to be modular, portable and self contained. The system can utilize conventional line power but can also utilize batteries. If batteries are utilized, the system can also charge the batteries via a solar cell array, thus allowing remote operation. In some embodiments, the system is contained in a weather proof housing that also provides the platform for external sensors, radio antennae and/or solar cell arrays.

DETAILED EMBODIMENTS

Illustrative non-limiting embodiments will now be described to provide an overall understanding of the disclosed system of systems and related methods. One or more examples of the illustrative embodiments are shown in the drawings. In certain embodiments, a system of systems is referred to as the Global Monitor Platform (GMP) representing a unique combination of isotopic instruments, sensors, standards, global references and data telemetry in a field deployable housing suitable for housed and remote operation. The GMP provides the capability to decipher partial and global greenhouse fluxes and thus provides a unique approach to manage greenhouse emissions of the planet to assist in reducing the consequences of global warming. In certain embodiments, any available device(s) for the determination of $^{12}C$, $^{13}C$ and $^{14}C$ composition of $CO_2$ in ambient air are combined in a modular form factor with sample handling and sample conditioning features as described below. In addition, a system of systems may employ any analyzer for concentration and isotopic composition of any gas.

Exemplary embodiments of a method and system of systems are shown diagrammatically in FIGS. 6 through 35. FIGS. 6 through 14 show embodiments of the analyzer employed as one component of the system of systems but with differing analytical components and operational features. FIGS. 15 to 22 describe embodiments of additional operating and methodological components of the system of systems including instrumentation arrays, calibration and inter-calibration of instruments, global references, system architecture and data transmission and methods employing models to produce market ready aggregated data in the context of partial carbon budgets. Referring to FIG. 22 a partial carbon budget is a subset of the global carbon budget reflecting local, regional and otherwise geographically limited areas.

The method and system of systems employ from 1 to any number of devices needed in spatial arrays of the devices placed across the areas of application referred to in FIG. 5 and according to point, local, national and/or state boundaries and greenhouse gas treaties as shown in FIGS. 23 through 35. The apparatus, in one embodiment featuring ruggedization and full remote operation, may be placed virtually anywhere on land and on any body of water, on and or under any surface and in any airspace of the planet Earth. The method and system of systems provides for the placement of devices according to the need for spatial resolution, preferably from 1 device per square mile to 1 device per 4×5 degrees latitude/longitude or according to the specific environmental and geological conditions at a given site and as determined by initial operation and testing of the systems of systems for optimal function to produce carbon tradable results. Further, certain embodiments include sampling inlets representing air from the soil column, soil and/or vegetation surface(s) and within a vertical profile extending from above the surface to any height supported by any structure including but not limited to tree trunks/limbs, buildings, towers, and structure with height as well as including samples obtained from aircraft, balloons or other means.

Some embodiments employ a microprocessor-based data acquisition and control unit (shown as item 8 in FIG. 6) capable of acquiring and storing the data generated by the infrared gas analyzer (IRGA) (shown as item 4 in FIG. 6) and the isotope ratio analyzer (shown as item 24 FIG. 6).

Calibration and Instrument Inter-Comparison and Primary Reference Protocols

As described previously, the analysis of isotopic composition results in data that are expressed as ratios, most simply stated as the data for an unknown against a known reference standard. The ratio approach and appropriate standards for both stable and radiogenic isotopes are well developed but not used in the context of requirements for carbon trading.

However, when employing a number of isotopic analyzers, the key issue of individual and grouped calibrations and inter-comparisons and linkage to global references becomes a difficult and time intensive effort as described previously and recognized as a material obstacle to the implementation of a system of systems to support carbon trading and carbon management.

However, even with the advent of laser based continuous flow analyzers such as those described herein (e.g., gas filled isotopic lasers and/or quantum cascade lasers), the issue of single and multiple instrument calibration and inter-comparisons is required to obtain reliable and verifiable data for carbon emissions that can be used to support carbon trading across multiple geographic locations. In the present case, in which isotopic data are to be used to create integrated flux data for carbon, based on dispersed analyzers at diverse locations, the calibration, inter-calibration issue is a requirement if significant reduction in uncertainty for carbon trading is to be realized.

Assumptions in calibration and inter-comparisons include the following:
1) that the assigned $\delta^{13}C$ of the sealed-cell standard is correct, particularly when changing standard cells;
2) that the response of the analyzer(s) does not substantially vary one from another over time and in space;
3) that the respective samples for a given analyzer or group of analyzers over time and space are processed to a standard level of purity and pre-conditioning; and
4) that the response of the system is not dependent on differences in the source of air with respect to isotopic value, sample size or flow rate and pressure.
5) That performance of individual instruments is monitored and compared to all other instruments in an ensemble of instruments and that comparisons with primary references, consisting of additional reference cells within the analyzer and or external cells, can be used to correct performance issues such as baseline drift or verification of signals above background. The use of sealed cells to contain reference gases and which can be compared instantaneously is an important feature of the system of systems by providing for very high precision and very high stability over short and long operational periods of use.

Figure 12:
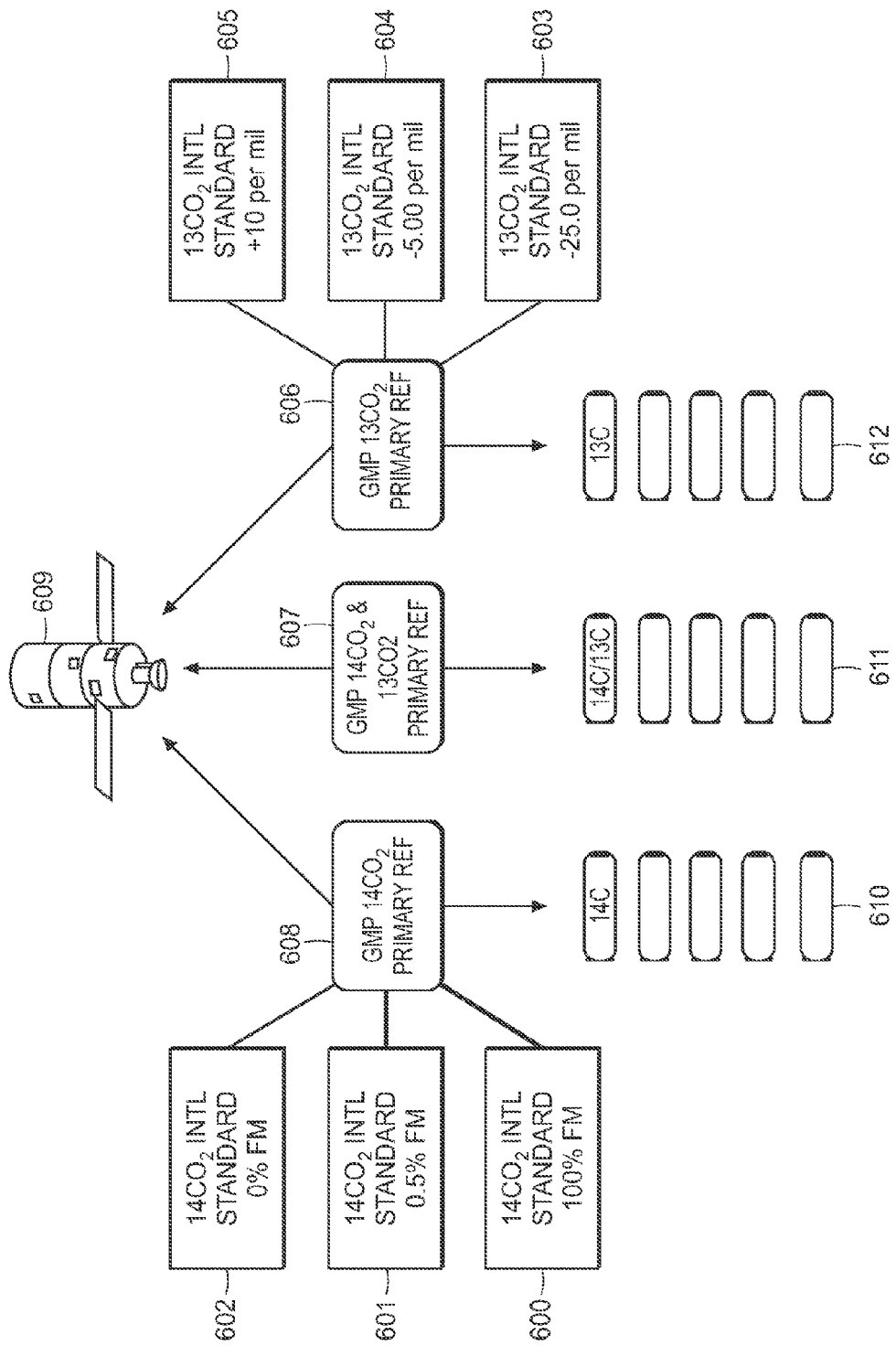
FIG. 12 is a schematic of sealed reference cells consisting of analyzer instrument reference cells, external primary or global reference cells and satellite born 609 reference cells for $^{13}CO_2$ 606, $^{14}CO_2$ 608 and a mixture of $^{13}CO_2$ and $^{14}CO_2$ 607. Sealed reference standards for $^{14}CO_2$ comprising a set of global standards for which other laboratories have obtained data could range from 100% fraction modern $^{14}CO_2$ 600 to 0.5% fraction modern 601 to 0% fraction modern 602. Sealed reference cells for $^{13}CO_2$ may consist of $^{13}$C isotope ratios of −25 per mil 603, −5.00 per mil 604, and +10 per mil 605. Each primary or global reference sealed cell is made such that all sealed cells for a particular isotopic composition are identical (610, 611, 612), thus ensuring comparison between analyzers in an ensemble and across ensembles wherever they may be located.
Figure 13:
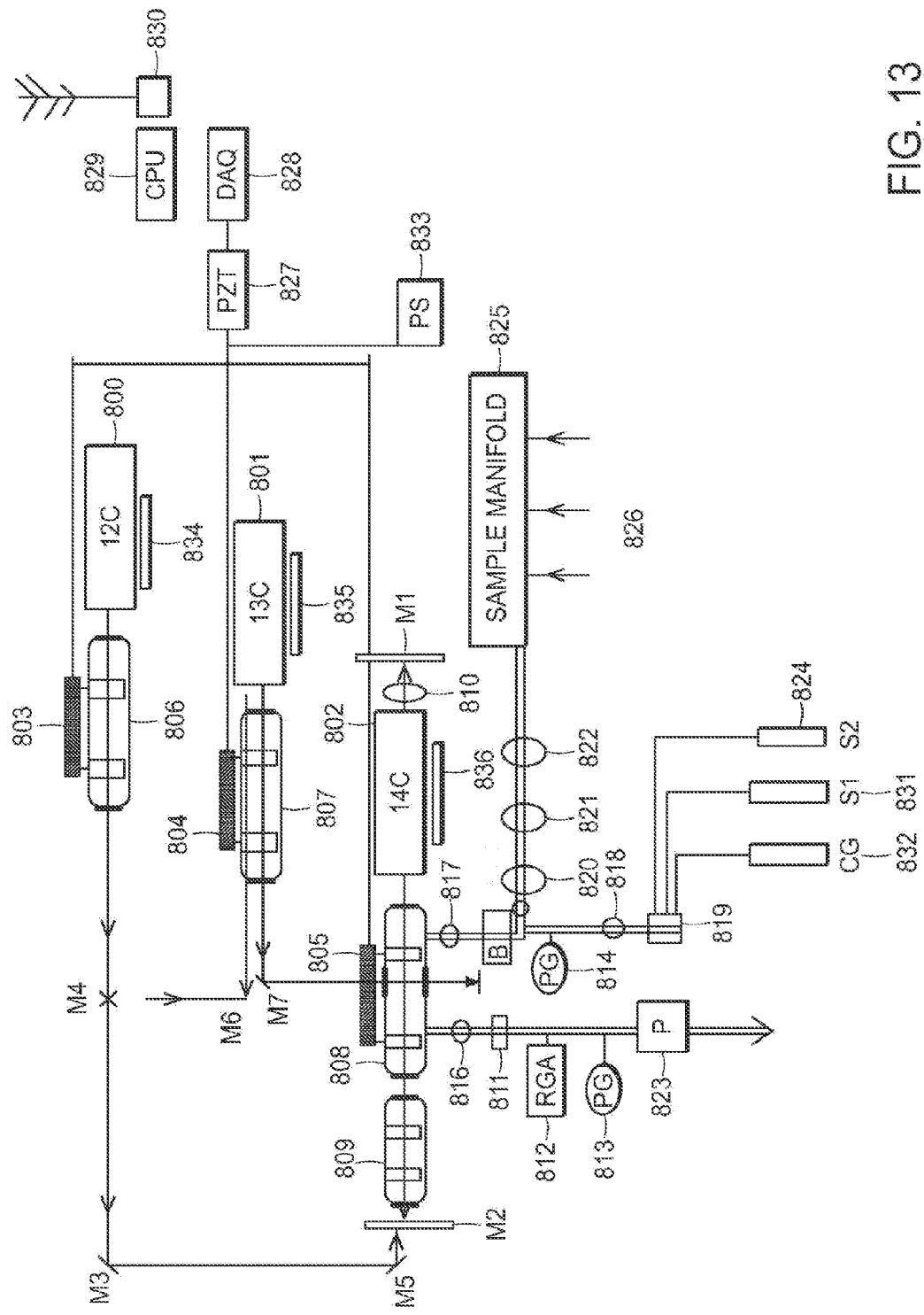
FIG. 13 is a schematic of a three cell laser system for $^{12}$C, $^{13}$C and $^{14}$C measurements according to certain embodiments utilizing three laser systems, a detection system and reference and standard hardware.

An advantage of the non-IRMS approach using essentially continuous flow ambient air with minimal gas handling is that differences amongst analyzers and most gas handling issues are reduced or eliminated. Beyond this improvement, another feature of certain system of systems disclosed herein is the use of a variety of sealed standard reference cells with known isotopic composition as shown in FIG. 12. Such sealed reference cells are shown in FIG. 13 (806, 807, 809) as placed in a three cell instrument. In certain embodiments, the sealed reference cell consists of a single glass cylinder (e.g., quartz) approximately 6 cm in length and 0.5 cm in outside diameter with permanently sealed zinc selenide (ZnSe) end caps to allow the laser light, unchanged, to pass through the cylinder. The glass cylinder reference cells contain the same standard or reference gas for all analyzers. In certain embodiments, a large number of sealed reference cells are filled from the same source of standard air and sealed off with a glass torch or other means to permanently seal the cylinder (FIG. 12). The sealed cells may be filled with a large equilibrated volume of air according to protocols readily known to those skilled in the art of $CO_2$ laser fabrication, such as LTG Laser, Ontario, CA, and to those skilled in the art of standard gas preparation. The sealed cell embodiment described herein FIG. 12 and employed in FIG. 13 is unique in its employment with three isotopic systems ($^{12}C$, $^{13}C$, $^{14}C$) and effectively reduces the difficulty of differences within standard gas preparations employed by different laboratories as described previously and also would greatly reduce noise and instrument drift.

The sealed reference cell gas can then be analyzed by a number of laboratories resulting in highly calibrated standard cells. Referring to FIG. 12 showing a schematic of sealed reference cells consisting of analyzer instrument reference cells, external primary or global reference cells and satellite born 609 reference cells for $^{13}CO_2$ 606, $^{14}CO_2$ 608 and a mixture of $^{13}CO_2$ and $^{14}CO_2$ 607. Sealed reference standards for $^{14}CO_2$ comprising a set of global standards for which other laboratories have obtained data could range from 100% fraction modern $^{14}CO_2$ 600 to 0.5% fraction modern 601 to 0% fraction modern 602. Sealed reference cells for $^{13}CO_2$ may consist of $^{13}C$ isotope ratios of −25 per mil 603, −5.00 per mil 604, and +10 per mil 605. Each primary or global reference sealed cell is made such that all sealed cells for a particular isotopic composition are identical (610, 611, 612), thus ensuring comparison between analyzers in an ensemble and across ensembles wherever they may be located. Such multiple reference cells could be arranged in a linear array or in any placement that allows mirrors to effectively direct the laser beam through all cells offering instantaneous baseline and reference calibration. The use of a sealed reference cell or cells allows the calculation and precision of isotope ratios in a manner analogous to that used with dual inlet IRMS instruments. However, sealed reference cells as described according to certain embodiments herein are used within a framework of calibration and inter-comparison routines applied as appropriate over temporal and spatial scales of interest.

Referring to FIG. 13 a schematic is shown employing three laser cells, $^{12}C$ 800, $^{13}C$ 801 and $^{14}C$ 802. The combination of the three lasers requires a balanced approach to detection and optimization of each laser according to laser power input and output, stability and modulation. The three cell system is one example of an embodiment for all three species of carbon, however the system of systems could be deployed with any isotopic analyzer for any isotopic species. Details of the operation of the three cell system (FIG. 13) are provided below.

Figure 14:
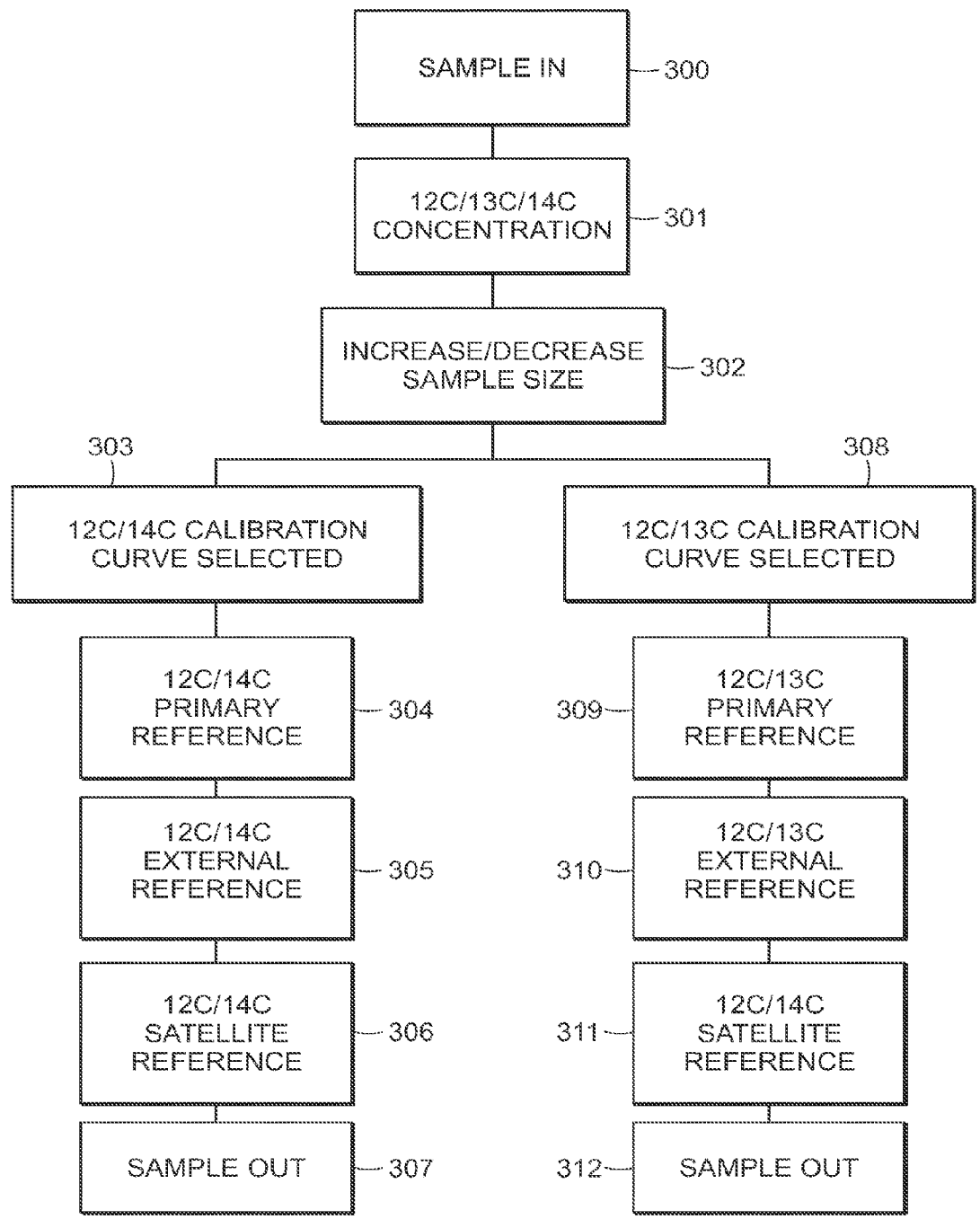
FIG. 14 is a schematic of one embodiment of the sample operation sequence of a three-celled system according to the needs for sample volume increase or decrease such that calibration curves, primary references and external satellite references can be used for optimal measurement of the $^{12}$C/$^{13}$C and $^{14}$C composition of a gas sample. A gas sample 300 enters the analyzer where the concentration of $^{12}$C, $^{13}$C and $^{14}$C are determined 301. If the concentration of $^{13}$CO$_2$ and/or $^{14}$CO$_2$ is too low 302 a cryogenic trap (referring to FIG. 10) may be used to concentrate these species, or if the concentrations are too high 302 for optimal measurement, a bellows assembly (referring to FIG. 11) is utilized to dilute the original sample with carrier gas. Following sample size adjustment a calibration curve for $^{14}$C 303 and for $^{13}$C 308 is selected to ensure that the unknown sample concentration is within the range of the calibration curve. In addition, a primary reference gas can be measured to check the function of the $^{14}$C measurement 304 and the $^{13}$C measurement 309. Primary reference gases 304, 309 are preferably contained in sealed cells within the analyzer and represent the same concentration of $^{13}$C and $^{14}$C in all such primary reference cells of all analyzers such that comparisons between individual analyzers and among different groups of analyzers is assured. An additional check on analyzer function and comparability can be carried out by further measurements utilizing an external reference cell for $^{14}$C 305 and $^{13}$C 310. Both 305 and 310 are ideally located in an external reference gas module that is not equipped for analysis of unknowns, is accessible in real time via telemetry and may be located in one or more areas where ensembles of analyzers are placed. 305 and 306 as external sealed cell reference gases are ideally the same for each isotopic species and preferably have been measured in many laboratories around the world, thus comprising a global reference gas that allows other data sets to be linked directly to data sets resulting from utilization of the multi-isotopic analyzer. Such external global reference gas comparisons provide an additional criteria to ensure comparability across all such instruments and/or can be utilized to make adjustments to data sets with known values of the said reference gases. In addition, an external reference gas comparison may be carried out via satellite operation of said sealed reference gases for $^{13}$C 311 and $^{14}$C 306 such that when the sensor beam of the satellite passes over one or more of multi-isotopic analyzers an immediate comparison between ground based analyzers and space based sensors can be carried out. Sample gas is expelled from the analyzer 307, 312, or is re-routed for a repeat analysis. Repetition of analyses may be valuable to further characterize results for $^{13}$C and $^{14}$C allowing statistical data to be collected to better determine accuracy and precision of the analyzer.

Referring to FIG. 14 a schematic is shown for a typical operational routine that is encoded into software that is controlled either manually or by remote communication. After a sample is introduced to the system a measurement is made to determine concentration of total $CO_2$ and pressure or, alternatively, initial data for each of the isotopes $^{13}C$ and $^{14}C$ are acquired and entered into the data control software. In the case where either the total concentration of $CO_2$ or the concentration of the isotopic species ($^{13}C$, $^{14}C$) is either too large or too small the software control will direct operations to either increase of decrease the respective analytes as provided in FIGS. 9, 10 and 11. Once sample size is considered optimal for measurement a calibration curve maybe implemented and/or comparison with an external sealed standard may be performed. Additional details on the use of standardization as described in FIG. 14 are provided below.

Hardware Architecture for the System of Systems

Figure 15:
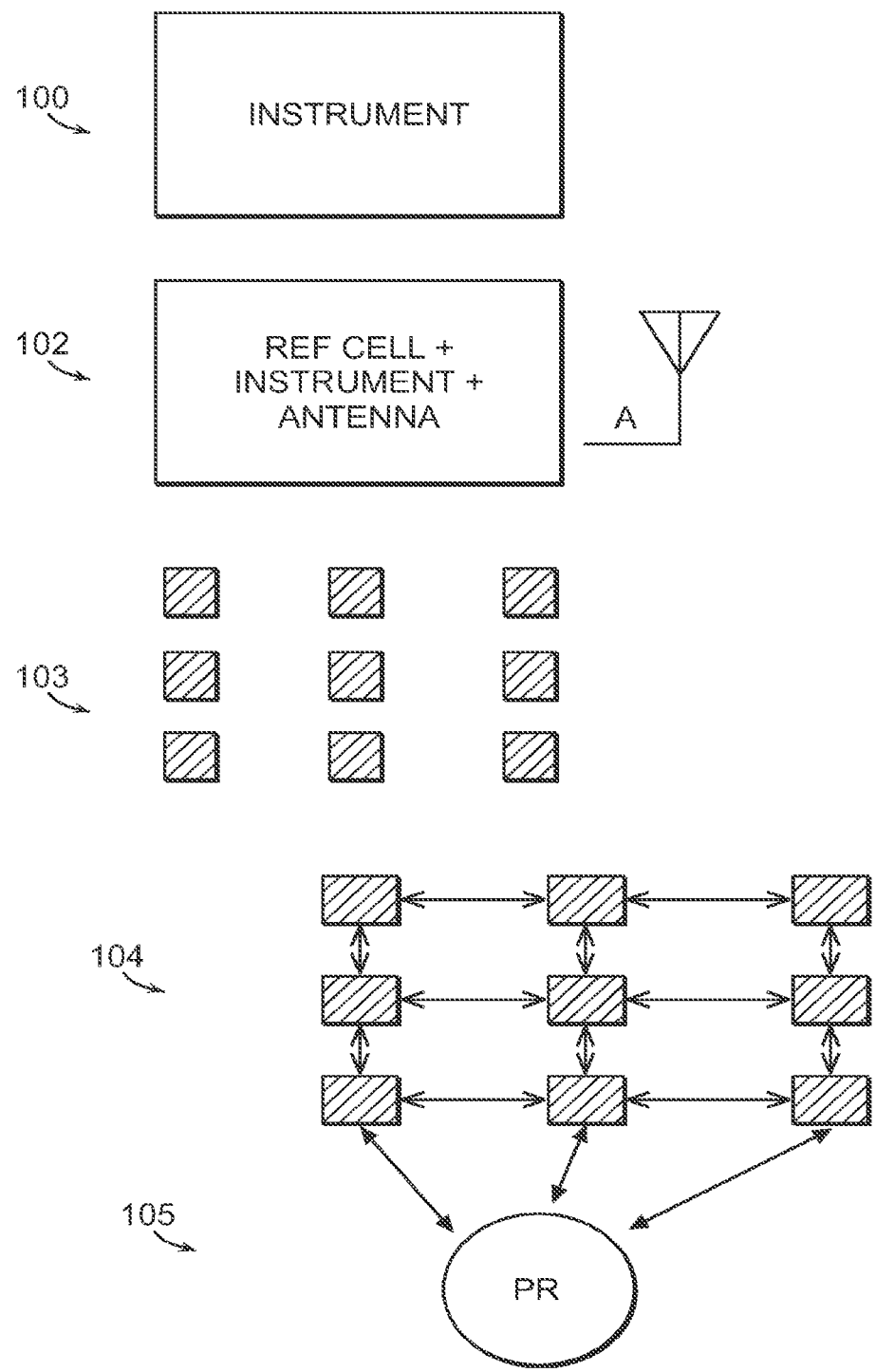
FIG. 15 is an illustration showing instrument, location and instrument inter-comparison overview and organization according to certain embodiments for a single device 100, devices with reference cell and telemetry antenna 102, an array of selected devices 103 and an array of selected devices with inter-comparison and inter-comparability options 104 and reference to an external primary reference (PR) standard 105. Additional external standards may also be incorporated in an analytical design as required to ensure comparability across instrument and across ensembles.

Referring to FIG. 15 a schematic is provided showing the basic hardware components consisting of a base instrument 100, a base instrument with sealed reference cell and telemetry capability 102, an array of analyzers 103 as in 102, and an array of analyzers in a given location to measure, monitor, verify and account for carbon emissions 104, in part effected by instantaneous communication between all analyzers to ensure comparability of data. An additional external reference cell comprising, for example, a primary reference standard may also be incorporated in the array of analyzers to provide an additional means of ensuring analyzer function and comparability of data from all analyzers.

Figure 16:
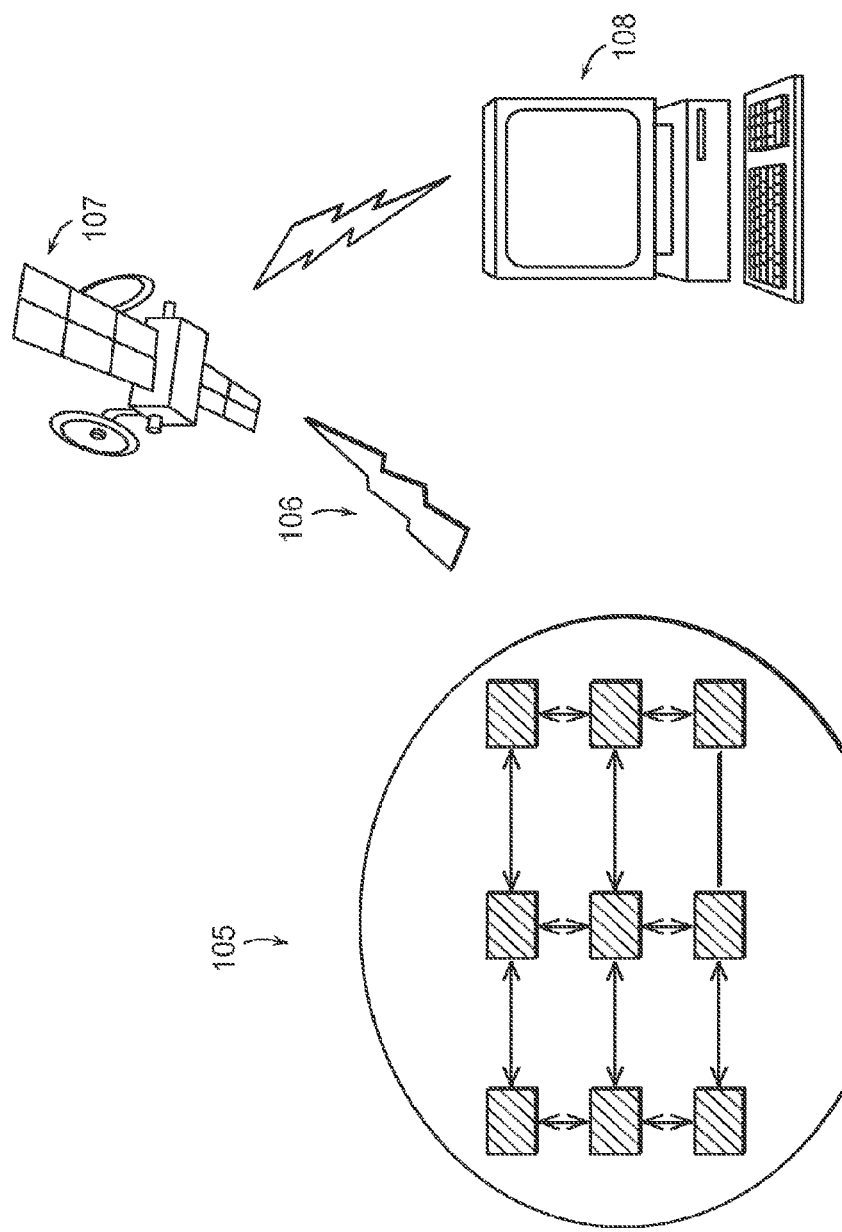
FIG. 16 is an illustration of an embodiment showing an array of inter-calibrated devices covering a specific geographic area 105, transmitting inter-calibrated data from each device via satellite or other wireless means 106, 107 to a central data and model analysis center 108.

Referring to FIG. 16, an array of analyzers in a given location is shown with communication between such analyzers 105, which communicates all data via telemetry or other wireless means 106 to a receiver, such as a satellite 107, the data then being transmitted to a central data station or data center for analysis 108.

Figure 17:
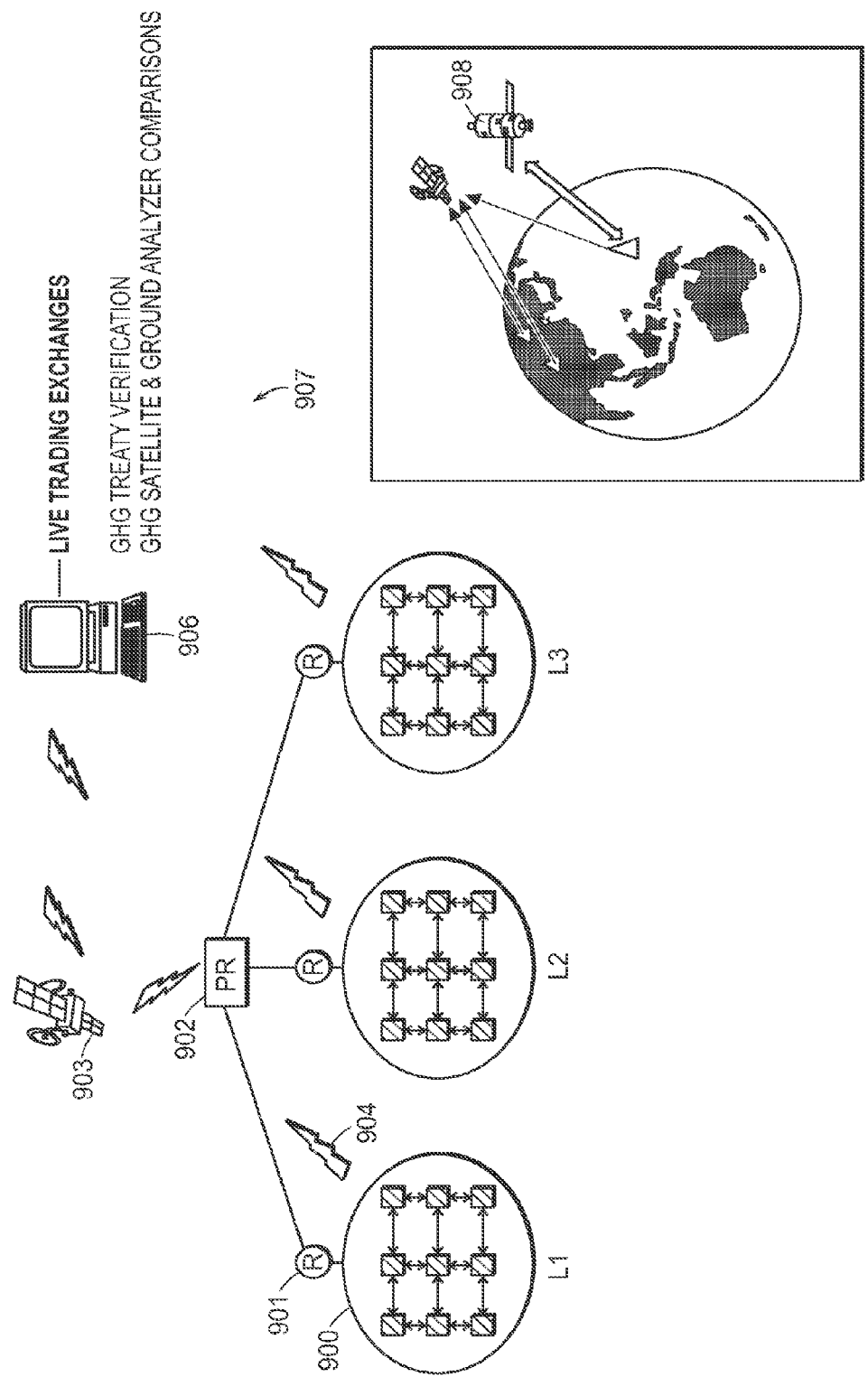
FIG. 17 is an illustration of an embodiment showing ensembles of inter-calibrated devices 900 covering three geographic regions across the Earth (L1, L2, L3). The three ensembles are comprised of 9 individual analyzers that are inter-calibrated within an ensemble and across ensembles utilizing inter-calibration routines (referring to FIG. 14), selected separate reference gases 901, primary reference gases and/or global reference gases (referring to FIG. 14) 902 and optionally embodied in a separate reference gas module and, optionally, as embodied in a satellite that is used for measuring and monitoring greenhouse gases from space 908. Data telemetry can be carried out by any wireless means 904 including a communication satellite 903. 903 relays real time data from the inter-calibrated analyzers 900, reference and/or global reference cells data 901, 902 to data centers and carbon trading exchanges 906 recognizing that reference cells 901, 902 may have the same or different compositions of $^{13}$C and $^{14}$C (referring to FIG. 12) as required depending on technical factors related to the analyzers, calibration routines and inter-calibration routines. In one embodiment such data and communications are near instantaneous providing for an electronically live carbon exchange platform 906. Data from analyzers may also be compared with greenhouse gas sensing satellite data obtained from space 907 offering additional verification of such data.

Referring to FIG. 17 a schematic is provided showing three geographically distinct arrays of analyzers 900, in communication with an external reference sealed cell 901 instrument that allows instantaneous comparison and correction to baseline and calibration data via wireless means 904 for each instrument in the distinct arrays that may then be compared with a primary reference 902 that is linked to well known international standards for $^{13}C$ and $^{14}C$ such as the Vienna Peedee belemnite (VPDB) standard for carbon 13 ratios (Coplen et al., 2006) and the National Bureau of Standards oxalic acid (e.g., NBS OxII) for $^{14}C$ (Scott et al., 2004). In this embodiment both external reference 901 and primary standard sealed cells 902 are based within the region to serve each ensemble. Data are transmitted to data centers to be integrated with models and used, for example, in one embodiment to support live trading on greenhouse gas exchanges 906. In another embodiment reference standards as sealed cells can be housed in a satellite 908 enabled to compare reference values for ensembles of instruments as the satellite passes over the geographic region where the land-based ensembles are placed. Still referring to FIG. 17 passage of a satellite specifically equipped with greenhouse gas sensing capability 908 over a region with an ensemble of analyzers may also enable direct comparisons of data for land based and satellite sensed greenhouse gas concentrations 907. In still another embodiment referring to FIG. 17, such data as received/transmitted by a satellite for the purposes of ensuring verification of land based analyzers or for the purposes of sensing greenhouse gas concentrations at the surface, such data may be instantaneously received and transmitted to support live carbon exchange trading activity 906 across the planet with all analyzers assured to be comparable and thus monetized in a way that accommodates all currency flows/exchanges in the same manner as occurs for stock trading across countries and currencies.

Figure 18:
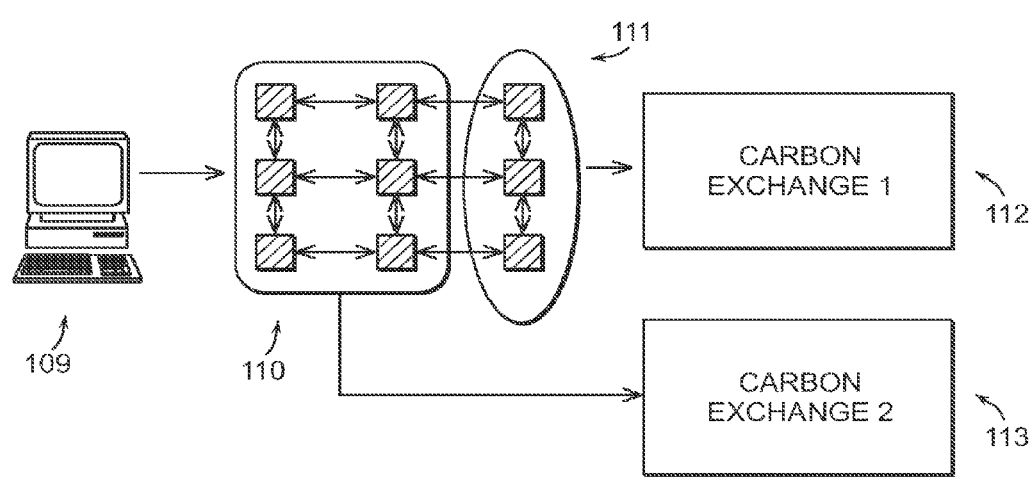
FIG. 18 shows a diagram of a data/model center 109 according to certain embodiments producing integrated model output for specified regions at specified levels of aggregation 110, 111. This leads to translation of data into carbon units for trading such as metric tons CO$_2$ to appropriate carbon based exchanges 112, 113. The data can be accessed in a live-market (e.g., instantaneous) or on a less frequent basis according to type of carbon represented, such as biogenic carbon (e.g., forest carbon) versus industrial fossil fuel based carbon, and according to trading protocols for a specific exchange.

Referring to FIG. 18 a schematic is shown in which a data station 109 employs software and/or models of any kind that calculates the metric tons of carbon or carbon equivalents for any ensemble of analyzers or groups of analyzers 110 and 111 across spatial locations and according to specified time periods and providing such data to carbon exchanges 112, 113 located anywhere trading may be appropriate.

Figure 19:
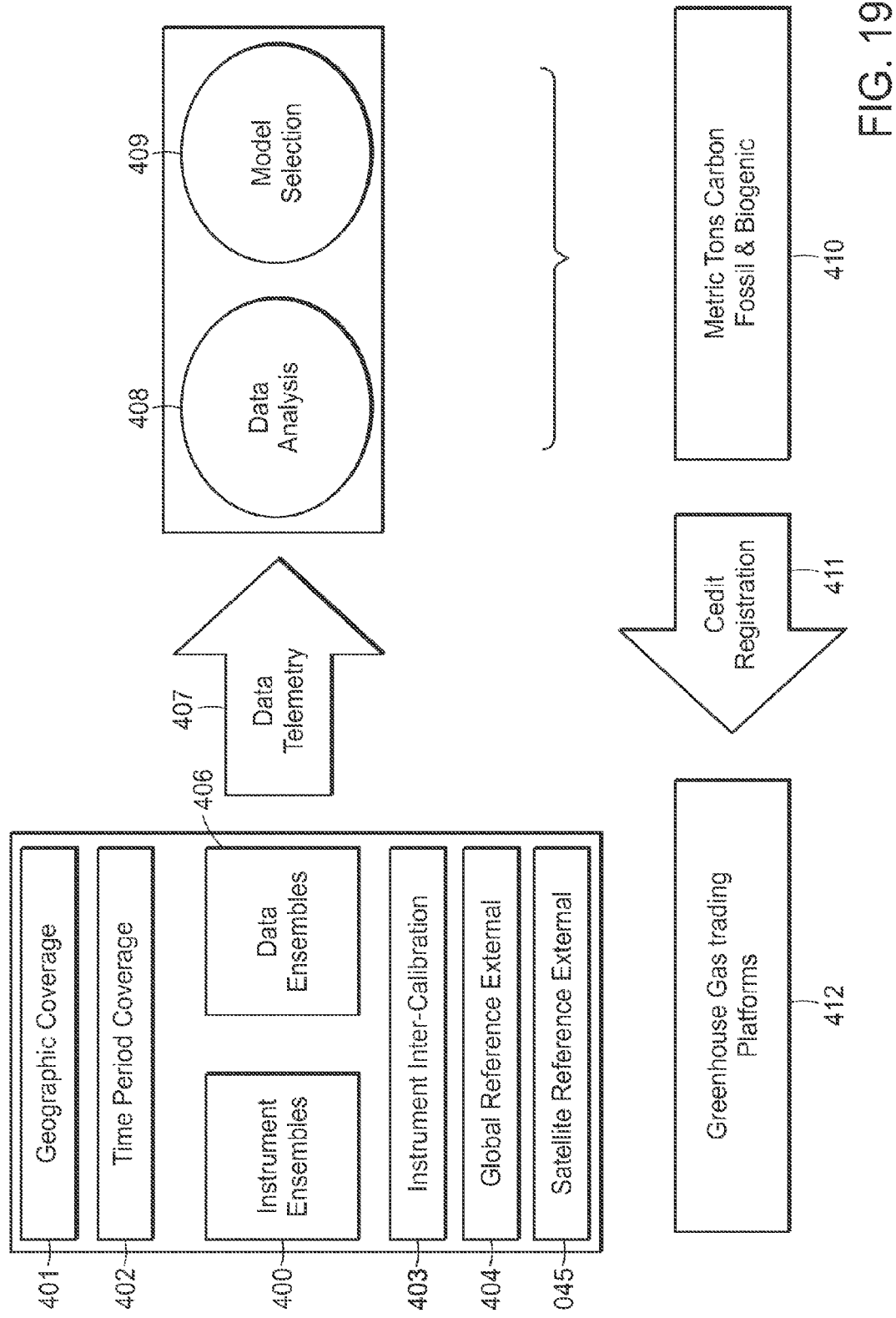
FIG. 19 shows a summary of the main component processes of the system of systems for a given geographic area 401, a given time period 402, with instruments 400 and data from samples measured by analyzers 406, groups or ensembles of analyzers 400 and data ensembles 406, shared calibration and inter-calibration protocols 403, global reference protocol 404 and external satellite based standards 405. All data are transmitted via wireless or other means of telemetry 407 to data centers that manage and incorporate the data 408 in one or more models 409 that ultimately are converted to metric tons of biogenic or fossil fuel derived carbon 410. Such units can be registered and other administratively handled 411 for sale on an appropriate greenhouse gas trading exchanges, platforms, etc. 412.

FIG. 19 shows a summary of the main component processes of the system of systems for a given geographic area 401, a given time period 402, with instruments 400 and data from samples measured by analyzers 406, groups or ensembles of analyzers 400 and data ensembles 406, shared calibration and inter-calibration protocols 403, global reference protocols 404, and external satellite based reference standards 405. All data are transmitted via wireless or other means of telemetry 407 to data centers that manage and incorporate the data 408 in one or more models 409 that ultimately are converted to metric tons of biogenic or fossil fuel derived carbon 410. Such units can be registered as credits according to the rules of a given trading system 411 for sale on an appropriate greenhouse gas trading exchanges, platforms 412.

Figure 20A:
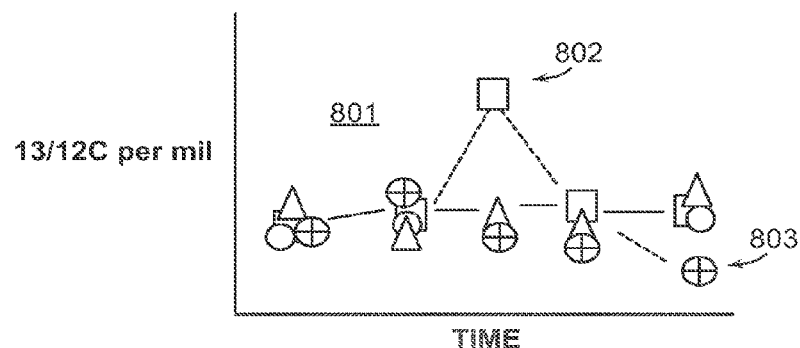
FIG. 20A-FIG. 20C show an example of inter-calibration architecture resulting in a $^{13}$C data set (panel A) 801 from the analyzers 804, 805, 806 and 807 (panel B). The analyzers 804, 805, 806 and 807 are placed in discrete locations (panel C). Analyzers 804, 805, 806 and 807 may also be integrated with an optional external reference and/or global reference gas module 809 to ensure comparability across instruments in time and space.
Figure 20B:
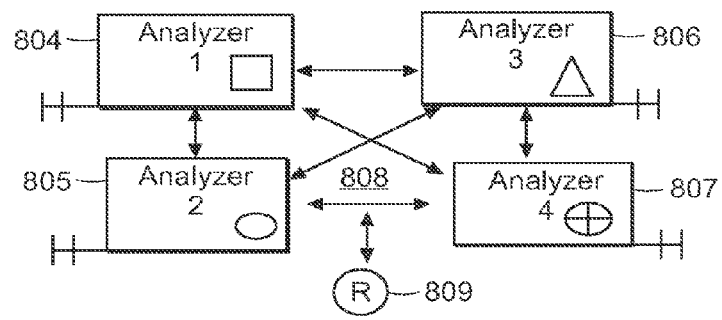
Figure 20C:
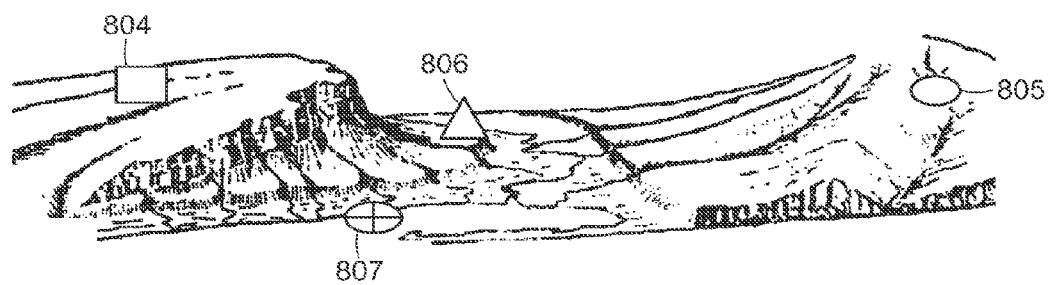

FIG. 20, panel A, illustrates hypothetical isotope data for $^{13}C/^{12}C$ and $^{14}C/^{12}C$ ratios resulting from four instruments in different locations covering five points in time. The data for the four instruments, denoted by symbols (squares, circles, cross-hatched circles and triangles) are shown in Panel A with solid lines 801 connecting data of similar trend and dotted lines connecting data recognized as outliers 802 and 803. A feature of the software control protocols according to certain embodiments is to recognize outlier data as it is produced in each instrument and recognized by routine calibration curves, primary standards and external standards (e.g., FIG. 14). Thus, in Panel A, the outliers above and below the trend line (802 and 803) would be eliminated from the corresponding data stream and instrument primary data record, although retained in an appropriate file. In some embodiments, each of the instruments (804, 805, 806, 807) may also be referenced to an external primary reference cell 809 as shown in FIG. 14, or may be compared with satellite space based measurements representing an additional method to cross check data results in real time and providing a global reference data point. Referring to Panel B, it can be seen further that when such data quality and assurance programs are applied to each instrument 804, 805, 806 and 807 within an array, a software program can be devised to query each instrument against any other instrument 808 (represented by cross arrows between each pair of devices) verifying normal function and otherwise eliminating outliers or other conditions during which data are either not collected or a malfunction is registered. Such controls are essential to ensure comparability for analyzers that are located far from each other and in different environments (Panel C). Thus, according to certain embodiments, for defined intervals over time and space all outlier data for all instruments in an array are eliminated from the primary data set, thus producing a network or data fabric that is quality assured. Non-conforming data may be set to trigger an alarm signifying that the instrument is not functioning properly. Such protocols for arrays of instruments are well known to one skilled in the art of instrument controls and software control of such devices according to set protocols. For example, the National Instrument Company, Austin, Tex. (www.ni.com) offers Lab View (e.g., Model 8.6), a well known instrument control software package, that allows custom data acquisition, manipulation and interactive control of instruments to accomplish complex routines such as those described above.

This protocol, which can be run automatically in real time using advanced wireless control protocols as described below, represents an inter-calibration routine that promotes successful performance of a system of systems disclosed herein. Note that in Panel C, the location of the four instruments is such that any combination of data from the locations may be employed to generate aggregated data and results suitable for carbon trading. The discrete locational data representing one or more locations may be used to reduce or expand the spatial footprint or to track rapid changes in a single location depending on other factors including environmental conditions. The inter-calibration routine may be applied to any number of devices located in arrays in many disparate locations around the world and disparate trading networks such as the EU ETS and RGGI carbon trading platforms as referenced previously. Such a network or fabric of data can then be integrated with appropriate models to further aggregate and interpolate data to provide cumulative carbon fluxes over defined spatial and temporal domains. Thus, the system of systems, according to certain embodiments, offers self regulating calibration and inter-calibration routines to ensure data comparability in a way that has not been implemented to date for the rare forms of carbon as disclosed herein.

System Architecture for Data Communication and Transmission Using SCADA

The term SCADA stands for Supervisory Control And Data Acquisition. Such systems are readily available commercially from vendors such as Bentek Systems, Inc., Alberta, Canada (www.scadalink.com). A SCADA system is a common process automation system which is used to gather data from sensors and instruments located at remote sites and to transmit and display this data at a central site for either control or monitoring purposes. In the certain embodiments, referring to FIG. 21, a SCADA system is used to control and monitor isotopic data resulting from the isotopic analyzers 901 as disclosed herein. The collected data is usually viewed on one or more master SCADA Host computers 902 located at the central or master site with options for intermediate host computers 903 such as regional areas that may be employing widely separated networks of isotopic monitors. A real world SCADA system can monitor and control hundreds of thousands of input/output (I/O) points. A typical SCADA application for a system of systems as described herein would be to monitor devices producing isotopic composition for $^{13}C$ and $^{14}C$ isotope ratios, calibration and data transmission for one or more devices in a given network and for all networks. The various software and hardware features of the individual devices and communication within a network of devices are controlled by employing both analog and digital signals.

In at least some embodiments utilizing remote sites and/or disparate groups of sites, another layer of equipment between the remote sensors and instruments and the central computer is employed. This intermediate equipment exists on the remote side and connects to the sensors and field instruments. The device sensors will typically have digital or analog I/O and these signals are not in a form that can be easily communicated over long distances. The intermediate equipment is used to digitize then packetize the sensor signals so that they can be digitally transmitted via an industrial communications protocol over long distances to the central site. Typical equipment, well known to those skilled in the art of SCADA, that handles this function are PLC's (Programmable Logic Controllers) and RTU's (Remote Terminal Units) commonly housed in the same instrument box or RTU 901. In certain embodiments, isotopic analyzers spread across one or more landscapes will be classified as RTU's 901 equipped with PLC's. The RTU and PLC is equipped with the appropriate SCADA communication device 904. One such SCADA device, common in the industry and well known to those skilled in the art of SCADA communications devices is the SCADALink 900-MB RTU/radio modem enabling wide-area, remote, point-multi-point SCADA communication systems sold by Bentek Systems, Inc., of Alberta, Canada. These devices employ de facto standard industrial data communication protocols such as Modbus, AB-DF1, and DNP3.0 to transmit the sensor data, all well known to those skilled in the art of communication protocols. Typical physical interface standards are Bel 202 modem, RS-485 & RS-232, also well known to those skilled in the art of interface standards.

Typically a SCADA system consists of four major elements:
1. Master Terminal Unit (MTU) 902
2. Remote Terminal Unit (RTU) 901
3. Communication Equipment 904
4. SCADA Software The Master Terminal Unit 902 is usually defined as the master or heart of a SCADA system and is located at the operator's central control facility. In the illustrated embodiment the MTU represents the primary control and operations center that monitors, controls, receives and processes data that is produced by the isotopic analyzers. The MTU initiates virtually all communication with remote sites and interfaces with an operator. Data from remote field devices ($^{13}C$, $^{14}C$, $CO_2$ concentration data, calibration routines, alarm conditions, etc.) is sent to the MTU to be processed, stored and/or sent to other systems. For example, in the present case the MTU may send the data to regional carbon trading platforms anywhere on the planet.

As discussed earlier, the Remote Terminal Unit 901 is usually defined as a communication satellite or node within the SCADA system and is located at the remote site; in this case representing individual isotopic analyzers across the landscape. The RTU gathers data from each of the field devices in memory until the MTU 902 initiates a send command such as a command to transmit isotopic data for a given period of time from one or more field isotopic analyzers 901 or one or more intermediate data collection sites 903. In one embodiment, isotopic analyzers may be equipped with microcomputers and programmable logic controllers (PLCs) that can perform functions at the remote site without any direction from the MTU and is considered herein as part of the RTU 901. In addition, PLCs can be modular and expandable for the purpose of measuring, monitoring and controlling additional field devices. Thus, in the present case, in one embodiment, a regional ensemble of many RTUs 901 will be equipped with PLCs to specifically measure and monitor calibration, inter-calibration and reference routines and may also allow control functions, site condition reports, re-programming capacity and alarm functions for one or more isotopic analyzers. Within the RTU 901 is the central processing unit (CPU) that receives a data stream from the protocol that the communication equipment uses. The protocol can be open such as Modbus, Transmission Control Protocol and Internet Protocol (TCP/IP) or a proprietary closed protocol; all aforesaid protocols are well known to one skilled in the art of data transmission protocols. When the RTU 901 sees its node address embedded in the protocol, data is interpreted and the CPU directs the specified action to take. All functions, thus, can be carried out from one or more master sites controlling any number of isotopic analyzers.

In various embodiments, the way the SCADA system network or topology is set up can vary, but each system relies on uninterrupted, bidirectional communication between the MTU and the RTU. This can be accomplished in various ways, e.g., private wire lines, buried cable, telephone, radios, modems, microwave dishes, wireless/cellular 905, satellites 906, or other atmospheric means, and many times, systems employ more than one means of communicating to the remote site. This may include dial-up or dedicated voice grade telephone lines, DSL (Digital Subscriber Line), Integrated Service Digital Network (ISDN), cable, fiber optics, Wi-Fi, or other broadband services. A system of systems as disclosed herein can make use of all communication systems covering local, regional and remote sites as is well known to those skilled in the art of SCADA systems.

A typical SCADA system provides a Human Machine Interface (HMI) 907 allowing the operator to visualize functions as the system is operating. Accordingly, in the present disclosure, visualization may include, without limitation, contour surfaces of carbon flux, calibration and inter-calibration routines, or simply carbon flux data in metric tons of Carbon attributed to either biogenic or industrial sources for a given array of devices over a given time period. In certain embodiments, the operator can also use the HMI to change set points, view critical condition alerts and warnings, and analyze, archive or present data trends. Since the advent of Windows NT, the HMI software can be installed on PC hardware as a reliable representation of the real system at work. Common HMI software packages include Cimplicity (GE-Fanuc), RSView (Rockwell Automation), IFIX (Intellution) and InTouch (Wonderware). Most of these software packages use standard data manipulation/presentation tools for reporting and archiving data and integrate well with Microsoft Excel, Access and Word. Web-based technology is also accepted as well. Data collected by the SCADA system can be sent to web servers that dynamically generate HTML pages. These pages are then sent to a LAN system at the operator's site or published to the Internet. In the illustrated embodiment, the data after being received by the MTU 902 will be used to generate carbon flux data compatible for use in one or more carbon exchange platforms 915.

Figure 21:
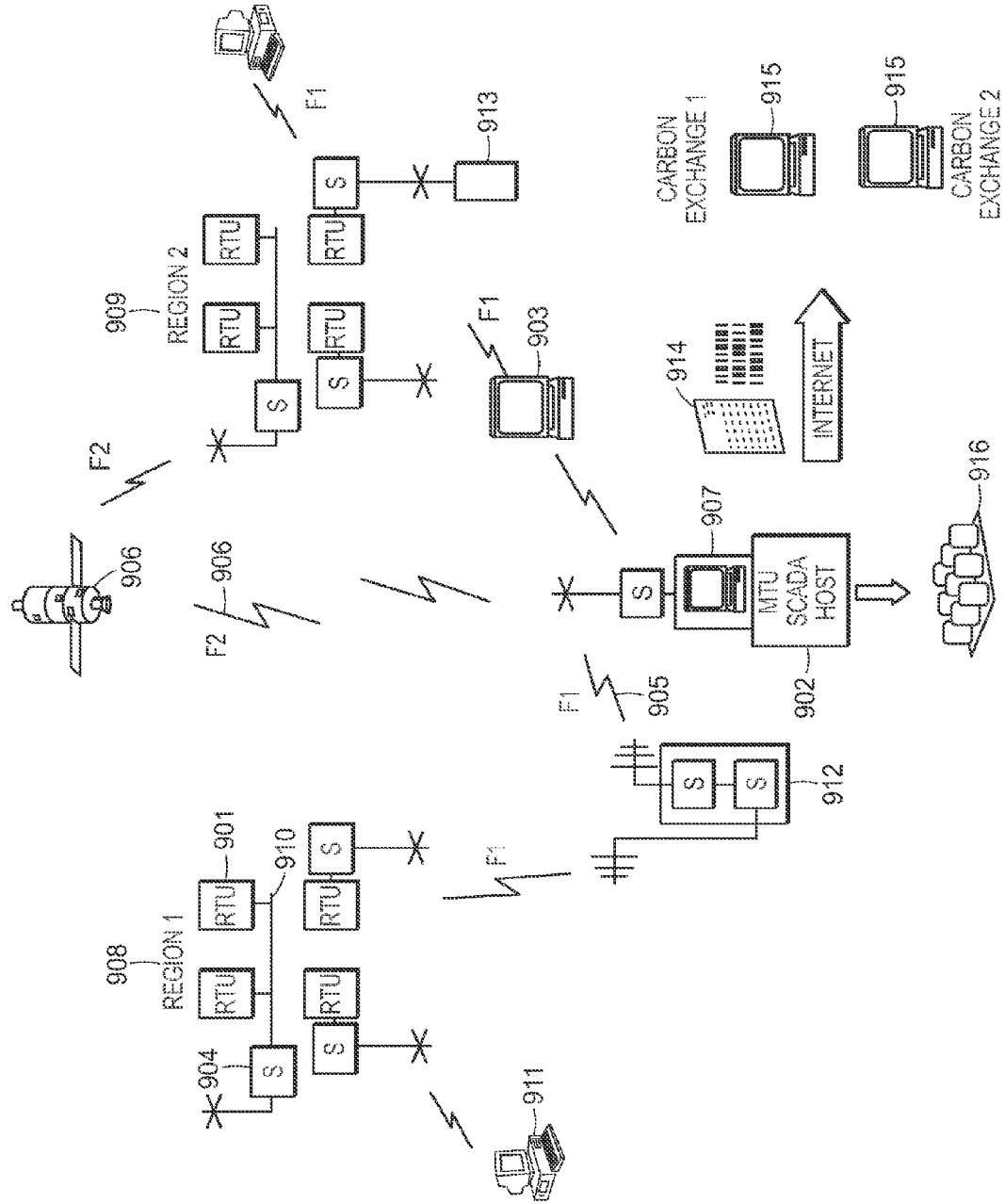
FIG. 21 shows an example of SCADA communication and network architecture for data transmission from individual or grouped isotopic analyzers, comparison with optional external primary reference standard, collection of such data by a master host and subsequent transmission to carbon exchanges.

In summary, referring to FIG. 21, a number of isotopic analyzers are placed in the field in two separate locations 908, 909, all employing an instrument architecture supporting a PLC within the RTU 901 instrument housing. In one embodiment, each discrete location with an RTU is equipped with a SCADA communicator 904. In another embodiment, RTUs that are close enough to be wired to each other 910 may employ a single SCADA unit for communications. In still another embodiment, handheld computers 911 within a given network may also monitor data by wireless or other means. In another embodiment, in which wireless communication is involved, a repeater unit 912, available from Bentek Systems, Alberta, Canada, and model SCADALink SMX-900, may be involved to boost the signal for final transmission to the MTU 902. In yet another embodiment, an intermediate MTU 903 is used to capture data prior to transmission to the primary MTU 902. In yet another embodiment, a solar powered SCADA communications unit 913 may be employed in remote areas with limited electrical connectivity, using for example, the Solar SCADA Link, available from Bentek Systems, Alberta, and Canada. Data communications may be effected by wireless transmission 905 or satellite 906 systems. The data are received by the primary MTU 902 and rendered in a variety of displays, including but not limited to contour surfaces for carbon flux, charts, graphs and three-dimensional visualizations within the human machine interface, HMI, 907. Appropriate data products resulting from the use of mathematical calculations and models finally yield carbon flux data in metric tons, specifying both biogenic and anthropogenic/industrial components as sources or sinks for a given spatial and temporal domain. Such data are encrypted 914 and transmitted to carbon exchanges 915. Data is automatically stored within a variety of on-site and off-site databases 916.

Model Aggregation of Spatial and Temporal Isotopic Data

Data for $^{13}C$ and $^{14}C$ isotopic compositions along with data for $CO_2$ concentration provide the input for a variety of models, ranging from discrete soil carbon models to agricultural models to those covering much larger scales, from local sites to regions to continents to global models. The interplay between the density of the isotopic measurement sites, local meteorological conditions, time period of the measurements and the mechanistic basis of the models themselves is considered when using models to derive carbon flux data that can be used for trading purposes as well as when designing sampling sites and arrays of measuring devices.

According to certain embodiments, models are used to interpolate data obtained from spatial and temporal arrays of isotopic measuring devices resulting in integrated flux data, in metric tons of carbon, for the area and/or process that is being measured. In each case, the carbon flux for a discrete spatial and temporal domain represents a partial carbon budget in the context of the global carbon budget. Carbon trading, by its nature, consists of partial carbon budgets and must be characterized with acceptable uncertainty and predictive power. Thus, a system of systems according to certain embodiments described thus far comprises the methodologies and associated spatial and temporal domains to craft a wide variety of partial carbon budgets that can be used to support carbon trading and ultimately to support a detailed understanding of the global carbon budget itself.

Examples of specific areas and/or processes for which integrated flux data would be useful for carbon trading are illustrated in FIGS. 22 to 35. In each case, a specific model can be used, for example, based on published work, to demonstrate efficacy for the given application. Relevant carbon models include soil models published by Zobitz et al., 2008; forest exchange models published by Urbanski et al., 2007 and Sott et al., 2004; regional exchange models published by Lloyd et al., 2001, Levin et al., 2003 and Lai et al., 2006; agricultural carbon cycle models published by West and Marland, 2002; regional fossil fuel emissions models published by Kosovic et al., 2008; ocean carbon cycle models published by Matsumoto et al., 2004; geologic carbon sequestration models published by Venteris et al., 2006; and continental scale models published by Peters et al., 2007. While the aforementioned model publications are exemplary, the academic literature contains many models in the areas described and others suitable for the treatment of data to produce material fluxes, reported in metric tons, which can be used by carbon exchanges as verified carbon units. Each ensemble of analyzers may require a specific combination of models to yield required results and thus represents a proprietary model integration function for a variety of embodiments of the system of systems.

An overview of discrete system of systems is illustrated in FIG. 22 providing frameworks of varying scales, ranging from global budgets 400 to discrete soil budgets 403 in the terrestrial domain 408 or discrete marine carbon budgets 405 in the oceanic domain 407. The double ended arrows signify carbon flux in both directions, positive meaning emitted to the atmosphere and downward or negative flux meaning sequestered. The dual arrows, solid referring to fossil/industrial carbon and the dashed arrows referring to biogenic, natural carbon, show the final outcome of the illustrated system of systems, that is, a dual carbon accounting of the primary carbon components in the atmosphere. Referring to FIG. 22, all boxes shown represent interrelated budgets focused on components of the carbon cycle, both anthropogenic/industrial 409 and natural 407, 408. The common model element for an accurate partial carbon budget is atmospheric transport 406. Atmospheric transport in both the vertical and horizontal planes can rapidly move and mix emissions across large spatial scales over short time periods. Such a rendering of the movement history and final dispersion of carbon emissions will be useful at the state and regional levels to manage and monetize carbon emissions as discussed by Riley et al., 2008.

A partial budget, in embodiments of large scale efforts such as regional and continental scales, involves placing an "invisible box" or control volume over the area of monitoring, and tracking movement of all air across the boundaries and the concentrations of isotopes and carbon dioxide as precisely as possible. The use of meteorological data with high resolution in time and space can be adapted for model use. In conjunction with isotopic data from an array of devices, this can be used to calculate large scale fluxes. Such an approach is reported by Kosovic, 2008, and is well known to one skilled in the art of atmospheric transport models. The density of measuring points across the landscape will vary according to landscape heterogeneity, topography, design criteria and desired resolution and accuracy and is optimally configured according to initial test configurations of the system of systems.

One example of a model approach well suited for a system of systems as disclosed here has been reported by Riley et al., 2008. In this study, analysis of leaf samples for $^{14}C$ content and hence of fossil fuel emissions were utilized to estimate atmospheric $^{14}C$ again demonstrating that direct measurement of $^{14}C$ in the atmosphere is not feasible with current technology. The study coupled MM5, and LSM1 tracer models to infer fossil $CO_2$ emissions and movement in the state of California based on the $^{14}C$ of plant data. The MM5 model based on the work of Grell et al. (1995) comprised a nonhydrostatic, terrain following sigma-coordinate mesoscale meteorological model typically used in weather forecasting and in studies of atmospheric dynamics, surface and atmosphere coupling, and pollutant dispersion. The model has been applied in many studies over a variety of terrains, including areas of complex topography and heterogeneous land-cover. The physics packages used for the simulations can be found in Riley et al. (2008) and are well known to those skilled in the art of atmospheric transport models.

The LSM1 model used in the Riley et al. (2008) study was fashioned after Bonan (1996) and is a "big-leaf" land-surface model that simulates $CO_2$, $H_2O$, and energy fluxes between ecosystems and the atmosphere. Modules were included by Riley et al. (2008) that simulate fluxes of radiation, momentum, sensible heat, and latent heat; belowground energy and water fluxes, and coupled $CO_2$ and $H_2O$ exchange between soil, plants, and the atmosphere. Twenty-eight land surface types, comprising varying fractional covers of thirteen plant types, were simulated in the model as reported by Riley et al. (2008). Riley reports that the integration of the two models MM5 and LSM1 has been tested and found to accurately predict the desired fluxes.

Riley et al. (2008) employed a standard initialization procedure for MM5 v3.5, which applies first-guess and boundary condition fields interpolated from the NOAA National Center for Environmental Prediction (NCEP) reanalysis data to the outer computational grid. The model was run with a single domain with horizontal resolution of 36 km and 18 vertical sigma layers between the surface and 5000 Pa; the time step used was 108 s, and output was generated every two hours. The two hourly model output was used in the analyses that follow by integrating or averaging over hourly, seasonal, or annual periods. An integrated flux map resulting from the work of Riley et al. (2008) is shown in FIG. 22 B, as an exemplary and readily available model approach for use with a system of systems offering integrated flux data over varying temporal and spatial scales. The three dimensional contour of flux was determined with a model resolution of 36 square kilometers, duly representative of one embodiment for an array of isotopic analyzers.

Figure 22A:
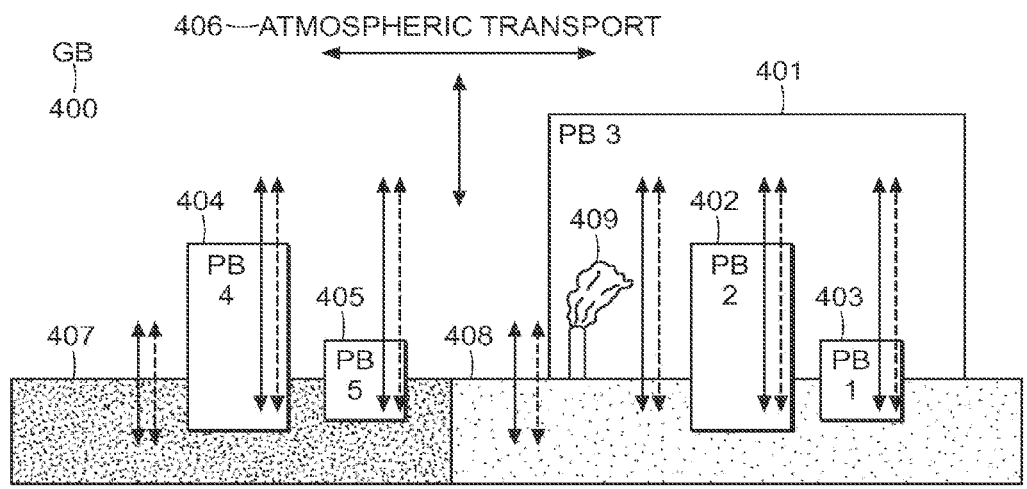
FIG. 22A and FIG. 22B show hypothetical partial carbon budgets, their nested structure (panel A) and exemplary model results (panel B) for dual carbon accounting.
Figure 22B:
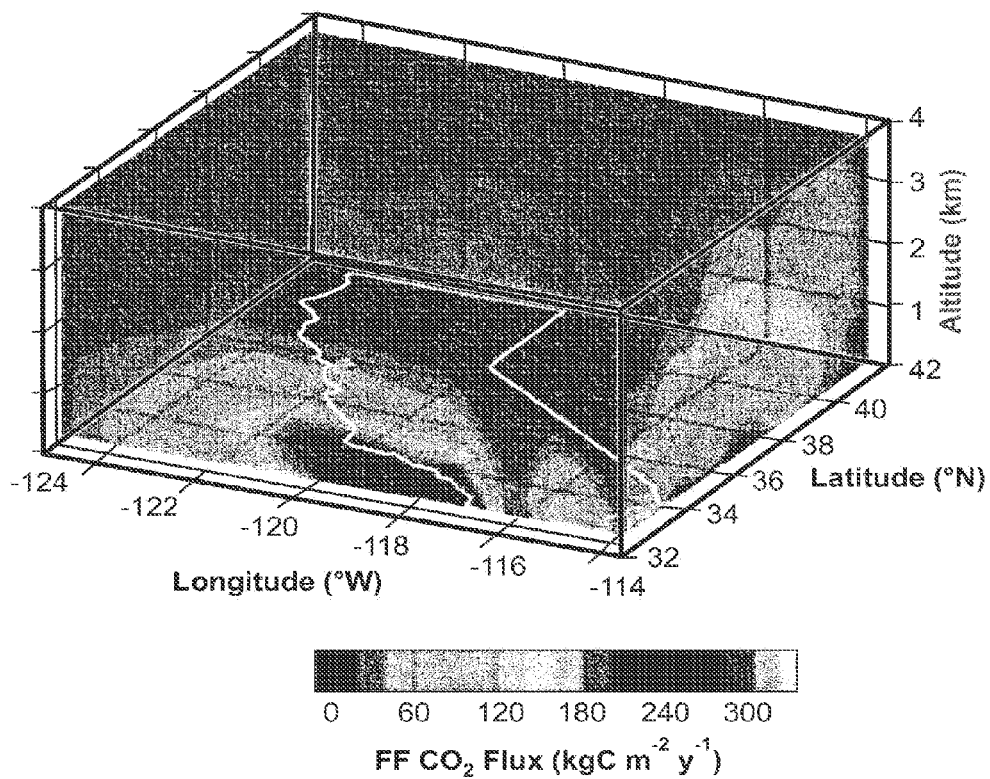

Referring to FIG. 22A, and recognizing that each of the partial budgets shown can be treated in a manner similar to that reported by Riley et al. (2008), the partial budget 401, is comprised of partial budgets 409, 402, and 403, in the simple example used. The system of systems disclosed according to certain embodiments herein is the only approach known to date that allows determination of nested partial budgets that can be integrated into larger and larger budgets based on real time, high precision flux data for both biogenic and anthropogenic/industrial emissions. Following on from the previous partial budget example, partial budgets 401 and 408 representing the terrestrial domain and partial budgets 404, 405 and 407 representing the oceanic domain are in material balance with the GB 400 over a given period of time and ultimately representing fully mixed air from all partial budgets. Thus, the simplified global budget and partial budgets illustrated in FIG. 22 show that a system of systems as disclosed herein offers a means to quantify carbon flux across varying scales of time and space that are compatible with requirements for carbon exchanges representing varied and discrete locations and carbon budget dynamics.

Again referring to FIG. 22 B, the data sets representing discrete measurements in time and space can be converted to molar volumes of carbon emitted, reduced or sequestered. The model data can be processed to cover the carbon flux from major cities, for example, agricultural areas, wilderness areas and residential areas, all representing partial budgets. The entire set of partial budgets, for a given geographical area can then be used to assemble a carbon budget, for example, for an entire state. Given that each of the partial budgets can be expressed in metric tons of carbon either emitted, reduced or sequestered, such data can be directly used to identify carbon credits for trading (e.g., carbon credits represent carbon reductions or avoided carbon by sequestration). The process of registering credits with carbon exchanges, such as the Chicago Climate Exchange or the European Union Emissions Trading Scheme is well known to those skilled in the art of registering and selling carbon credits. The process in summary involves identifying acceptable domains for carbon trading such as agricultural, landfill gas, forest activities, etc. A project that meets the domain criteria submits an application to the exchange involving a series of documents describing in detail the project, location and method of monitoring. Once approved, the project establishes a baseline condition and then begins the project. Monitoring is performed based on a system of systems approach as described herein. Time periods of monitoring are reported and subsequently verified and certified by the exchange, after which the credits are registered on the exchange and listed for sale.

However, measuring, monitoring and verification methods for carbon trading have been to date poorly developed and lacking a unified methodology. In contrast, according to certain embodiments herein, the data for the state of California, for example, would consist of:

$^{14}C$ units (metric tons): reduced+sequestered−emitted $^{13}C$ units (metric tons): sequestered−emitted Thus, for the first time, data for carbon trading can be defined according to the fossil and biogenic components, as well as providing data to track management of carbon fluxes due to policy action. The data can also reveal the source components in greater detail, and assess ecosystem function in some cases, as shown in FIG. 2. Thus, a system of systems according to certain embodiments integrates natural and fossil emissions, as well as identifies source components and ecosystem function.

A system of systems according to certain embodiments herein offers a new approach using the dual accounting of both biogenic and fossil carbon fluxes to create meaningful carbon credits that may be priced and valued based on scientific data that are directly linked to carbon emissions by humans and the natural environment we live in.

General Operation of the Analyzer of the System of Systems

In some embodiments of the method and system of systems, measurement of a species concentration and the isotope ratios of the species (e.g., carbon dioxide concentration and carbon isotope ratios) of a gas mixture, such as air from any source as shown in FIG. 6, is performed, the appropriate data are written to memory in the device and then transmitted to a central location as shown in FIGS. 16, 17 and 18. With reference to FIG. 6, the system operates as follows. The gas sample is input via gas inlet tube 2 into the system. In further embodiments, the inlet tube 2 may be connected to a combustion chamber to provide a gaseous sample of a solid. Such a combustion chamber can be formed utilizing a thermo-electric heating element in a chamber holding the sample or can utilize a conventional combustion chamber used in mass spectrometer.

The gas sample is pulled into and through the system via operation of pump 30. Initially a measurement of the total concentration of the subject gases is conducted. In an embodiment for measuring carbon isotopes, IRGA 4 provides the total $CO_2$ concentration of the input sample without the need for preprocessing or conditioning. In additional embodiments targeted for harsh environments, a preconditioning unit may be added to remove moisture, dust etc. This can be accomplished, e.g., by filter units utilizing selective membranes to remove unwanted constituents as known in the art or utilizing chemical scrubbers as is known in the art.

The system then passes the constituent gases to one or more optional preconditioning units to remove certain constituent gases and to concentrate the gas or gases of interest. For instance, in some embodiments for determining the concentration of carbon isotopes, isotope ratio analyzer 24 is capable of providing the carbon isotope ratios, but is subject to interference by the presence of oxygen within the sample. Therefore in the previously discussed embodiments (as depicted in FIGS. 7, 8 and 9), the sample conditioning unit 18 is used to at least remove oxygen from the sample gas before it enters the isotope ratio analyzer 24. The precision of the measurement provided by the isotope ratio analyzer 24 can be further improved by increasing the concentration of the desired species within the sample. In some embodiments directed to $CO_2$ detection, concentration is increased to 1% or more by volume. In addition, the precision can be improved by supplying an inert carrier into the sample stream. Again, with reference to certain $CO_2$ units, the sample containing 1% $CO_2$, is mixed with pure nitrogen or another inert and non-interfering carrier gas. Therefore, the isotope ratio measurements provided by the isotope ratio analyzer 24, representing for example three laser cells of $^{12}C$, $^{13}C$ and $^{14}C$, can be improved by a sample conditioning unit 18 by concentrating the particular specie or species in the subject gas sample and by mixing it or them with a carrier gas.

The input sample is next passed to one or more isotope analyzers to detect the various isotopes of the subject gases in the sample. The isotope ratio analyzer can utilize any device for measuring the isotopic composition of a gas, but in some embodiments the system utilizes a low mass, low power, compact device. For a system measuring carbon isotopes, one such carbon 13 isotope analyzer is taught in U.S. Pat. No. 5,394,236. In additional embodiments, for instance an embodiment for detecting carbon 14, the system utilizes a coherent light source emitting energy to resonate selectively for desired subject gas. For instance, measuring isotopic carbon 14 would utilize a $^{14}CO_2$ isotopic laser for radiating the sample and a known standard reference cell containing the subject gas, here carbon 14. The ratio measurements may thus be conducted in a manner as taught in U.S. Pat. No. 5,394,236, whose teachings are herein incorporated by reference. In cases where both $^{13}C$ and $^{14}C$ are analyzed, both must be normalized to $^{12}C$, the most abundant form of carbon. Once the analysis is complete, the sample gases are evacuated from the system into the environment, typically in direction away from the input area.

Variations of the basic system are available. For instance, an expansion upon the basic system is possible by combining a number of the basic building blocks into a single unit to detect additional species and isotopes. In this case, a number of isotope ratio analyzers 24 are utilized. Each analyzer 24 would detect the presence of an isotopic species in the sample. Because the system does not consume the sample during detection, it is possible to sequentially arrange a number of detectors to receive the sample over time. Each ratio analyzer 24 could optionally include a preconditioning unit to condition the sample prior to isotopic measurements. In this series configuration, care is given to ensure that preconditioning units do not remove desired subject gases prior to analysis. An alternative architecture is to utilize a splitter to send a portion of the sample to each analyzer in parallel, thus allowing the ratio analyzers to operate independently. In either configuration, each analyzer could be operated selectively (i.e., only measure certain isotopic samples at certain times to reduce power consumption).

In certain embodiments, the system is designed to operate in remote locations, and/or to measure and monitor additional external conditions (e.g., temperature, humidity, wind direction, time, general weather conditions, etc) via conventional sensors mounted externally to the system. The complete unit is under the control of data acquisition and control unit 8.

Combined $^{13}CO_2$ and $^{14}CO_2$ Analyzer

A brief overview of the isotopic species and data rate for $CO_2$ are presented in Table 1 below. Definitions and estimates of the data rate for current technology and for an embodiment of the technology disclosed herein are provided, illustrating lack of isotopic data resulting from traditional isotope ratio mass spectrometry (IRMS) technology, and the promise of a much increased data rate employing an embodiment of the technology disclosed herein, the Global Monitor Platform (GMP).

TABLE 1

| | SPECIES FOR DECONVOLUTION OF FOSSIL AND NATURAL $CO_2$ SOURCES | | | |
|---|---|---|---|---|
| SYMBOL | DEFINITION AND USE | DESIRED PRECISION | TECHNOLOGY/DATA RATE | |
| T | the $CO_2$ volume mixing ratio expressed in ppm and on a WMO mole fraction scale | 0.1 ppm | LI-COR/ continuous Infrared gas analyzer, Li-COR. Inc. | LI-COR-GMP/continuous |

TABLE 1-continued

SPECIES FOR DECONVOLUTION OF FOSSIL
AND NATURAL $CO_2$ SOURCES

| SYMBOL | DEFINITION AND USE | DESIRED PRECISION | TECHNOLOGY/DATA RATE | |
|---|---|---|---|---|
| $\delta\ ^{13}C$ | the per mille deviation of the $^{13}C/^{12}C$ ratio from the VPDB primary standard and on the Vienna-PDB scale (Coplen et al, 1995; Allison et al. 1995). | <0.1‰ | IRMS/500 yr$^{-1}$ (NOAA Flask Sampling Program) | GMP/500,000 yr$^{-1}$ |
| $\delta\ ^{14}C$ | the per mille deviation of the $^{14}C/^{12}C$ ratio from the standardized value of the pre-bomb atmosphere in 1950 (Stuiver and Polach 1977) | <2‰ | AMS/500 yr$^{-1}$ (NOAA Flask Sampling Program) | GMP/500,000 yr$^{-1}$ |

The rare forms of carbon dioxide employed herein include $^{13}C^{16}O_2$ and $^{14}C^{16}O_2$. The multi-isotopic approach employed here may also be applied to all of the isotopologues of $CO_2$ including $^{12}C^{18}O^{16}O$, $^{13}C^{16}O^{18}O$, $^{12}C^{17}O_2$, $^{12}C^{18}O_2$, $^{13}C^{18}O_2$, $^{14}C^{18}O_2$ Freed 1995, Bradley et al., 1986). Although atmospheric $CO_2$ is used as an example here, any gas that can be generated and measured from any source is applicable (FIG. 5), for example, soil gases, gases generated in closed spaces, experimental chambers, and experimental apparatus or on other planetary surfaces. Some of these gases may include, but are not limited to: methane, nitrous oxide, molecular oxygen, hydrogen and nitrogen, water vapor and carbon monoxide.

According to certain embodiments, the GMP analyzer, referring to FIG. 4, is employed, including the following main components: three wavelength-tuned isotopic $CO_2$ gas lasers 501, 502, 503; RF-power supplies 510; a $CO_2$ calibration cell(s) 507; an air sample cell 508; low-pressure, low-flow gas handling hardware 511; diagnostic and control sensors 514; trap and drying components for sample preparation 511; a multi-channel signal analyzer 515; and a control computer and software 515. In the illustrated embodiment, the three wavelength-tuned isotopic lasers consist of $^{13}C$ 501, $^{12}C$ 502 and $^{14}C$ 503 lasers. However, any other wavelength-tuned isotopic laser may be used for any of the isotopomers of $CO_2$ or for any other relevant greenhouse gas such as $N_2O$ and $CH_4$.

The instrument may be packaged as a Class 1 laser system per the Food and Drug Administration (FDA) Center for Devices and Radiological Health (CDRH) requirements to cover the use of the $^{14}CO_2$ gas used for the $^{14}CO_2$ laser even though the amount of radiation contained in the laser cavity is less than background $^{14}C$ radiation. The instrument is to include a reference methodology, e.g., one or more reference gas cells, to allow detection ratios to be calibrated and correlated between multiple units independent of their physical location. In certain embodiments, external and satellite based reference cells and communications capabilities to report isotopic data and diagnostic information to a central location are to be incorporated into the integrated product.

In certain embodiments, a GMP analyzer measures the isotopic composition of $CO_2$ in the atmosphere based on the interaction of wavelength-specific laser energy within an ionized plasma volume. Referring to FIG. 13, this is accomplished in one embodiment utilizing the optogalvanic effect by inducing a change in the impedance of the plasma media through an optogalvanic effect (OGE). The impedance change, detected as a voltage change, can be correlated to the specific isotopic concentrations relative to the specific wavelengths of the excitation beams. In the case of the GMP analyzer, $^{12}CO_2$, $^{13}CO_2$ and $^{14}CO_2$ gas lasers permit the accurate detection of $12CO_2$, $^{13}CO_2$ and $^{14}CO_2$ isotopic concentrations and their ratios when wavelengths are tuned to the appropriate wavelengths.

Again referring to FIG. 13, according to certain embodiments, the basic configuration of the GMP unit consists of isotopic lasers, such as for $^{12}C$ 800, $^{13}C$ 801 and $^{14}C$ 802, mirrors, M1 to M7, a chopper to modulate the $^{14}C$ laser 810, three RF oscillators for excitation and a circuit board for detection and differential amplifier boards 803, 804, 805 contained within the laser units 800, 801 and 802, optogalvanic (OGE) standard reference cells 806, 807, 809, an OGE flowing gas sample cell 808 with 4 ZnSe windows allowing for $^{12}C$, $^{13}C$ and $^{14}C$ laser beams to interact with sample gases, sample gas drying and handling hardware consisting of a mass flow controller 811, a Nafion filter 820, a dry nitrogen gas tank or nitrogen generator 832, pressure sensors 813, 814 and a dry pump 823 from which the sample exits after analysis either in flow mode or in batch mode, a residual gas analyzer 812, standard gases for use in the flow cell 831, 824, a four port mechanical switching valve 819, single flow valves 816, 817, 818, oxygen scrubber 821, particulate filter 822, automated switching gas manifold valve 825, sample inlet ports 826, a piezo circuit for beam centering is employed in all three lasers leading to a master piezo circuit controller 827, a data acquisition board (DAQ) 828, a computer module (CPU) 829 and a telemetry system and antenna 830 and a power supply 833.

The three cell system referred to in FIG. 13 provides for the three laser beams to be suitably misaligned relative to each other to prevent back reflections propagating from the secondary laser output optical elements back into the primary laser cavity. This prevents instabilities in the laser outputs. While many embodiments of a system of systems disclosed herein are used for the simultaneous measurement of rare forms of carbon, the device may also serve as a platform to host related sensors. Small and lightweight sensors such as those for carbon monoxide, radon, methane, and other trace gases can further refine source and sink components for regional carbon budgets. Carbon monoxide is a key component of automobile exhaust (e.g., Levin et al., 2008). Methane can be indicative of both natural and anthropogenic sources (e.g., Levin et al., 2008). Radon is often used in conjunction with $^{14}C$ analysis (e.g., Levin et al., 2008). Other devices that may be placed on the unit include without limitation global positioning system GPS for location information, temperature, relative humidity and rain sensors.

Lasers and Optical Elements

In certain embodiments, the laser output energy is at a stable wavelength (line) that is consistent with the isotope of interest based on the quantum transition energy. Specific output wavelengths are 10.51-10.70 μm for $^{12}CO_2$, 11.06-11.26 μm for $^{13}CO_2$, and 11.8 μm for $^{14}CO_2$ (Freed 1980). Wavelength control of the lasers in the GMP unit is accomplished, e.g., with closed-loop feedback control of PZT elements (a piezoelectric ceramic material) for each laser (FIG. 13, 827) varying the laser cavity length. In one embodiment, the PZT elements are controlled with THORLAB's MDT 691 single channel piezoelectric drivers.

In certain embodiments, the laser output of the individual lasers is chopped at discrete frequencies to differentiate the OGE induced change in the output signal through Fourier transform methods. The chopping frequency of the $^{14}C$ and $^{13}C$ lasers is nominally 17 Hz and 25 Hz in one configuration. The laser beams are directed via coated silicon or copper mirrors into the OGE cells. ZnSe is used for the OGE cell windows 806, 807, 808 and 809.

Detection Cells and Sample Preparation

In certain embodiments, as shown in FIG. 13, 4 OGE detection cells are used in the isotopic detection system. A sealed cell contains a standard reference isotopic $^{12}CO_2$ composition 806, a $^{13}CO_2$ standard reference cell 807, a $^{14}C$ standard reference cell 809 and a sample flow cell 808. These cells use pressures of approximately 3.5-4.0 torr. The sample gas cell uses a flow rate of approximately 0.4 sccm.

Stable performance of the OGE cells involves humidity control of the gases. For the standard reference cell this is accomplished by controlling the gas sealed in the cell. In contrast, the sample gas handling system includes gas drying capabilities 820 (FIG. 13). The water vapor content tolerance on the sample gas is less than 1.5% relative humidity in the sample in one embodiment utilizing gas filled isotopic lasers and optogalvanic detection approach. Referring to FIG. 13 plasma fields are generated in the gas volumes in the OGE cells seen as a glowing discharge in both the sample 808 and reference cells (806, 807, 809), with RF power supplied by the RF driving boards contained in the lasers 803, 804 and 805 along with data acquisition boards.

Electronics and Control

Off the shelf components, well known to those skilled in the art of laser operation, can be used in the GMP unit for gas pressure 813, 814 (FIG. 13) and flow measurement and control 811 (FIG. 13), PZT element control for all three lasers 827 (FIG. 13), power supplies, data acquisition boards 803, 804, 805 (FIG. 13), temperature control, and software and computers 829 (FIG. 13). Features of these components are only based on satisfying the requirements of the GMP unit for specific applications.

The integrated laser systems in one embodiment with $^{13}C$, $^{12}C$ and $^{14}C$ lasers will therefore have three isotopic laser beams chopped at discrete frequencies propagating through the detection cells. Such an integrated system, in one embodiment, also accounts for the relative magnitude of the concentration of the $^{14}CO_2$ isotope in the atmosphere versus the $^{12}CO_2$ and $^{13}CO_2$ concentrations. Atmospheric air consists of approximately 0.03% $CO_2$. $^{13}CO_2$ constitutes approximately 1% of the composition within this 0.03%. In contrast, $^{14}CO_2$ constitutes approximately 1 part in $10^{12}$ within the 0.03%. Today the $1.18 \times 10^{-12}$ concentration of $^{14}CO_2$ in the atmosphere is called 1 modern level concentration and is the basis for scientific comparison of $^{14}C$ levels. The detection of such small quantities of $^{14}CO_2$ requires a much higher OGE signal gain for the $^{14}CO_2$ than the $^{12}CO_2$ and $^{13}CO_2$. Thus, two ranges of detection, data analysis and data summary must be accommodated. However, to one skilled in the art of laser systems, this issue can be overcome by appropriate adjustments in laser power, laser cavity length and time period of data acquisition for a given sample and can be determined by conducting a series of experiments controlling for specific factors of interest.

One solution to the relative difference in isotope concentration has been accounted for in US Patent Application Publication US 2008/0129994, incorporated herein by reference, showing a configuration of propagating multiple passes of the $^{14}CO_2$ laser beam through the OGE cell situated within the standing wave of the $^{14}CO_2$ laser cavity. This design interpretation has demonstrated detection limits approaching $10^{-15}$ $^{14}C/^{12}C$ in published reports (Murnick et al., 2008) which are similar to accelerator mass spectroscopy (AMS).

The noted concentration differences of the isotopologues impact in several ways. First, the optical design of the system accommodates single pass beam excitation in the sample OGE for the $^{12}CO_2$, $^{13}CO_2$ and $^{14}CO_2$ detection and standing wave beam propagation for the $^{14}CO_2$ detection. One embodiment as shown in FIG. 13 is to have one sample OGE cell for detection of all three carbon species $^{12}C$, $^{13}C$ and $^{14}C$. This is accomplished by splitting the $^{12}C$ beam with M4 allowing a $^{12}C$ reference signal to pass through both the $^{13}C$ and $^{14}C$ cells such that the data can be normalized against $^{12}C$ and reported in the isotope ratio formula defined earlier. The small detection limits necessitate managing the detection signal-to-noise ratio including design features applicable to provide the higher signal fidelity.

An additional feature of this multi-isotopic embodiment is maintaining a stable detection signal. Specifically, it has been demonstrated that temperature fluctuations within the OGE cells, the lasers and the detection electronics manifest themselves as OGE signals similar to isotopic changes. Drifts in the wavelength of the laser output manifest themselves in a similar manner. Thus, the accurate temperature control of the lasers, the OGE cells and the electronics is provided for in the GMP and, while this is achieved in the laboratory, as referenced in various documents above, with a re-circulating chiller, one embodiment will feature advanced solid state thermal management as shown in elements 834, 835, 836 (FIG. 13). In summary, a multi-isotopic analyzer according to certain embodiments includes a $^{12}C$, $^{13}C$ and $^{14}C$ embodiment as shown in FIG. 13. In such an embodiment certain components of the combined system may be shared, referring to FIG. 13, including the computer and software system 829, data acquisition boards 828, gas handling components including pumps 823, pressure sensors 813, 814, flow controller 811, sample dryer 820 and dry tank nitrogen gas or nitrogen generator 832.

Example Operation of a Carbon 12, 13, 14 Analyzer

As noted previously, isotopic analyzers based on optical detection systems have inherent limitations with respect to accuracy and precision for $^{13}C$ and have no capability for the analysis of $^{14}C$. One embodiment of the GMP analyzer includes the use of opto-galvanic analyzers for $^{12}C$, $^{13}C$ and $^{14}C$. However, the system of systems approach disclosed herein may be employed with any type of suitable analyzer for $^{12}C$, $^{13}C$ and $^{14}C$ isotopes. The aforementioned non-optical approach, the opto-galvanic approach, provides sensitivity to measure near 0% modern radiocarbon. This technique achieves specificity to isotopic chemical species via the use of the optogalvanic effect ("OGE"). The OGE can be measured with high signal to noise background ratios, and is proportional to laser power and is integrated over the discharge volume (Murnick and Peer 1994, whose teachings are herein incorporated by reference) and yield precision similar to that of the traditional mass spectrometers. The discharge is converted into an electrical signal and processed for a specified period of time, relative to a sealed standard gas chamber, depending on the required precision. Long measurement intervals, in principle, will exceed the precision typical of traditional isotope ratio mass spectrometers (i.e., <0.01 per mil). Advantages of OGE can be understood from the following equation (Murnick and Peer 1994):

$$S = nLI(v)A\sigma(v)C \qquad (1)$$

where the electrical response, S, of the system with laser of average intensity (Wcm$^{-2}$) I and frequency v is incident on a weak electrical discharge, n is the density of interaction species, L is the length of the interaction region, $\sigma$ defines the laser-species interaction cross section and C is an optogalvanic proportionality constant. Note that, according to (1) the signal is linear in both density [n] and laser power [I]. Increases in laser power provide for increased gain offering enhancement of signals for dilute or very low concentration of isotopes relative to the majority species. Improvement of signals by varying gas mixtures, gas pressure and discharge power are possible and affect the parameter C. Unlike absorption and fluorescence measurements dependent on optical elements, OGE reduces collection and dispersion optics and light transducers. Small discharge variations are canceled out by simultaneous measurement; the use of sealed working reference gases. As described previously (resulting in long life) promises to reduce instrument drift, off-sets between batches of standards prepared often (as is the case for traditional mass spectrometry) and differences between laboratories, which can be significant for the current flask sampling programs. Remotely operated units could process samples, e.g., for as long as one hour intervals throughout the day to achieve high precision for measurement of atmospheric $CO_2$ isotope ratios (i.e., <0.05‰) or, e.g., for as short as 1 second (yielding precision for $^{13}C$ and $^{18}O$ of at least about 0.01 and 0.1 ‰, respectively) for use in fast analytical schemes for plant physiological or biological monitoring. Samples can be analyzed in a semi-continuous batch mode or in continuous flow mode; each configuration may employ different hardware, as described in the embodiments previously. In particular, in one embodiment in the case of $CO_2$, three isotopic lasers are employed, one to determine the $^{12}C$ content, one to determine the $^{13}C/^{12}C$ ratios and an additional one to determine the $^{14}C/^{12}C$ ratio (Freed, C. 1990 whose teachings are incorporated by reference).

Example of Specific Operation

The operation of one embodiment of the instrument for this example is as follows. With reference to FIG. 6, under the control of the data acquisition and control unit 8, power is applied from power supply unit 14 to pump 30. Since the IRGA 4, sample conditioning unit 18, isotope ratio analyzer 24 and the pump 30 are all connected with coupling tubes 5, 7, 9 in order to provide a continuous gas flow path, gas present at gas inlet tube 2 is drawn through all of the tubing-coupled components and out of vent tube 33. After the gas has passed through the IRGA 4, it passes through the sample conditioning unit 18 before entering the isotope ratio analyzer 24. As the gas is drawn through the oxygen scrubber 36 (as shown in FIG. 7), which constitutes the sample conditioning unit 18 in this embodiment, oxygen is removed. The oxygen-free gas continues to be drawn through coupling tube 7 and into the isotope ratio analyzer 24. After sufficient gas has been drawn through the isotope ratio analyzer 24 to purge out any residual gas from a previous measurement, the data acquisition and control unit 8 stops the pump 30. Now that both the IRGA 4 and the isotope ratio analyzer 24 have received appropriate aliquots of the gas drawn in from the gas inlet tube 2, the data acquisition and control unit 8 initiates a concentration measurement of $CO_2$ by the IRGA 4 and an isotopic measurement of $CO_2$ by the isotope ratio analyzer 24. Measurement data generated by the IRGA 4 and isotope ratio analyzer is acquired and stored or transmitted by the data acquisition unit 8. The whole sequence of events can be repeated either immediately, or after a delay period as dictated by the program loaded into the data acquisition unit 8.

Operation of the embodiment with the sample conditioning unit 18 comprising the apparatus shown in FIG. 8 is as follows. Initially, solenoid valve 60 and flow-controlling valve 54 are closed allowing no gas to flow through them. Under the control of the data acquisition and control unit 8 (see FIG. 6), the solenoid valve 60 is opened and power is applied from power supply unit 14 (see FIG. 6) to pump 30 (see FIG. 6). Gas present at gas inlet tube 2 (see FIG. 6) is drawn into and through the IRGA 4 (see FIG. 6), through the coupling tube 5 (see FIG. 6), through the gas inlet tube 40, through the gas chamber 42 and through the solenoid valve 60. The gas continues to be drawn through coupling tube 62, coupling tube 29 (see FIG. 6), pump 30 (see FIG. 6) and finally out of the vent tube 33 (see FIG. 6). The gas selective membrane 46 provides considerable resistance to the gas flow and so does not allow a significant amount of sample gas to pass through it during this stage of operation. When enough gas has been drawn through the IRGA 4 (see FIG. 6) and the gas chamber 42 to purge any gas remaining from previous measurements, the data acquisition and control unit 8 (see FIG. 6) closes solenoid valve 60. Since the IRGA 4 (see FIG. 6) has received a suitable aliquot of sample gas, the acquisition and control unit 8 (see FIG. 6) initiates a $CO_2$ concentration measurement. The pump 30 (see FIG. 6) continues to run and establishes vacuum conditions in the isotope ratio analyzer 24 (see FIG. 6), coupling tubes 7, 9, 29 (see FIG. 6), gas outlet tube 56, and coupling tube tee 48. When the pump 30 (see FIG. 6) has run long enough to achieve the desired vacuum in the attached components, the acquisition and control unit 8 (see FIG. 6) stops the pump 30 (see FIG. 6). The $CO_2$ in the sample gas contained in the gas chamber 42 now permeates the gas selective membrane 46 due to the pressure difference across it.

The $CO_2$ in the sample gas contained in gas chamber 42 is allowed to permeate the gas selective membrane until enough $CO_2$ has accumulated in the evacuated components to provide precise isotope ratio measurement when mixed with an appropriate amount of carrier gas, e.g., pure nitrogen gas. Under the control of the data acquisition and control unit 8 (see FIG. 6), the flow-controlling valve 54 is opened enough to allow a charge of pure nitrogen gas to flow from the carrier gas source 50, through coupling tube 52. The nitrogen passes through coupling tube tee 48, through gas outlet tube 56, through coupling tube 7 (see FIG. 6) and into the isotope ratio analyzer 24 (see FIG. 6). Most of the $CO_2$ which had previously permeated the gas selective membrane 46 FIG. 8 is carried by the nitrogen gas flow into the isotope ratio analyzer 24 (see FIG. 6). The flow-controlling valve 54 is closed by the data acquisition and control unit 8 (see FIG. 6) when a suitable charge of gas is present in the isotope ratio analyzer 24 (see FIG. 6). At this time, the data acquisition and control unit 8 (see FIG. 6) initiates an isotope measurement of the $CO_2$ in the isotope ratio analyzer 24 (see FIG. 6). Measurement data generated by the IRGA 4 (see FIG. 6) and isotope ratio analyzer 24 (see FIG. 6) is acquired and stored or transmitted by the data acquisition unit 8 (see FIG. 6). The whole sequence of events can be repeated either immediately, or after a delay period as dictated by the program loaded into the data acquisition unit 8 (see FIG. 6).

Operation of another embodiment with the sample conditioning unit 18 comprising the apparatus shown in FIG. 9 is as follows. Initially, solenoid valve 66 and flow-controlling valve 72 are closed allowing no gas to flow through them. Under the control of the data acquisition and control unit 8 (see FIG. 6), the solenoid valve 66 is opened and power is applied from power supply unit 14 (see FIG. 6) to pump 30 (see FIG. 6). The data acquisition and control unit 8 (see FIG. 6) also sets the cryogenic trap 82 into the non-trapping state so that gas can flow freely through the cryogenic trap.

Next, gas present at gas inlet tube 2 (see FIG. 6) is drawn into and through the IRGA 4 (see FIG. 6), through the coupling tube 5, through the gas inlet tube 64 and through the solenoid valve 66. The gas is then drawn through coupling tube tee 68, cryogenic trap 82 and through the gas outlet tube 84. The gas flow then continues through the coupling tube 7 (see FIG. 6), isotope ratio analyzer 24 (see FIG. 6), coupling tube 9 (see FIG. 6), pump 30 (see FIG. 6), and out through the vent tube 33 (see FIG. 6). When enough gas has been drawn through the cryogenic trap 82 to purge any gas remaining from a previous measurement, the data acquisition and control unit 8 (see FIG. 6) sets the cryogenic trap 82 into the trapping mode. Gas continues to flow from the gas inlet tube 2 (see FIG. 6) all the way through the tubing-coupled components while condensable gas components are cryogenically trapped in the cryogenic trap 82. When gas has been flowing for a long enough time to allow an appropriate quantity of $CO_2$ to accumulate in the cryogenic trap 82, the data acquisition and control unit 8 (see FIG. 6) closes solenoid valve 66 and allows the pump 30 (see FIG. 6) to establish vacuum conditions in the coupling tube tee 68, cryogenic trap 82, outlet tube 84, coupling tubes 7 and 9 (see FIG. 6) and isotope ratio analyzer 24 (see FIG. 6). The data acquisition and control unit 8 (see FIG. 6) now initiates a concentration measurement on the aliquot of gas contained within the IRGA 4 (see FIG. 6). When the pump 30 (see FIG. 6) has continued to run for long enough to achieve its ultimate vacuum in the attached components, the acquisition and control unit 8 (see FIG. 6) stops the pump 30 (see FIG. 6) and sets the cryogenic trap 82 back to its non-trapping state in order to release the trapped gas. As the gas is released from the cryogenic trap 82, it expands throughout the components previously under vacuum. When enough time has expired to allow the trapped sample to completely evaporate, the data acquisition and control unit 8 opens the flow-controlling valve 72 to allow the carrier gas, preferably pure nitrogen, from the carrier gas source 74 to flow through it. The nitrogen gas flows from the flow-controlling valve 72, through coupling tube tee 68, through the cryogenic trap 82, and out through the outlet pipe 84. The nitrogen flows through coupling tube 7 (see FIG. 6) and into the isotope ratio analyzer 24 (see FIG. 6) carrying most of the previously trapped sample gas with it. The flow-controlling valve 72 is closed by the data acquisition and control unit 8 (see FIG. 6) when the desired charge of gas is present in the isotope ratio analyzer 24 (see FIG. 6). Then, the data acquisition and control unit 8 (see FIG. 6) initiates an isotope measurement of the $CO_2$ in the isotope ratio analyzer 24 (see FIG. 6). Again, measurement data generated by the IRGA 4 and isotope ratio analyzer 24 is acquired and stored or transmitted by the data acquisition unit 8. The whole sequence of events can be repeated either immediately, or after a delay period as dictated by the program loaded into the data acquisition unit 8.

The operation of an embodiment of the cryogenic trap apparatus 82 shown in FIG. 10 (together with the sample conditioning unit 18 of FIG. 9), is as follows. With the liquid nitrogen dewar 112 filled to approximately 75% capacity, the data acquisition and control unit 8 (see FIG. 6) can control the temperature conditions of the U tube 108, in order to either cryogenically trap a gas sample which is condensable at liquid nitrogen temperatures, or thaw a previously trapped sample.

Under the control of the data acquisition and control unit 8 (see FIG. 6), when a sample is to be trapped, solenoid valve 102 is opened and no current is passed through the resistance heater wire 106. This action allows any nitrogen gas or air trapped in the upper part of cylinder 110 to escape through vent tube 100, through solenoid valve 102, and out of exhaust tube 104. The gas escaping from the upper part of cylinder 110, in turn allows the liquid nitrogen level in the cylinder 110 to rise to the same level as that of the dewar 112, thus immersing the lower part of the U tube 108 in liquid nitrogen. As long as these conditions exist, the U tube 108 will remain at liquid nitrogen temperatures and any gas flow through the interior of the U tube 108 will liquefy or freeze if it is condensable at liquid nitrogen temperatures. When a sample is to be thawed or when the non-trapping state is required, the data acquisition and control unit 8 (see FIG. 6) closes solenoid valve 102 and applies power to the resistance heater wire 106. The current passing through the resistance heater wire generates heat and starts to evaporate nearby liquid nitrogen. The nitrogen gas thus generated cannot escape from the upper part of the cylinder 110 since solenoid valve 102 is closed and the result is that the liquid nitrogen level inside the cylinder 110 is pushed down below that of the dewar 112. The liquid nitrogen level inside the cylinder 110 continues to be pushed down by the nitrogen gas until it is close to the bottom edge of the cylinder 110. As long as solenoid valve 102 remains closed and current passes through resistance heater wire 106, the liquid nitrogen level inside the cylinder 110 will remain below the U tube 108. The heat generated by the resistance heater wire continues to heat the U tube 108, providing enough energy to evolve any gases previously trapped in the interior of the U tube 108. The power applied to the resistance heater wire 106 by the data acquisition and control unit 8 (see FIG. 6) can be modulated in order not raise the temperature of the U tube 108 so high that it radiates excessive heat and boils liquid nitrogen unnecessarily.

The operation of an embodiment of a variable bellows apparatus 83 shown in FIG. 11 (together with the sample conditioning unit 18 of FIG. 6), and used in a batch mode embodiment is as follows. With the variable bellows 83 open to maximum extent, the data acquisition and control unit 8 (see FIG. 6) can control the volume of the variable bellows in order to reduce the sample size of a sample gas in which the concentration of $CO_2$ is too large, for example in the case of analyzing pure $CO_2$, and may not fall within the concentrations over which the analyzer has been calibrated. To one skilled in the art of gas handling for isotopic analysis this procedure is well understood (Werner and Brand 2001). However, in the present case, a number of calibration curves specifically for $^{14}CO_2$ and $^{13}CO_2$ over a range of concentrations of $CO_2$ in air, for example from $10^{-10}\%$ $CO_2$ to 100% $CO_2$, may be required. The use of the bellows to reduce the sample size to within the range of the most favorable accuracy and precision of the analyzer (e.g., $^{13}C$, $^{14}C$) is a convenient method for this purpose.

Initially, solenoid valve 66 and flow-controlling valve 72 are closed allowing no gas to flow through them. Under the control of the data acquisition and control unit 8 (see FIG. 6), the solenoid valve 66 is opened and power is applied from power supply unit 14 (see FIG. 6) to pump 30 (see FIG. 6). The data acquisition and control unit 8 (see FIG. 6) also sets the bellows 83 into the non-trapping state so that gas can flow freely through the cryogenic trap.

Next, gas present at gas inlet tube 2 (see FIG. 6) is drawn into and through the IRGA 4 (see FIG. 6), through the coupling tube 5, through the gas inlet tube 64 and through the solenoid valve 66. The gas is then drawn through coupling tube tee 68, bellows 83 and through the gas outlet tube 84. The gas flow then continues through the coupling tube 7 (see FIG. 6), isotope ratio analyzer 24 (see FIG. 6), coupling tube 9 (see FIG. 6), pump 30 (see FIG. 6), and out through the vent tube 33 (see FIG. 6). When enough gas has been drawn through the bellows 83 to purge any gas remaining from a previous measurement, the data acquisition and control unit 8 (see FIG. 6) sets the bellows 83 into the gas capture mode in which case switching valve is set to the closed position for both ports allowing the gas to expand into the bellows and associated pipe connections without being pumped away. After a period of time that is sufficient for the gas to equilibrate in the volume of the bellows, the control unit 8 (FIG. 6) is set to close the bellows by some amount so as to reduce the bellows total volume. At the same time piping volumes 68, 86 and 84 are open to vacuum to flush out any remaining gas.

After pumping for a suitable period valve 66, 72 are closed and fully evacuated. At this time the control unit 8 (FIG. 6) opens port to allow gas in bellows to expand into the piping volume. The control unit then provides for closure of the bellows valves and the system is pumped out as before reducing the sample size. The control unit 8 (FIG. 6) then proceeds to repeat the procedure until the sample gas pressure is consistent with pressures that are optimal for analysis and comparison with the relevant calibration curves. Then, the data acquisition and control unit 8 (see FIG. 6) initiates an isotope measurement of the $CO_2$ in the isotope ratio analyzer 24 (see FIG. 6). Again, measurement data generated by the IRGA 4 and isotope ratio analyzer 24 is acquired and stored or transmitted by the data acquisition unit 8. The whole sequence of events can be repeated either immediately, or after a delay period as dictated by the program loaded into the data acquisition unit 8. Manipulation of sample gas pressures for analysis in a three cell system is a critical performance factor given the vast differences in concentration between $^{14}CO_2$ and $^{13}CO_2$.

In further embodiments, the sample gas mixture can be provided from liquid or solid samples. The solid and liquid samples are turned into a gas via heating or through combustion. The sample gas mixture can be provided from any one of a number of commercially available devices capable of generating gases from non-gaseous samples in order to facilitate gas concentration or gas isotope ratio measurements. For example, a Dumas combustion device such as the one manufactured by Carlo Erba could be connected to the gas inlet and the gas mixtures generated from the combustion of solid sample materials analyzed in a similar fashion to those previously described.

In further embodiments data captured by the device is transmitted via telemetry to one or more central locations for analysis and data summary. The data thus can be used to construct national, regional and state wide budgets or as the case may require. FIGS. 24-29 show international (EU), national US) and state wide grids as examples of device locations offering the capability of real-time, simultaneous measuring, monitoring, reporting and verification of $^{13}C$ and $^{14}C$ in atmospheric $CO_2$ all defined against a single standard common to all devices. FIGS. 16, 17 and 18 show embodiments in which devices in the field transmit data to a satellite or other means after which the data are analyzed and summarized to comply with voluntary and/or regulatory policies as well as for use in carbon trading platforms as described in FIG. 19.

Applications of the System of Systems

In certain embodiments, a novel reporting system for isotopically defined carbon emissions can be used in the context of greenhouse gas trading and carbon based financial instruments. The measured values for $^{13}C$ and $^{14}C$ of $CO_2$ can be used in conjunction with flow and volume measurements to derive a total emissions value for liters (moles) emitted $CO_2$ (and well known conversions thereof to C emissions units).

A Two Carbon Trading Paradigm: Applications of the System of Systems

In certain embodiments, a novel reporting system for isotopically defined carbon emissions can be used in the context of greenhouse gas trading and carbon based financial instruments. The measured values for $^{13}C$ and $^{14}C$ of $CO_2$ can be used in conjunction with flow and volume measurements to derive a total emissions value for liter (moles) emitted $CO_2$ (and well known conversions thereof to C emissions units, such as metric tons, $CO_2$ and carbon equivalent units). For example, in the case of measurement of isotopic values where total volumes (moles) from one or more sources can be calculated, then the respective percentages of biogenic and fossil fuel derived $CO_2$ can be known. In at least some embodiments, the monetization of emissions using a system of systems disclosed herein also reports the emissions data in a way that clearly designates the components of interest. For example, in a case where 80% of emissions are fossil fuel derived and 20% are biogenic derived, then as sourced by their respective isotopic components, one can designate such data as follows:

$^{14}C$ units: 80
$^{13}C$ units: 20

Thus, as the isotopic data are converted to volumetric and molar data, the same designation may be used to report metric tons of the respective components. For example, following from the above example, if the calculation of metric tons results in 800 for fossil fuel and 200 for biogenic carbon, respectively (the numbers are for illustration purposes only), then the units of carbon emissions may be reported as follows:

$^{14}C$ mt: +800
$^{13}C$ mt: +200

In the above designations, one can see the value in making explicit data for carbon emissions trading available as to the source of the carbon in question. Currently, emissions are typically estimated, thus, the changing components of fossil and biogenic $CO_2$ are not currently included in trading mechanisms.

The above approach will be useful in designating the sequestered carbon in forest activities, for example. By way of illustration, sequestered carbon may be quantified as follows:

$^{14}C$ mt: −200
$^{13}C$ mt: −600

In the above example, the data clearly indicate the forest in question has drawn down some 200 metric tons of fossil fuel derived $CO_2$ and some 600 tons of biogenic derived $CO_2$. Representing carbon emissions and sequestration data in this way for all carbon units could add considerable value to the units of carbon and provide new dimensions in pricing.

In the cases as described above, designations as suggested could be derived over any time period and over any spatial scale (according to the placement of multi-isotopic units across the space in question), rendering values directly compatible with the "metric tons carbon" and metric tons "carbon equivalent" units used in all carbon trading platforms to date. Thus, a system of systems according to certain embodiments offers a new way to monetize carbon emission and sequestration data based on actual measurements. The multi-isotopic approach used here provides for a novel way to report carbon emission data (either as sink or source), offering new dimensions in carbon pricing, carbon trading and greenhouse gas policy considerations.

In summary, a laser based system of systems for both $^{13}C$ and $^{14}C$ offers many benefits over the traditional IRMS and AMS methods. Most importantly, samples can be analyzed and referenced to an instrument standard(s) in situ—there is no need for transport of gas sample to central laboratories. Secondly, the sample is measured as free $CO_2$ in air and does not require a cryogenic collection step, thus the sample is analyzed in a non-destructive manner and may be repeatedly analyzed and/or analyzed for longer periods of time to increase data collection and statistical certainty. Thirdly, the data for $^{13}C$ and $^{14}C$ can be compared with a variety of standards in a single instrument, or external to the instrument, and also can be compared with ensembles of instruments in any location around the world, instantaneously, ensuring comparability across all samples regardless of location. As disclosed herein, the fabrication of large numbers of sealed reference cells can be made according to methods that are familiar to those skilled in the art of making $CO_2$ gas filled lasers such as those produced by Access Lasers, Inc., CA, or LTG-Lasertech, Concord, ON. Thus, referring to FIG. 12 the use of sealed-cells that contain or can be made to contain the same standard gas and employed in large numbers of instruments vastly improves reference gas statistics compared to reference systems of typical isotope ratio mass spectrometers and accelerator mass spectrometers. The near-simultaneous acquisition of reference data and unknown data also provides short and long term stability of analyzer signals.

Again referring FIG. 12, the laser based spectroscopy approach also permits an optional hierarchal verification of instrumental standard sealed cell performance by comparison with sealed cells containing a variety of standard gases external to the actual data producing multi-isotopic analyzers. External instruments or modules that contain only primary sealed cell references can be in a single, double or triple cell configuration and would operate essentially like their multi-isotopic analyzer counterparts that also contain flow-through sample cells for analysis of unknowns. Because the external reference cell unit does not contain sample cells, but is otherwise equipped with data collection and telemetry features, the external reference unit can be used to compare reference signals and baseline signals with any other multi-isotopic analyzers by telemetric communication. Additionally, a series of standard cells for both $^{13}C$ and $^{14}C$ and the appropriate lasers could be deployed as a payload aboard satellites communicating with ensembles of instruments around the world. Such an arrangement of satellite based and ground based systems that are locked into standard reference frameworks offer capability to structure live trading of instantaneous carbon credits as data are collected in a real-time analytical and reporting mode. Additionally, such satellite configurations for the $^{13}C$ and $^{14}C$ standards and data collection could also be used to cross-compare data collected by greenhouse gas observing satellites for carbon emissions and other greenhouse gases (e.g., Orbital Carbon Observatory) with ground based measurements as proposed herein. Thus, an instrumental approach that reduced isotopic fractionation, provided for stable and homogeneous standards across time and space and that carried out analyses in situ that are referenced with external standards linked in a global network would be highly desirable for reliable and transparent baseline data for all carbon trading platforms as well as offer the potential to integrate and compare space-based observations of carbon emissions.

The following examples are illustrative and not limiting.

Example 1

Forest Trading

Figure 23:
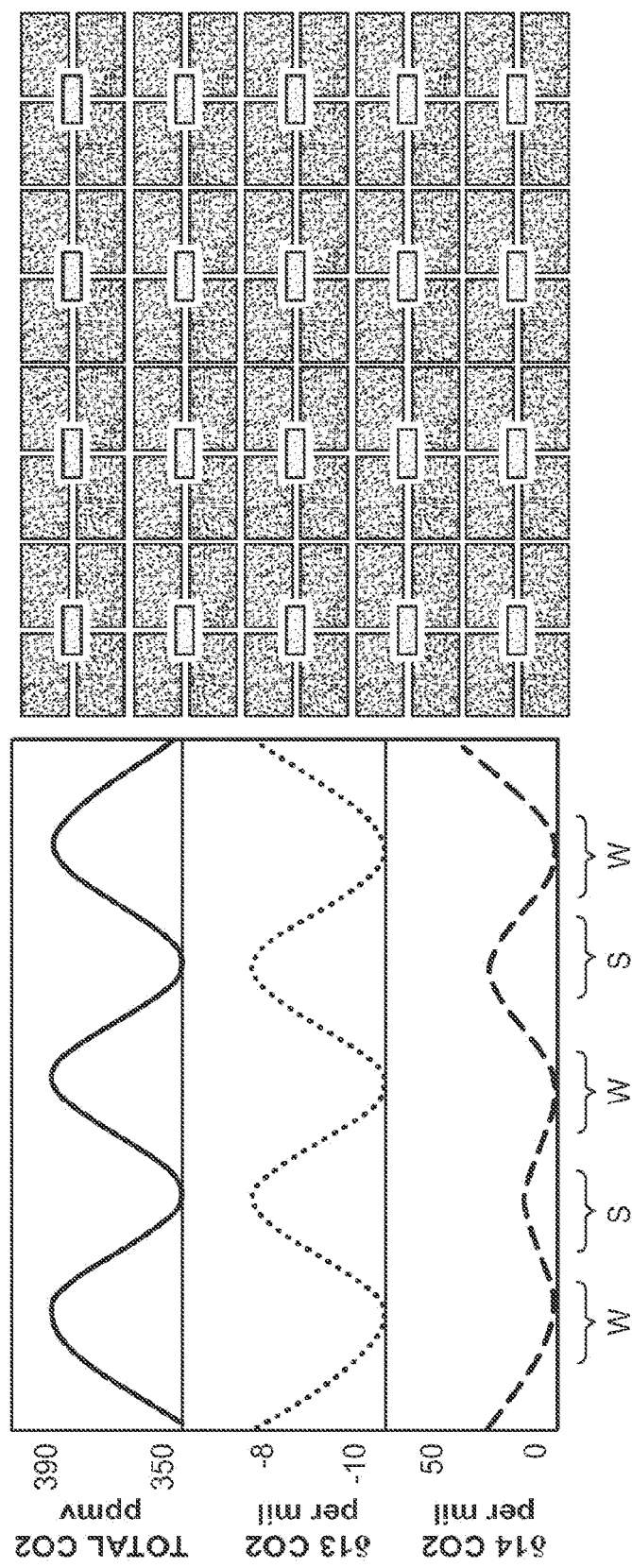
FIG. 23 shows an example of a use of the system of systems to measure, report, verify and provide for carbon exchanges within an array of devices placed in a forest setting over 2.5 years according to season. Hypothetical carbon fluxes for $CO_2$ total concentration, $^{13}CO_2$ and $^{14}CO_2$ ratios are also shown.

Referring to FIG. 23 an example application of the system of systems is provided. While numerous locations within forests are measured and monitored for $CO_2$ concentration, isotopic composition to determine and quantify source terms for $CO_2$ to support carbon trading has not been reported. Specific cases are used herein for illustration.

Currently, forest carbon flux is estimated using a variety of forestry algorithms such as described previously by the Chicago Climate Exchange (CCX, www.ccx.com). However, research projects quantify carbon exchange on a limited basis. By way of background one of the projects is briefly described. The forest measured and monitored for carbon flux in this example is described in Barford, et al., 2001, and presents an opportunity to apply the system of systems to real data for forest carbon flux but lacking isotopic data to identify and quantify sources of $CO_2$. The site, located in western MA, is equipped with a tall tower extending 30 m from the ground and equipped with appropriate instrumentation. The eddy covariance technique, known well to those skilled in the art, is used to measure fluxes of $CO_2$, momentum, and sensible heat and latent heat at 8 levels. Isotopic data acquisition is selected to match the acquisition rates of high frequency transport flux of the atmosphere. The use of the eddy covariance technique imposes considerable technical difficulties on isotopic instrumentation including (e.g., Salesk et al., 2006): 1) rapid response time (<1 second for analysis of $^{13}CO_2$), 2) sensor stability allowing continuous measurements without baseline drift enabling capture of the low-frequency wind transport flux, 3) high precision such that small variations in the eddy flux isotopic signal can be resolved. The corresponding units for carbon isotopic eddy flux are given as ppm meters $s^{-1}$ per mil. Such measurement challenges for isoflux are on the order of <0.1 per mil, standard deviation of 10 second integration times, along with stable baseline data. The aforementioned eddy covariance approach must operate 24 hours a day throughout a period of one year to obtain a net flux of carbon in a given forest area. In this way, winter release of $CO_2$ via respiration is compared to summer draw down of $CO_2$ by photosynthesis: the net difference will determine if the forest is a sink (i.e. negative number) or a source (i.e., positive number). Thus, accurate and reliable forest flux data that could be used for carbon trading can be obtained using a highly demanding set of instrument function and software protocols. According to the data of Barford et al. (2001) over a period of 8 years the forest sequestered approximately 2 megagrams or metric tons of carbon per hectare, however, no correction is made for the presence of fossil fuel $CO_2$ that was taken up by plants and measured as part of the routine measurements for concentration, thus representing an unknown error. In the case in which this is used to price and trade carbon in metric tons, then, an unavoidable and unknown uncertainty exists. The Barford et al. (2001) data were collected with a small footprint tower of approximately 30 meters in height being sufficient to be above the canopy. A series of tower heights is desirable as the taller the tower the larger the footprint.

The measurement approach and methods used in this study suggest that the footprint of the Barford et al. (2001) data represent some 100-200 hectare. We take the lower case of 100 hectares as an example, meaning that the 100 hectares are defined by property lines or other means. According to the data, approximately 16 megagrams accumulated over the 8 year period resulting in 16 metric tons per hectare of sequestered carbon. If a metric ton of carbon were traded at the end of the eight year period for $20 per ton then the owner of the land would have credits worth $32,000. However, if the uncertainty was 10% then the pricing could be over or under priced by $3,200. Thus, without the use of a $^{14}C$ and $^{13}C$ analyzer, there is no way to disentangle fossil fuel contributions from natural and plant based contributions. When considering 10's to 100's of millions of acres potentially involved in carbon trading one can see that economically significant errors are present. The data for Barford et al., (2001) clearly demonstrate that yearly net flux data are required as the values for each year can be significantly different. For example, the year 1998 of the Barford et al. (2001) data show that carbon sequestration (net carbon uptake $MgC\ ha^{-1}\ yr^{-1}$) was reduced by 2.4 megagrams compared to the preceding year of 1997. The record reported by Barford et al. (2001) shows from 0.2 to 2.4 Mg variation across a measurement period from 1993 to 1999. Thus, this data set along with others (e.g., Scott et al., 2004) illustrate the need for full measurement of forest carbon flux with fine time resolution to allow eddy covariance applications and to ultimately provide carbon storage data that highly reliable, inter-comparable with other projects and have a defined uncertainty of approximately $<0.1\ MgC\ ha^{-1}\ yr^{-1}$.

According to the data of Scott et al. (2004) use of eddy covariance methods may also be used to establish criteria for carbon flux associated with harvesting of forest for the production of wood products (e.g., paper, wood building products). Since many forests may support a wood products industry the use of the eddy covariance technique can be used to ensure that carbon replacement by tree regrowth is attained. Thus, a simple mass balance of carbon lost after harvest and carbon sequestration after cutting over a period of years can ensure sustainability of the forests while allowing wood products inventory. The rate of tree regrowth will determine the time period required to replace the carbon removed. Thus, using the systems of systems and placing ensembles of analyzers in areas where forest harvest and re-planting takes place offers a unique method for establishing the carbon dynamics and associated pricing of forest credits under a variety of circumstances.

We note that errors associated with estimation methods as reported by Galik et al. (2009) with reference to the generation of forest carbon offsets are shown to be as high as 30%. The sensitivity of forest models according to Glaik et al. (2009) is related to the treatment of forest carbon components that are comprised of a number of carbon pools including above ground and below ground active components, forest litter and dead trees. The isotopic approach with eddy covariance described here includes the primary below ground and above ground biomass and their dynamic carbon uptake and release.

In one embodiment following on from the above example, we refer to FIG. 23 showing an array of 20 GMPs positioned across the landscape at 100 hectare grid lines. The GMP analyzes gases taken at several levels on towers or other structures allowing the eddy covariance application. Thus, using the example above as a reference, we take for illustration an eight year period in which each 100 hectare plot sequestered 16 metric tons of carbon. However, in this case the system of systems:

1) Provides $^{14}CO_2$ signal for fossil fuel $CO_2$, $^{13}CO_2$ signal for biogenic $CO_2$ and total $^{12}CO_2$ measured at a rapid rate of approximately 1 to 10 Hz ideally but also may be up to 100 Hz, allowing integration with eddy covariance methods.
2) Provides for an inter-calibrated network of analyzers to ensure comparable results for each device. Placement of GMPs will be such that dispersion on scales of 1 to 100 kilometers is within the detection range of the GMPs being 2 per mil for $^{14}C$ and 0.1 per mil for $^{13}C$. Initial testing with various placement patterns may be required to derive the optimal number and configuration of analyzers. Height of sample intakes should be at least several meters above the tree canopy, with some instruments being placed higher (e.g., 50 meters). A mix of tower heights may be used to discern wider areal carbon flux footprints. Towers utilized currently range from approximately 30 meters to a small number of tall towers at 400 meters.
3) Provides for a telemetry system to transmit data to a central location.
4) Provides for data analysis and model integration.

The data collected would then consist of $^{14}C$ and $^{13}C$ delta ratios and the $CO_2$ concentration. Hypothetical measurements are shown in FIG. 23 consisting of total $CO_2$ concentrations (solid line, top), delta $^{13}CO_2$ ratios (middle small dashed line) and delta $^{14}CO_2$ ratios (long dash line, bottom panel). Note that the $CO_2$ concentrations rise and fall according to the seasons (marked S for summer and W for winter). The total $CO_2$ concentration does not allow determination of the fossil fuel component. Moreover, as was demonstrated in FIGS. 1 and 2, $^{13}CO_2$ ratios also do not distinguish fossil fuel contributions to the carbon exchange and thus the net carbon gained or lost. The gain or loss then represents the carbon component that is either source or sink, or in trading terms, a carbon credit lost (source) or a credit gained (sink).

The signal frequency of 10 Hz is important for eddy covariance data. Data rates at longer than 1 second will not meet the requirement to match transport flux of wind and thus cannot be effectively used for eddy covariance preventing a high resolution and accurate record of carbon flux. Thus, one skilled in the art of such measurements will recognize that the widespread use of isotopic analysis with eddy covariance is restricted to a few sites with limited measurement times although networks of such towers where the eddy covariance method is used with $CO_2$ concentrations alone is approximately several hundred stations as part of the Fluxnet project (FLUXNET 2009), Thus, an application of the "system of systems" approach disclosed herein is recognized as much needed but as yet not implemented.

Thus, when $CO_2$ is drawn down in summer, as plants grow, the $^{13}CO_2$ ratios decrease due to a fundamental discrimination against the heavier $^{13}CO_2$ molecule. The trend in $^{14}CO_2$ may also become less positive since fossil fuel does not contain $^{14}C$ thus diluting the current $^{14}CO_2$ background. However, the raw data for each of the terms (total $CO_2$ concentration, $^{13}CO_2$ and $^{14}CO_2$ ratios) can be used in a series of calculations known to those skilled in the art to derive source data of fossil and biologically derived $CO_2$. As described previously, such simple treatment of isotopic data are not adequate to support carbon trading, lacking sufficient numbers of analyzers, inter-calibration and an appropriate model integration over a representative area. For illustration an example of a simple calculation deriving the fossil fuel component described by Levin, 2008 is provided:

To estimate regional fossil fuel $CO_2$ from measured $^{14}CO_2$ and $CO_2$ concentration one can use the following mass balance equations:

$$CO_{2\ measured} = CO_{2\ biological} + CO_{2\ background} + CO_{2\ fossil\ fuel}; \text{ and,}$$

$$CO_{2\ measured}(\delta^{14}C_{measured}+1000\permil) = CO_{2\ background}(\delta^{14}C_{background}+1000\permil) + CO_{2\ biological}(\delta^{14}C_{biological}+1000\permil) + CO_{2\ fossil\ fuel}(\delta^{14}C+1000\permil)$$

In the above equations, $CO_2$ measured is the observed $CO_2$ concentrations from the network of devices, $CO_2$ background represents the concentration of $CO_2$ at a reference clean air site (e.g., Globalview 2006), $CO_2$ biological is the regional biogenic component, and $CO_2$ fossil fuel is the fossil fuel component for the region of the measurements. The $^{14}C/^{12}C$ ratios of these components in the delta notation are respectively, delta $^{14}C$ measured, delta $^{14}C$ biological and delta $^{14}C$ fossil fuel. Delta $^{14}C$ is the ‰ deviation from the $^{14}C/^{12}C$ ratio from the NBS oxalic acid standard activity corrected for decay (Stuiver and Potlatch 1977).

Thus, solving for $CO_2$ fossil fuel yields the following equation:

$$CO_2 \text{fossil fuel} = [CO_{2\ background}(\delta^{14}C_{background} - \delta^{14}C_{biological}) - CO_{2\ measured}(\delta^{14}C_{measured} - \delta^{14}C_{biological})]/\delta^{14}C_{biological}+1000\permil.$$

For example, if the mean contribution of fossil fuels were determined to be 1 ppmv of the total $CO_2$ measured for the land within the array, then using the data from Barford et al., 2001, an error of approximately 10% would be unaccounted for amounting to 1,440 metric tons of $CO_2$ stored as opposed to 1,600 metric tons. On a dollar volume basis, a difference of $3,200 would have been in error. On larger scales such as those represented by states and over larger regions such errors will be compounded. For 2008, according to the reporting agency, Point Carbon (www.point.carbon.com) the total dollar volume of carbon trading representing all carbon financial instruments was approximately $129 billion US, primarily as a result of trading within the European Union. Thus, a 10% error, if representative, amounts to approximately $12.9 US billion dollars. The complexity of the data produced utilizing multi-isotopic analyzers is illustrated in FIG. 23 and clearly requires appropriate data-model integration to derive total carbon for the 100 hectare area. A system of systems as disclosed for the purposes of carbon trading requires integrated components at various scales from the analyzers to data analysis and synthesis as shown in this example.

Figure 24:
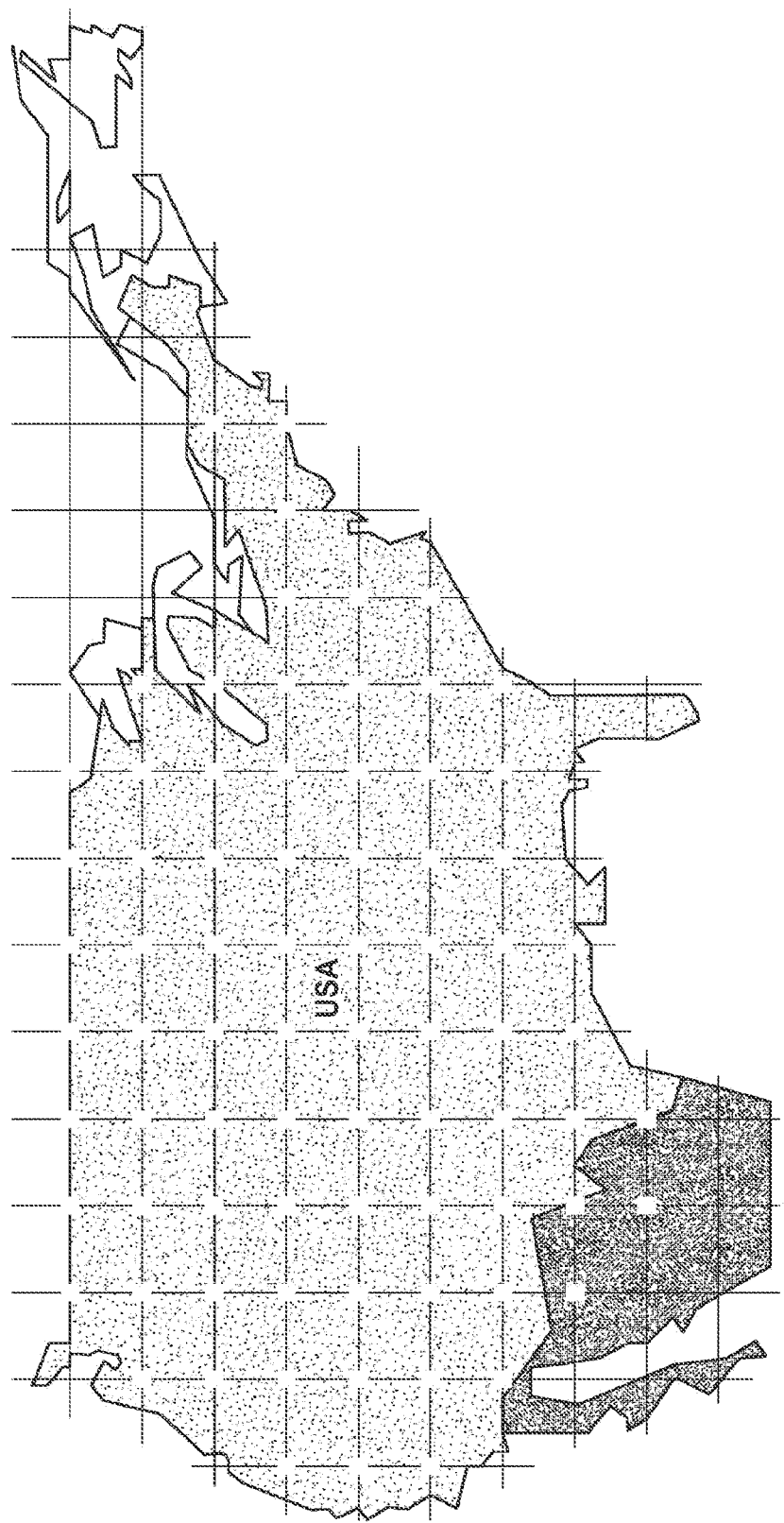
FIG. 24 shows an example of the use of a system of systems to measure, report, verify and provide for carbon exchanges across the continental US. Optional external primary reference standards may used according to state, regional and continental reporting goals.
Figure 25:
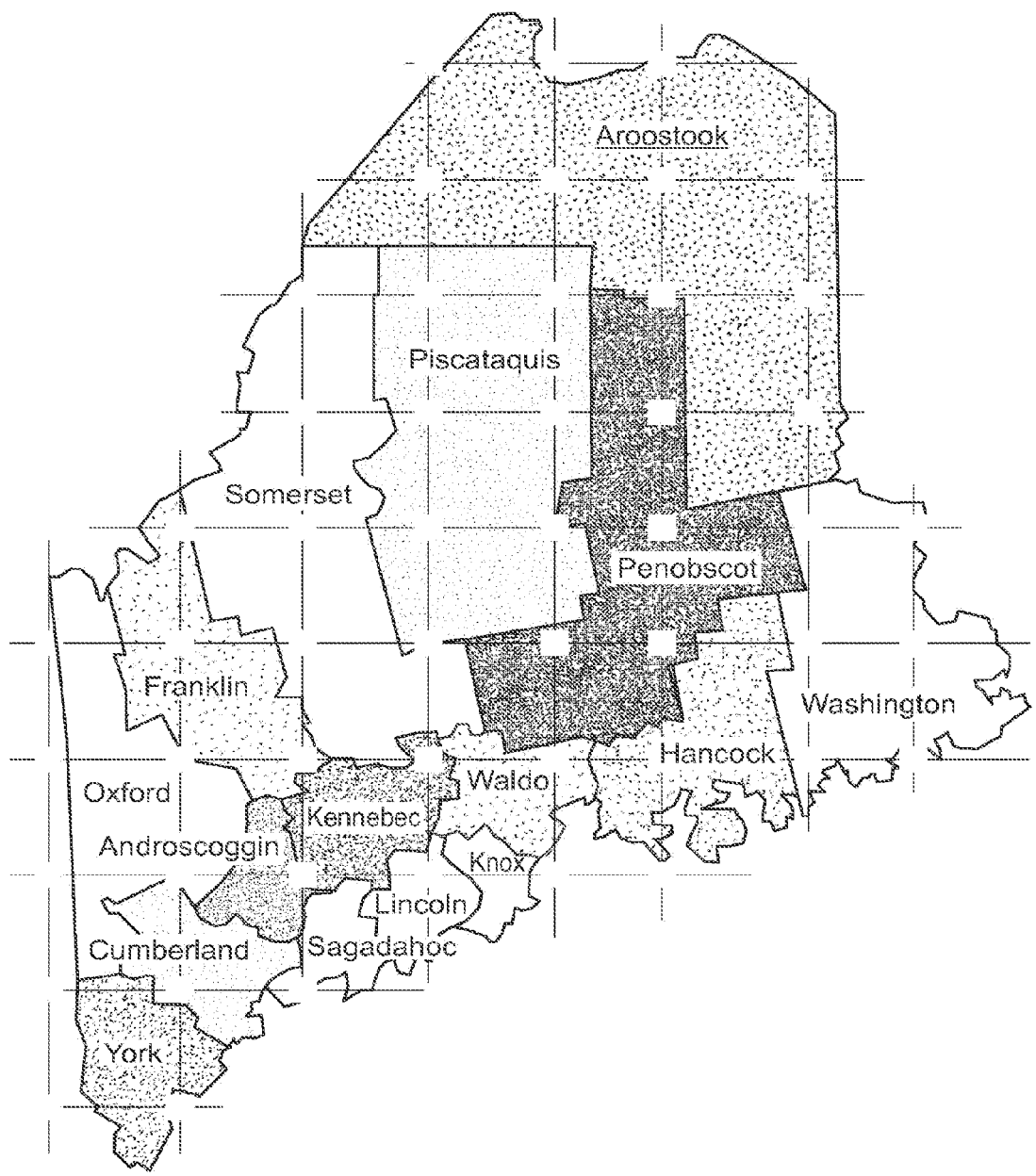
FIG. 25 shows an example of the use of a system of systems to measure, report, verify and provide for carbon emissions data for the state of Maine. Optional primary reference standards may be used as needed.
Figure 26:
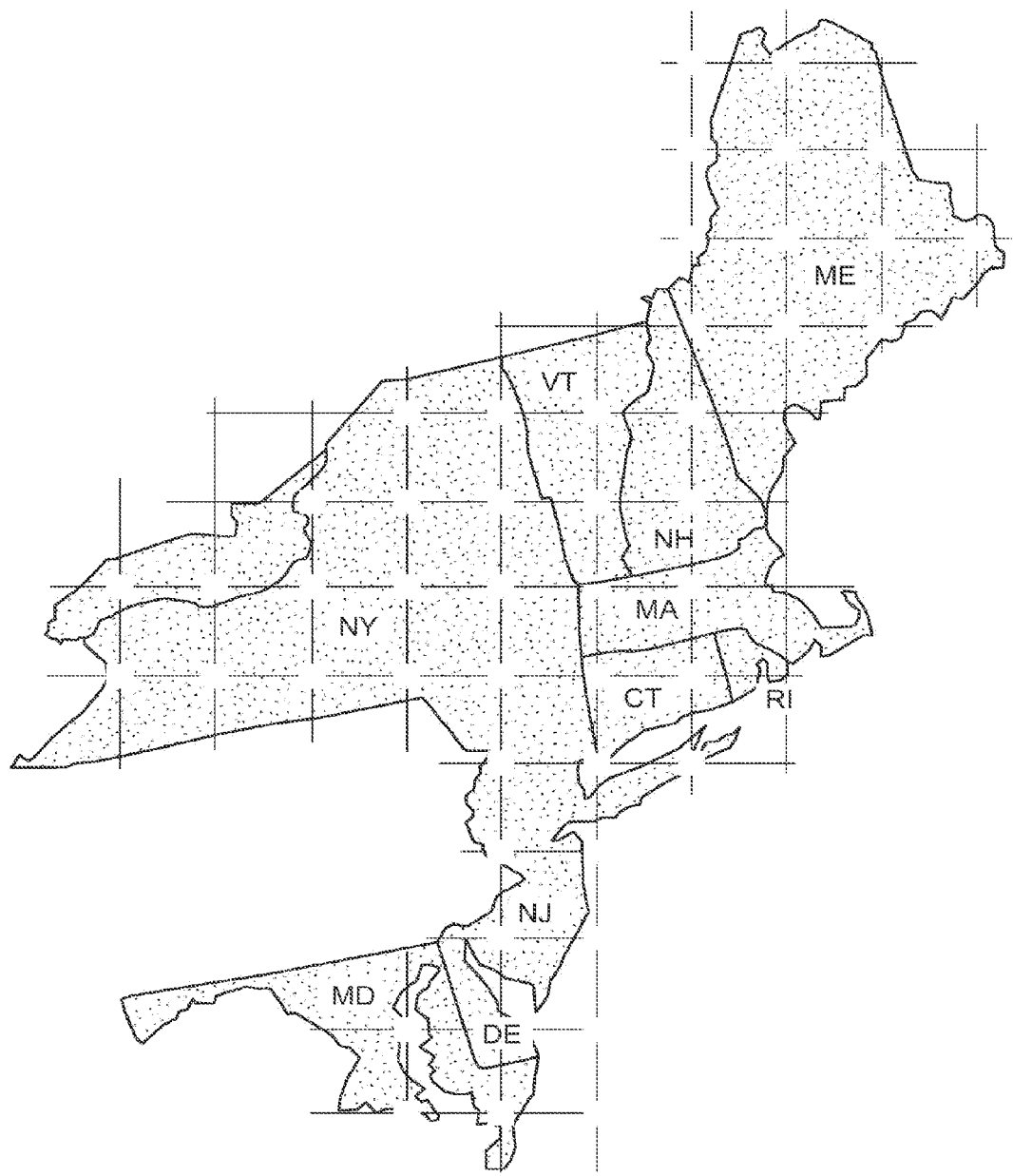
FIG. 26 shows an example of the use of a system of systems to measure, report, verify and provide for carbon exchanges for the Regional Greenhouse Initiative (RGGI) including the states of, Connecticut, Delaware, Maine, Maryland, Massachusetts, New Hampshire, New Jersey, New York, Rhode Island and Vermont. Optional external reference standards may be used as needed.
Figure 27:
FIG. 27 shows an example of the use of the system of systems to measure, report, verify and provide for carbon exchanges for the Midwest Greenhouse Gas Accord (2009) including the states of Iowa, Illinois, Kansas, Manitoba (Canada), Michigan, Minnesota and Wisconsin. Optional external reference standards may be used as needed.
Figure 28:
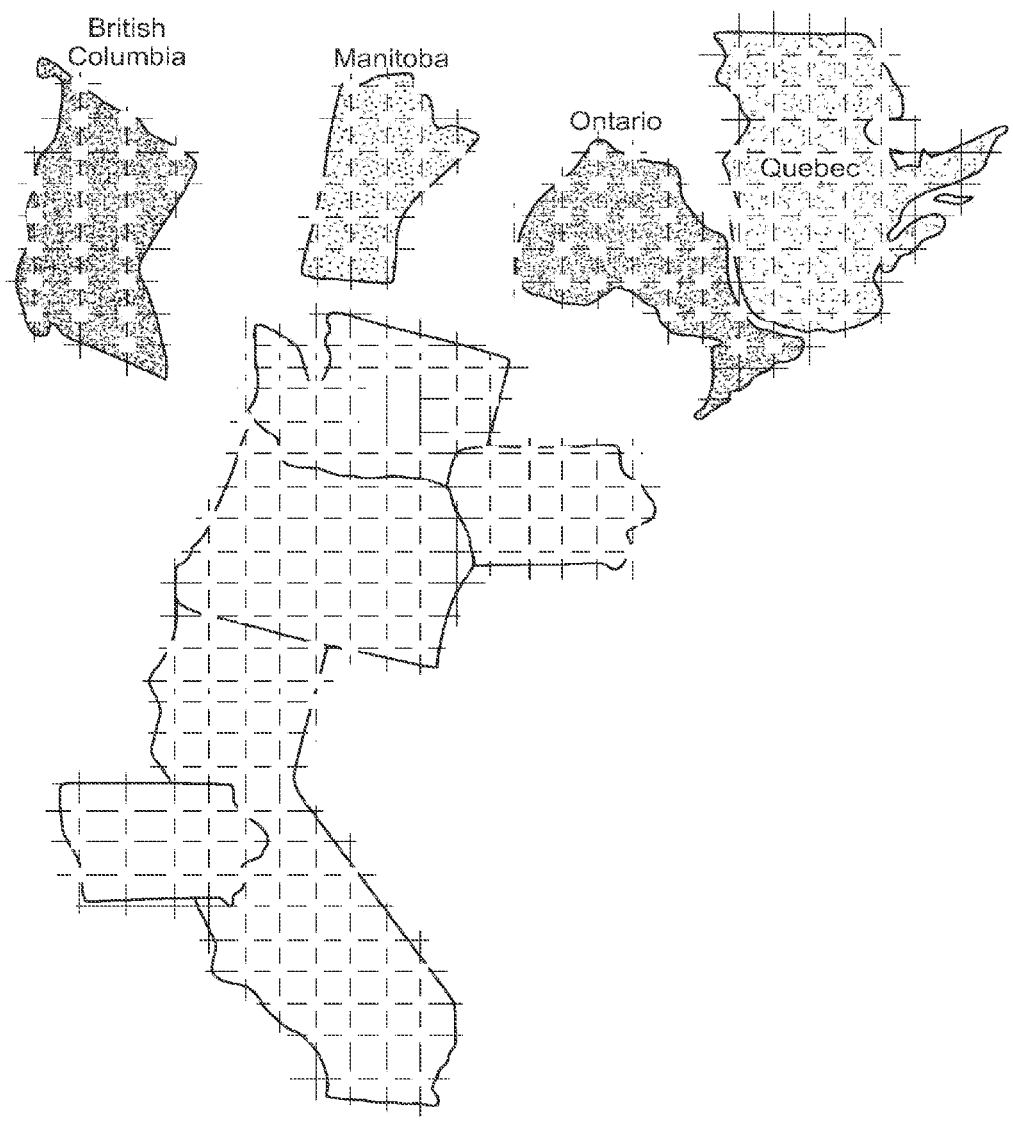
FIG. 28 shows an example of the use of the system of systems to measure, report, verify and provide for carbon exchanges for the Western Climate Initiative including the states of Washington, Oregon, California, Montana, Utah, Arizona, New Mexico, British Columbia (Canada), Manitoba (Canada), Ontario (Canada) and Quebec (Canada). Optional external reference standards may be used as needed.
Figure 29:
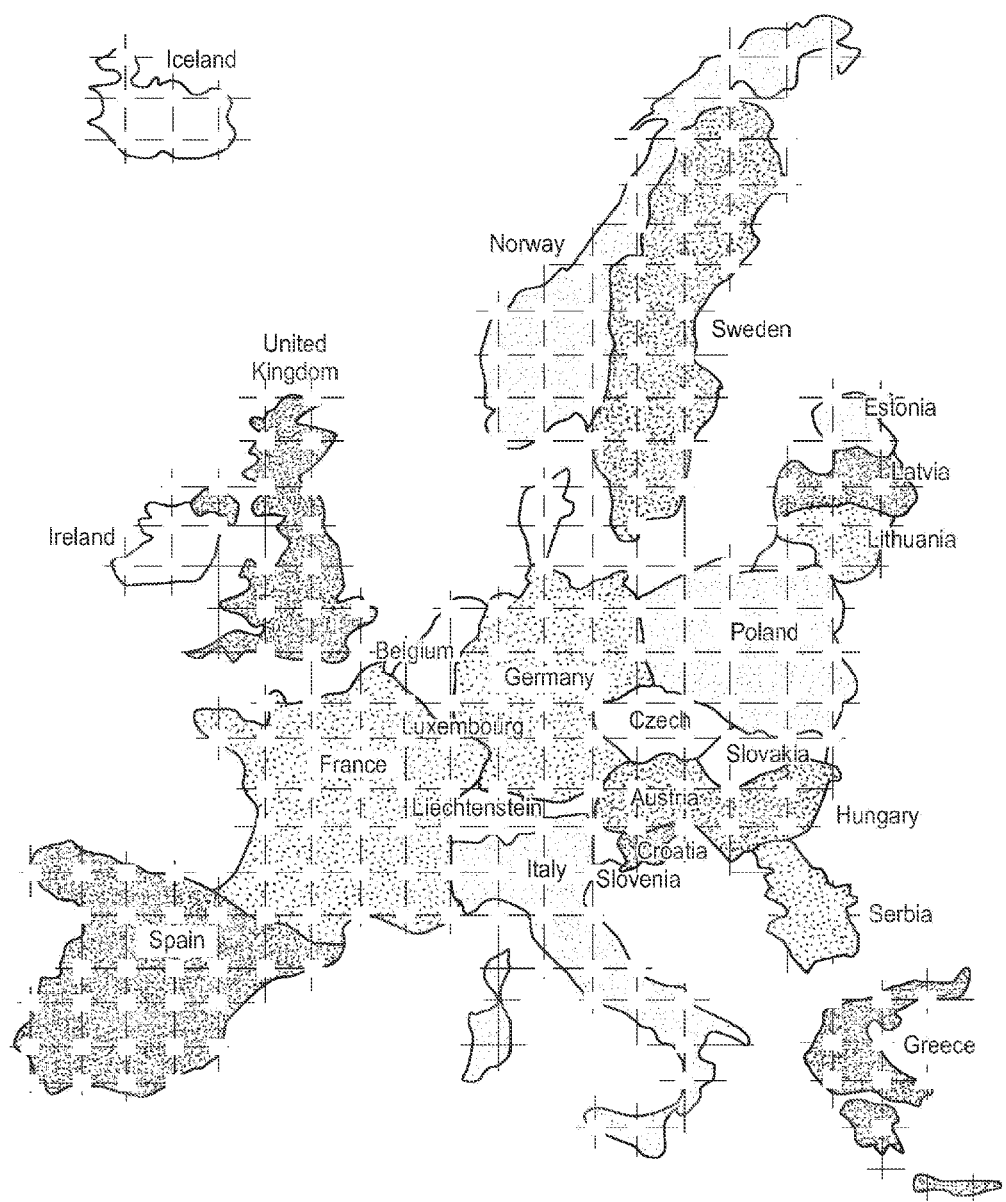
FIG. 29 shows an example of the use of a system of systems to measure, report, verify and provide for carbon exchanges for the European Union Exchange Trading Scheme including the countries of Austria, Belgium, Czech Republic, Estonia, France, Hungary, Germany, Greece, Ireland, Italy, Latvia, Lithuania, Luxemborg, Malta, Netherlands, Poland, Slovakia, Slovenia, Spain, Sweden, UK, Norway, Iceland and Lichenstein. Optional external reference standards may be used as needed.

Accordingly, as shown in FIG. 24, the GMP devices could be placed across country scales utilizing existing towers and other structures to reach above the ground, as in the case of the US and across state wide scales as shown for the state of Maine (FIG. 25). FIG. 26 shows a system of systems placement for the Regional Greenhouse Initiative representing the northeast US. FIG. 27 shows a system of systems placement for the Midwest Greenhouse Gas Accord. FIG. 28 shows a system of systems placement for the Western Climate Initiative. FIG. 29 shows a system of system placement for the European Union Exchange Trading Scheme for greenhouse gases. For the purposes of illustration only the GMP devices are placed roughly at 5 degrees×5 degrees intervals in latitude and longitude or in other configurations as determined necessary according to initial placement of analyzers and other factors. Towers of varying heights may also be used to capture additional data for isotopic flux as a function of height.

Example 2

Soil Carbon Trading

Figure 30:
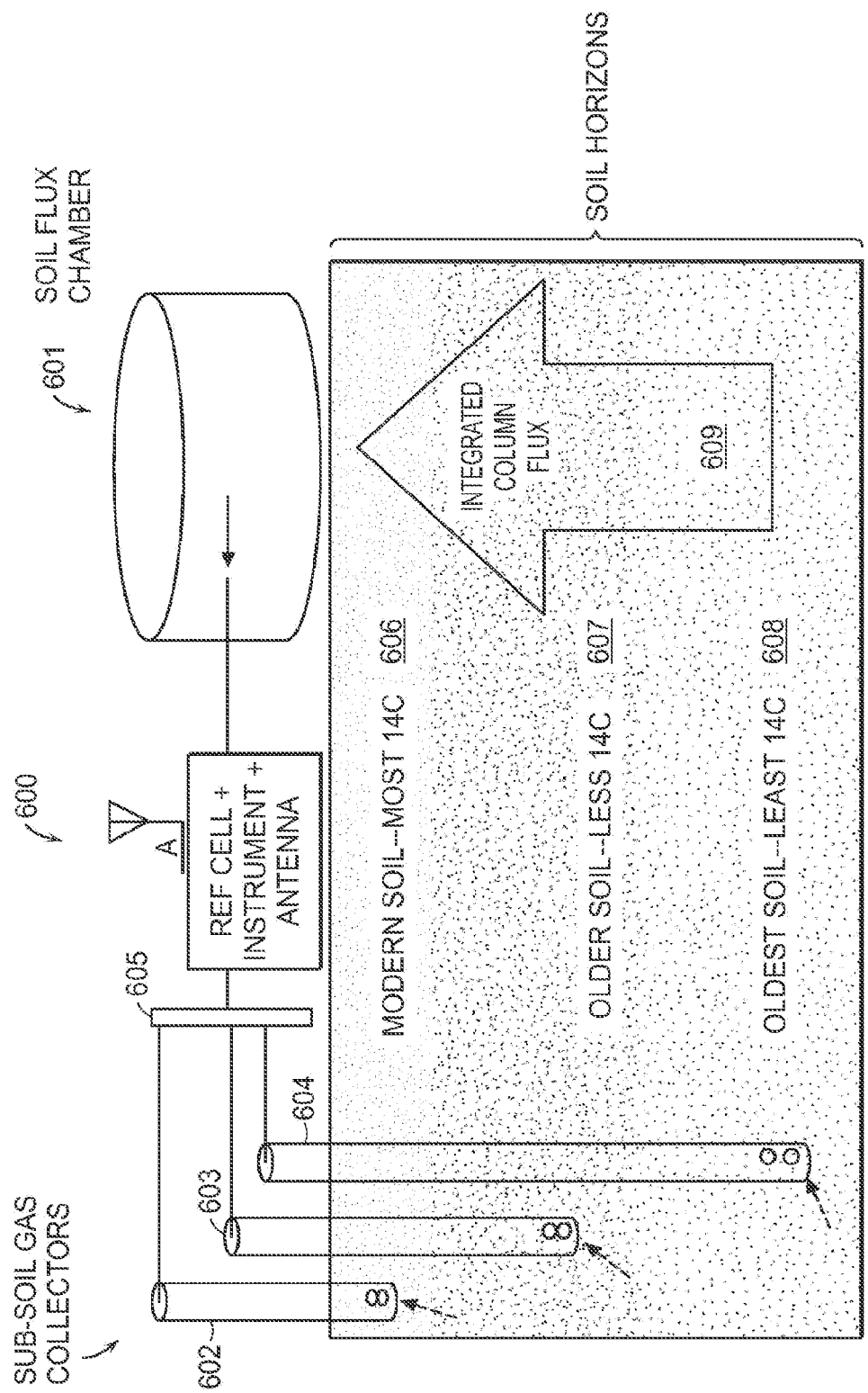
FIG. 30 shows an example of the use of a system of systems to measure, report, verify and provide for carbon exchanges for soil carbon emissions. Optional external reference standards may be used as needed.

Referring to FIG. 30 another embodiment of the system of systems is provided. The soil reservoir of carbon far exceeds that of the standing biomass and in some respects may be more labile than that of the standing biomass. The warming of higher latitudes as predicted by models of the biosphere under increasing $CO_2$ and consequent surface warming suggest that large amounts of previously sequestered carbon may be released. The release of carbon in the soil is primarily determined by soil moisture and temperature (Amundson et al., 2008) and thus is likely to be highly heterogeneous across the landscape depending on a host of factors. For these reasons soil flux should be determined and measured in a wide variety of sites to detect soil release in relation to global warming. Moreover, efforts to sequester carbon in soils ranging from agricultural to prairie lands are eligible for carbon trading offsets (CCX 2010) but are based on gross oversimplifications and estimates. A system of systems as described herein:

1) Provides $^{14}CO_2$ signal for fossil fuel $CO_2$, $^{13}CO_2$ signal for biogenic $CO_2$ and total $^{12}CO_2$ measured at specified time intervals of approximately 1 sample per minute as integrated with soil flux chambers and soil probe gas sources. Eddy covariance towers shall also be used as described above for the forest sampling with a sample frequency of from 1 to 10 Hertz ideally but may be up to 100 Hz. As for the forest carbon GMP—eddy covariance set up, such applies to the soil sample chambers and soil probes.
2) Provides for an inter-calibrated network of analyzers to ensure comparable results for each device. The placement of soil gas chambers and probes can be according to a statistical analysis for the area to ensure representative data. Number, heights and configuration of eddy covariance measurements can depend on factors such as topography, strength of diurnal $CO_2$ fluctuations and wind patterns. However, tower heights may be relaxed in settings where the vegetation cover is close to the surface as in grasslands, prairies, etc. ranging from several meters to 30 meters.

3) Provides for a telemetry system to transmit data to a central location.

4) Provides for data analysis and model integration.

Much as the measurement of total $CO_2$ in the atmosphere does not reveal sources (sinks) of the $CO_2$, the soil $CO_2$ atmosphere also does not reveal source components in relation to total $CO_2$. In the case of the soil, however, the various carbon (referring to FIG. 30) sources of interest relate to the age of the carbon rather than to a distinction between biogenic versus fossil carbon. Specifically, the large scale release of very old soil carbon in the age range from 2 to 8,000 years ago would signify that previously sequestered carbon is subject to release and would potentially portend a large source of carbon to the atmosphere that could have significant consequences for the radiative budget of the atmosphere.

A number of well developed technologies exist to automatically sample above ground soil gas for integrated soil flux. Such a device is manufactured by Li-COR Bioscience Corp., Lincoln, NB, model LI-8100-101 and LI-8100-104, Automated Soil $CO_2$ Flux System. The device named is specifically designed for multiple chamber use, offering high spatial and temporal resolution of soil $CO_2$ flux rates. The system features chambers that automatically open and close at specified intervals to avoid artifacts from $CO_2$ absorption and leakage over long time periods caused by small pressure changes. Such chambers as sold by LI-COR can be operated remotely in windy and/or calm conditions.

In addition to the soil gas monitors, placement of eddy covariance setups is also required to document accumulation of soil gas in the near surface environment. Accordingly, sampling rates for eddy covariance can be rapid at <1 second. Thus, such as system of systems incorporating the LI-COR devices in conjunction with the GMP and located in ensembles and further supported by eddy covariance methods will be highly valuable in determining the release or sequestration of carbon for a given area.

Additionally, commercial devices for sampling the $CO_2$ soil atmosphere at depth are also available such as that described by Vaisala, Inc., Model GMP3431 carbon dioxide probe, operated in flow through mode. In practice, those skilled in the art of sub-soil gas sampling recognize a number of approaches in capturing gas samples at depth for analysis.

Thus, as shown in FIG. 30, a GMP unit 600 coupled to any number of soil sampling chambers at the surface 601 and/or to any number of sub-surface sampling systems 602, 603 and 604 combined in a sample manifold 605 could detect singly and across a landscape the soil carbon release or soil carbon sequestration. The above soil flux chamber 601 provides an integrated soil gas sample resulting from the entire soil column 609 and thus represents an average of soil gas composition. Soil probes at different depths 602, 603 and 604 integrated with a sample manifold 605 provides soil gas composition characteristic of each soil layer. Modern soil 606 will contain higher concentrations of $^{14}C$ than older soils 607 and 608 at greater depths in the soil column. In this particular illustration, soil isotopic carbon flux can be measured directly by combining soil flux rates given as quantity of $CO_2$ fossil and biogenic released from a given area over a defined period of time. Accordingly, use of appropriate models such as described in Amundson et al., 2008 can be used in conjunction with isotopic data to derive metric tons of carbon as released or sequestered. As indicated above, the use of eddy covariance can integrate the accumulation of gas from the soil and gas in the near surface environment to fully define the carbon flux for a given area over a given period of time.

The system of systems approach as described herein can be used to measure and monitor soil $CO_2$ flux in relation to soil conservation strategies such as no till methods and replanting of barren soils (e.g., Schlesinger 2000) and thus provides a critical means of defining the capacity of a given soil for carbon sequestration under a variety of conditions. Such a system of systems is clearly needed for soil carbon measurements. As described previously, the Chicago Climate Exchange provides estimated rates of sequestration for large tracts of land based on models alone (CCX 2010). Such models do not take into consideration factors such as soil moisture, changing surface temperature and application of nutrients as fertilizer and thus creates uncertainties that can lead to erroneous carbon metrics for soil carbon trading. The use of the system of systems as disclosed herein presents a means to reduce such uncertainty and result in verified carbon fluxes that may then be used to enter the soil carbon market. The use of the system of systems as disclosed herein could provide several types of soil carbon financial products such as soil carbon flux as related to specific land management practices (e.g., planting of particular species of plant, tillage method, nutrient application, etc.). As described above for forest carbon trading, the system of systems can be used to quantify carbon dynamics in areas where a variety of soil and vegetation management practices are employed for industry and/or according to soil ecosystem type.

Example 3

Agricultural Emissions Trading

Figure 31:
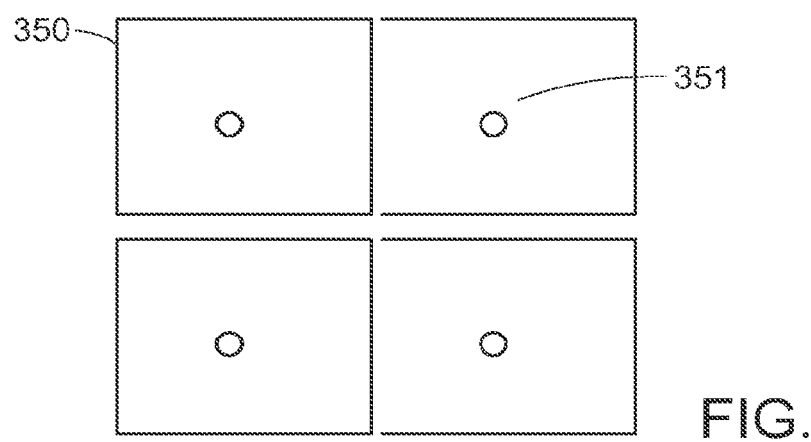
FIG. 31 shows an example of the use of a system of systems to measure, report, verify and provide for carbon exchanges for agricultural activities. Optional external reference standards may be used as needed.

Referring to FIG. 31 another embodiment of the system of systems is provided. According to FIG. 31, agricultural fields 350 are defined in a given location. In the center of any given field or series of fields an eddy correlation flux tower 351 is established that:

1) Provides $^{14}CO_2$ signal for fossil fuel $CO_2$, $^{13}CO_2$ signal for biogenic $CO_2$ and total $^{12}CO_2$ measured at a rapid rate of approximately 1 to 10 Hz ideally but up to 100 Hz allowing integration with eddy covariance methods.

2) Provides for an inter-calibrated network of analyzers to ensure comparable results for each device. Configuration and heights of towers for eddy covariance will provide for extension above the crop surface and thus may range from several meters to 30 meters with the number of GMPs determined by the signal strength, wind patterns and other factors providing detection capability of the isotopic signature for agricultural carbon cycling. Initial placement of the GMPs may be needed for optimal placement of GMP analyzers.

3) Provides for a telemetry system to transmit data to a central location.

4) Provides for data analysis and model integration.

Currently, verification of agricultural carbon exchange and storage is one of the most difficult areas of endeavor. The difficulty is easily grasped when one considers that plants are grown on an annual or semi-annual basis and then removed from the land surface. Thus, a full accounting of carbon budgets for agriculture must take into account biomass removed from the land and replacement of that land with new crop cover. In addition, agricultural practices by their nature involve digging up and in many cases turning over soil allowing volatile soil carbon components to be released to the atmosphere by oxidation. In addition, the use of fertilizers are also considered in the overall budget terms, since fertilizer is applied with a cost to the grower and its production involves generation of greenhouse gases. In this case again, while large areas of agricultural land may be planted with one crop, each such area of different crops is provided with an eddy covariance system of systems. Accordingly, verification measures utilized by the CCX (CCX 2009) for example, lack precision and are applied blindly to all soils despite obvious differences in planting and harvesting specifics and thus are uncertain potentially resulting in carbon trading errors that could be minimized by use of a system of systems approach as disclosed herein.

Another approach involves models that are parameterized with any number of soil data sets representing field sample analyses over large areas. One such product, C-Lock (Updegraff et al., 2005) employs such a system. Carbon sequestration rates are essentially classified into no-till and conventional tillage and applied blindly across large areas of land. The C-Lock approach is based upon a soil organic carbon model known as Century (Parton et al., 1993) and is used without further examination of soil carbon content of the factors that may alter such content including variations in climate factors of rainfall, vegetation change and land management. Thus, as with forest carbon flux and its relation to carbon pricing, the agricultural carbon financial products as described herein are not known or suggested and no system of systems to measure, monitor, verify and account for carbon flux has been implemented.

According to an embodiment of the system of systems herein disclosed, a set of monitoring stations placed within the sample grid of agricultural land can be collected as described earlier. A commercially available system, such as the eddy covariance system available from Campbell Scientific, UK can be deployed and integrated with a GMP $^{13}C$ and $^{14}C$ analyzer at intervals of from 100 meters squared to 1000 meters squared and multiples depending on the size of the agricultural area to be studied. An inventory of $^{13}C$, $^{14}C$ and $CO_2$ concentrations are acquired as described earlier. In this case, biomass harvested quantified by weight and soil organic carbon at intervals to match the GMP device placement can be measured by standard soil analysis techniques; all practices known to those skilled in the art of agricultural and soil management. Thus, application of the system of systems in conjunction with known models of agricultural management can reduce uncertainties for carbon metrics required for carbon trading representing a variety of agricultural practices.

We note here that recommendations and requirements for agriculture emissions reductions provided by the CCX (CCX 2010) focus on destruction of methane produced by manure digesters. In the case of a small single point source, methane destruction is verified by flaming of methane at the vent. However, we note above the larger issues of carbon flux from agricultural areas are treated as estimates and thus prone to error. In the case of ruminant management we note that the addition of nutrients from manure to the landscape is not taken into account even though it is clear that emissions from land managed in relation to ruminant management must also be considered. While the embodiments described herein provide examples for $CO_2$, the system of systems is applicable to any greenhouse gas such as methane and nitrous oxide.

Example 4

Carbon Emissions Trading for Bodies of Water (e.g., Ocean)

Figure 32:
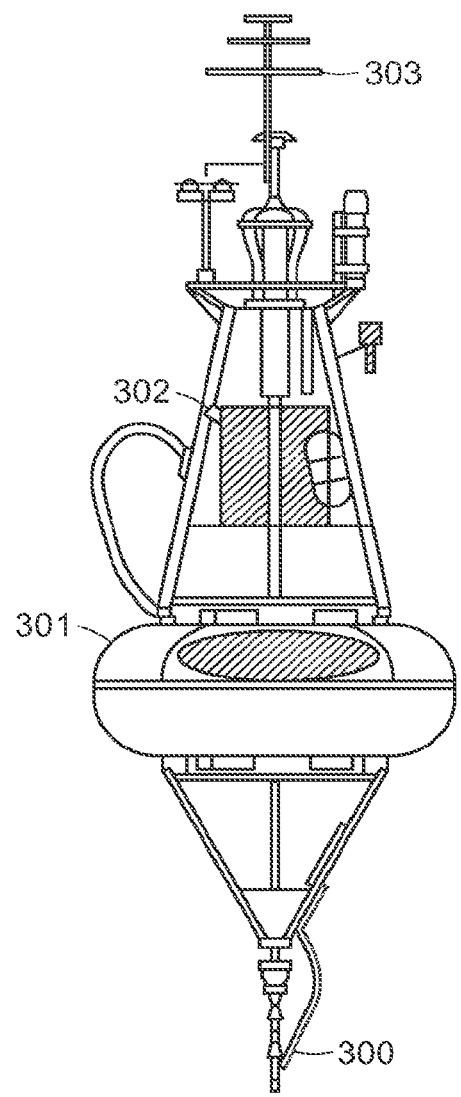
FIG. 32 shows an example of the use of a system of systems to measure, report, verify and provide for carbon exchanges for oceanic exchange. Optional external reference standards may be used as needed.

Referring to FIG. 32, an embodiment suitable for determination of oceanic carbon exchange is described. There is considerable interest in sequestration of carbon by the ocean induced by iron oxides placed in surface waters as a means of "ocean fertilization." Ocean iron fertilization works by improving the efficiency of natural phytoplankton production in the open ocean. Phytoplankton are responsible for approximately half of the world's annual $CO_2$ absorption capability. As they continually bloom, mature and die in a 60-day lifecycle, a portion of their biomass sinks to depth, locking away carbon for long periods of time. This process, called the "biologic pump," is one of the oldest ecological mechanisms on Earth. Over the last several hundred million years it has helped concentrate nearly 90% of all mobile carbon in the deep ocean as sediments and dissolved bicarbonates. However, as a mechanism to sequester carbon directly from the atmosphere the measuring, monitoring, verification and accounting of carbon sequestered from iron fertilization has not been implemented.

In several respects the ocean has been treated like the world's forests according to the Kyoto Protocol in that the worlds oceans are not included as eligible for carbon credits even though the oceans are a major source and sink of $CO_2$. While the dangers of altering large portions of the natural ocean carbon cycle are real and should be considered a geo-engineering effort, a primary impediment to carbon reduction via the ocean is also related to a lack of carbon flux data for the worlds' oceans and the capability to closely measure and monitor changes in the oceans' carbon flux. The GMP system of systems can be deployed in much the way as they are for the forests. Instead of towers to support GMP ensembles, ocean buoys could be used as surface monitors and could be equipped with sampling hardware to sample water at desired depths. As for forests, the $^{13}C$ and $^{14}C$ isotopic composition of carbon in seawater are key diagnostics that indicate the functioning of the oceanic carbon dynamics (e.g., Cias et al., 1995; Broecker 2007). In the case of $^{14}C$ a transient $^{14}C$ signal as a result of the hydrogen bomb use created a pulse of manmade $^{14}C$ which provides a convenient signal to measure rates of carbon flux in the ocean. In the case of $^{13}C$, seawater biology fractionates $^{13}C$ during photosynthesis and respiration in a manner similar to that of terrestrial plants. However, as for the forests the oceans carbon dynamics are not measured with enough frequency or spatial coverage to provide a clear pattern and trend in carbon oceanic flux.

Several companies are seeking to commercialize the process (e.g., www.CLIMOS.com) but have not proposed effective means to measure, monitor, report and verify emissions for carbon trading schemes. However, it is difficult to assess the effectiveness of oceanic carbon exchange and sequestration with ocean chemistry and stripping of dissolved gases from ocean water. Typically, stripping of dissolved gases from ocean water is a near automated process that results in flask samples of gas similar to that obtained for whole air that are then analyzed individually using IRMS techniques. The system of systems described herein is readily applicable that:

1) Provides $^{14}CO_2$ signal for fossil fuel $CO_2$, $^{13}CO_2$ signal for biogenic $CO_2$ and total $^{12}CO_2$ measured at hourly intervals or less with integration of a $CO_2$ extractor from seawater with a GMP and ensembles thereof
2) Provides for an inter-calibrated network of analyzers mounted on ocean buoys to ensure comparable results for each device. Placement on the surface can depend on signal strength and may be determined by initial testing of configurations to accommodate the signal and area of interest.

3) Provides for a telemetry system to transmit data to a central location.
4) Provides for data analysis and model integration.

Thus, a system of systems could be operated remotely on an ensemble of instrument buoys covering specific oceanic areas to measure atmospheric gases in the upper part of the ocean. Gas selective membranes or automated gas stripping devices would be employed to sample dissolved ocean gases as integrated with the GMP. A seawater $CO_2$ extraction device is commercially available from Axys Technologies, Sidney, British Columbia, model Greenhouse Gas Sentinel. Alternatively, the GMP isotopic analyzer could be operated shipboard making essentially continuous measurements for $^{14}C$ and $^{13}CO_2$ (e.g., McNichols et al., 2002). Referring to FIG. 31, seawater via an underwater inlet 300 is drawn into a gas extraction unit 301. The gas is extracted and conditioned as described earlier by scrubbers and dryers and then is pumped into the isotopic analyzer 302. Isotopic data and related sensor data are transmitted via the onboard SCADA system 303. The buoys, gas stripping and related methods are well known to those skilled in the art of oceanic gas sampling. Thus, use of the system of systems will allow continuous, standards based, measuring, monitoring and reporting of carbon exchange in the ocean to quantify oceanic carbon sequestration as a result of atmospheric mitigation strategies or as a result of changing global conditions. The ocean, representing a large potential sink or source of $CO_2$ is a critical area for quantification that could involve carbon trading.

Example 5

City Scale Carbon Emissions Trading

Figure 33:
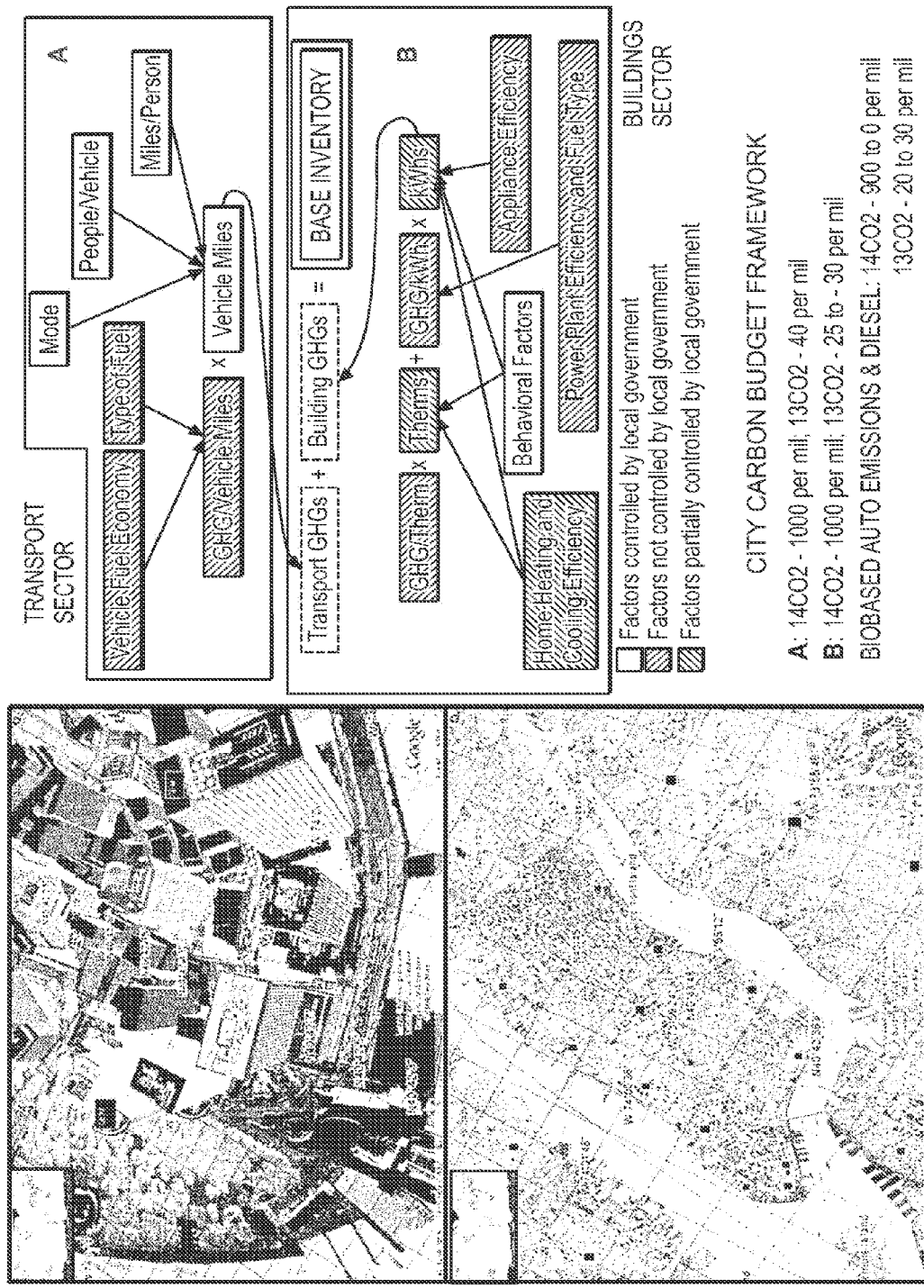
FIG. 33 shows an example of the use of a system of systems to measure, report, verify and provide for carbon exchanges on a city wide scale representing the city of New York, N.Y., USA. Optional external reference standards may be used as needed.

Referring to FIG. 33, an application to a city scale carbon budget for Manhattan, N.Y. is illustrated. Greenhouse gas budgets of large cities in some cases can account for a majority of emissions for a given state or region. Thus, an approach that quantifies the emissions from city scale activity could be highly valuable in an overall carbon budget plan. Major sources of emissions in cities range from industrial (natural gas and fuels) to power generation (coal, fuels) to automobiles (gas, diesel). A city scale system of systems is readily applied to city scale measuring and monitoring that:
1) Provides $^{14}CO_2$ signal for fossil fuel $CO_2$, $^{13}CO_2$ signal for biogenic $CO_2$ and total $^{12}CO_2$ measured at a variety of locations and elevations on an hourly or less sample analysis schedule. Eddy covariance applications with sampling rates of 1 to 10 Hz ideally but may be up to 100 Hz.
2) Provides for an inter-calibrated network of analyzers to ensure comparable results for each device. Device placement may depend upon suitable structures and proximity to borders, water bodies, etc., but not less than 1 GMP per square miles and up to 1 GMP every 10 square miles of city landscape.
3) Provides for a telemetry system to transmit data to a central location.
4) Provides for data analysis and model integration.

Referring again to FIG. 33, multi-isotopic analyzers are placed at approximately 10 to 20 mile intervals along the coast of Manhattan with a additional analyzers as shown to capture emissions from the interior of the city environment. As described in FIG. 2, a multi-isotopic analyzer can differentiate sources of $CO_2$ from fossil and biogenic sources including differentiation of natural gas $CO_2$ from coal and auto fuel $CO_2$. Such measurements can be used to quantify offsets in automobile emissions, industrial emissions and use of solid fuels. For example, California's AB32 reduction plan involves substantial reduction of emissions from heavy duty tractors that pull 53 foot or longer box-type trailers (www.arb.ca.gov). A system of systems provides an integrated measure of such emissions for the city of Manhattan in addition to sourcing of other emissions. Carbon emissions from the individual-level activities of passenger transport and energy use in residential buildings accounted for approximately 40 percent of all US carbon emissions in 2005 (Brown et. al. 2001). Thus, a system of systems as disclosed herein Absent an enormous leap forward in low-carbon energy technology, meeting the challenge presented by climate change will require that individuals, households, and communities all become part of the process, with building codes, transport infrastructure investments, and support for transportation alternatives. Recognizing this, many cities have developed climate action plans, containing a disparate mix of mostly voluntary greenhouse gas emissions reduction proposals. However, as has been proposed by Salon et al. (2008), city carbon budgets are needed to develop a climate policy instrument for local governments.

The standards and methods to quantify emissions from the various city sources will require that both $^{13}C$ and $^{14}C$ be measured and integrated within the budget analysis framework. Such a framework could consist of several budget allocation methods including:
1. Allowance allocation via auction,
2. Uniform allowance allocation on a per capita basis,
3. Using current per capita emissions as a starting point and transitioning gradually to a uniform allowance allocation on a per capita basis, and,
4. Using current per capita emissions as a starting point and reducing allowance allocation by the same percent for all localities.

However, few if any direct measurements have been proposed for management or compliance of the emissions, and thus reductions and other actions based on estimates may be in significant error and be costly. Thus, use of the system of systems would be highly valuable to establish budgets and verify estimated emissions data for city scale environments.

The system of systems would be placed strategically throughout a city scale landscape. Data collection for $^{12}C$, $^{13}C$, $^{14}C$ and other species such as carbon monoxide (CO) would be collected and transmitted as described earlier. Transmitted data would then be used in already developed models that incorporate real time meteorological data for winds, etc. In select locations an eddy covariance tower, also commercially available, could be used to augment data and establish flux patterns for specific areas of the city. This concept is also illustrated in FIG. 32 for the City of NY in one embodiment. The lower left panel shows GMP site locations along both shores of Manhattan with a central mid Manhattan site. Other GMP locations are shown to the east and west of Manhattan for illustration purposes. The GMP apparatus can be located on top of buildings and above the ground layer ensuring well mixed air.

One skilled in the art of gas emissions from city sources can readily see that automotive carbon emissions will have a $^{13}C$ and $^{14}C$ isotopic profile that is distinct and detectable from emissions based on natural gas and coal. All of the fossil fuel sources will have essentially no $^{14}C$ rendering a value of −1000 per mil $^{14}CO_2$. However, there is sufficient range in isotopic composition in $^{13}CO_2$ ratios to separate gas fuel (auto fuels) from coal and natural gas as illustrated in FIG. 2. In addition, as a measure of the use of bio-based fuels mixing lines from −1000 to modern $^{14}C$ could be used (see FIG. 2). Thus, the GMP and system of systems would be important in detailing carbon budgets. The isotopic data would be used to construct detailed city wide zones of emission levels when coupled with meteorological models, and such data could be used in cases where reductions can be verified to enter trading markets where such credits (reduction credits) can be registered and traded accordingly (e.g., Regional Greenhouse Gas Initiative, RGGI, 2009).

Example 6

Carbon Sequestration Emissions Trading

Figure 34:
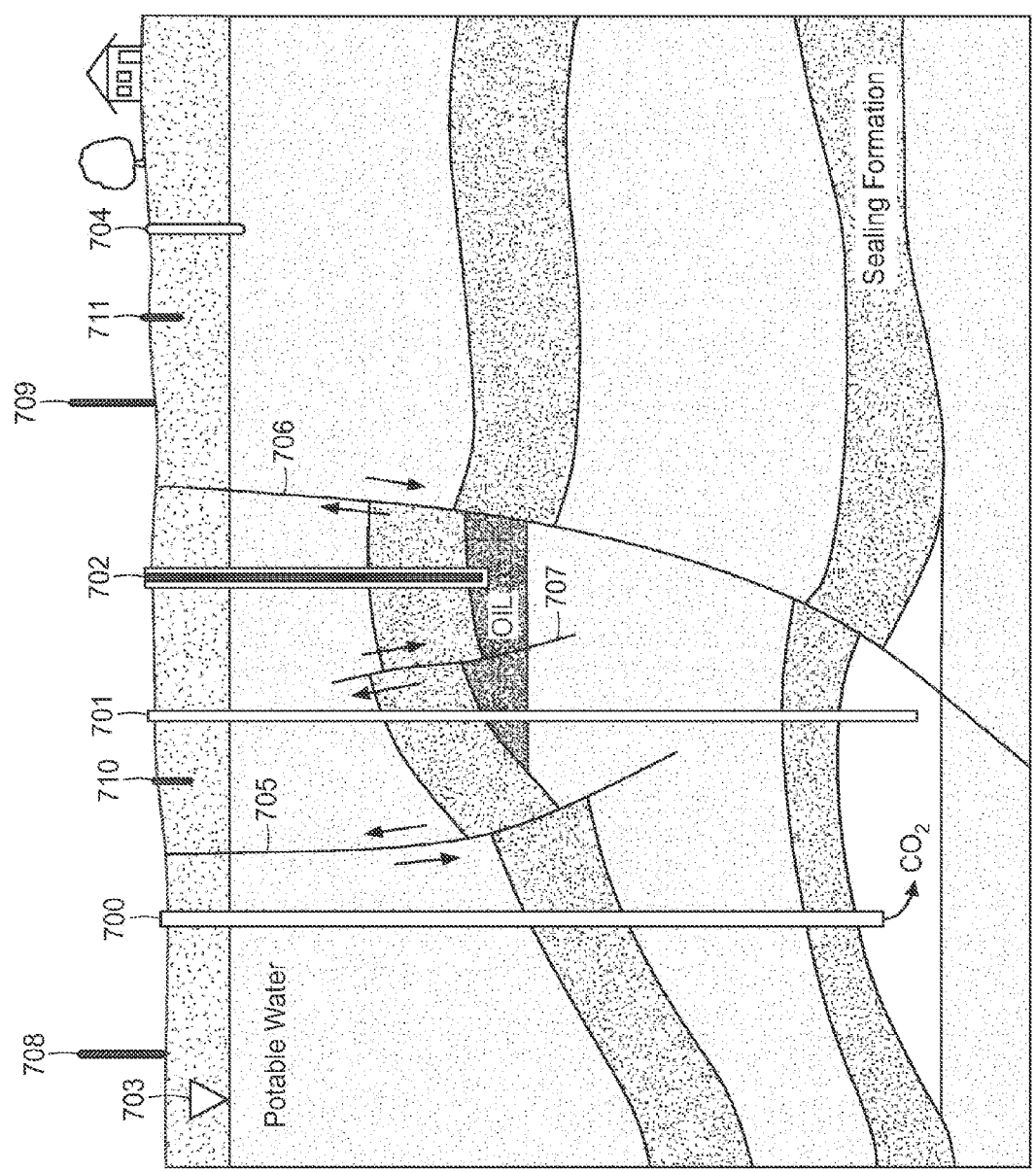
FIG. 34 shows an example of the use of a system of systems to measure, report, verify and provide for carbon exchanges for $CO_2$ sequestration projects. Optional external reference standards may be used as needed.

Referring to FIG. 34 an example application to carbon sequestration of power plant carbon emissions is described. Measuring, monitoring, verification and accounting (MVA) has been identified as one of the most important ways to ensure that carbon capture and storage (CCS) projects are safe and reliable. Leakage associated with injection wells, inappropriately sealed abandoned wells, or unidentified/poorly characterized faults and fractures may result in point, line, or area $CO_2$ sources of varying intensity. Reliable measuring and monitoring systems, with the required sensitivity and resolution, must therefore be available for a range of leakage scenarios. Detection and characterization of potential $CO_2$ leakage from CCS sites may be challenging in the near-surface environment due to the large spatial and temporal variation in background $CO_2$ fluxes (e.g., Oldenburg et al., 2003; Lewicki et al., 2005; 2009; Leuning et al., 2008). Also, the area of a given surface $CO_2$ leakage signal could be several orders of magnitude less than the total area (e.g., ~100 km$^2$) of the $CO_2$ reservoir above which monitoring will be carried out. Consequently, innovative and advanced monitoring technologies are required with the capability to detect, locate, and quantify $CO_2$ leakage signals with potentially small magnitude and area, relative to background $CO_2$ variations and the total area of investigation, respectively.

As shown in FIG. 2, it is clear that $^{13}C$ ratios cannot distinguish between biogenic and fossil fuel sources. Nor can total $CO_2$ concentration data be used to unequivocally identify leakage of fossil fuel derived $CO_2$ from a carbon capture and storage site. A distinct signal for fossil fuel can be unequivocally be found in $^{14}C$ ratios alone. However, as can be appreciated in the assessment of leakage from a large scale carbon sequestration project, leakage of stored fossil fuel derived $CO_2$ in most cases will blend with biogenic $CO_2$ as it diffuses through local soils, plants and water bodies. Referring to FIG. 34 again, the primary goal of carbon sequestration and capture is to essentially bury $CO_2$ in gaseous form as it exits from power plants or is transported via pipeline from a central storage facility. Burial can take place in a wide variety of geological formations on land and under the sea. However, a central feature of the approach is negligible leakage after burial and capping of the burial location. In most cases the potentially affected area is many square miles and thus the system of systems approach is well suited for this distributed application that:

1) Provides $^{14}CO_2$ signal for fossil fuel $CO_2$, $^{13}CO_2$ signal for biogenic $CO_2$ and total $^{12}CO_2$ measured for eddy covariance (sampling rate 1 to 10 Hz ideally, up to 100 Hz), selected gas streams, soil gas at the surface and at depth and extracted $CO_2$ from groundwater.

2) Provides for an inter-calibrated network of analyzers to ensure comparable results for each device. Placement may be dependent on geological footprint of the injection site and could range from 1 GMP every square mile to one unit for every 10 to 20 square miles. Locations of analyzers can be placed in proximity to areas particularly labile to leakage (e.g., well heads, faults).

3) Provides for a telemetry system to transmit data to a central location.

4) Provides for data analysis and model integration.

The GMP analyzers will receive gas from selected areas by sample lines from specific sources including well heads 700, 701, 702, soil surface flux chambers 710 and 711, buried soil gas collection probes at several depths 710, 711, $CO_2$ extracted from ground water 703, 704, local bodies of water, down hole monitoring sites, and eddy flux towers in forested areas 708, 709. According to FIG. 2 the system of systems employing the multi-isotopic analyzer can distinguish pure fossil derived $CO_2$ gas with $^{14}C$ ratios from −1000 per mil and pre biogenic derived $CO_2$ with $^{14}C$ ratios of modern (approx. 1 to 50 per mil), as well as blends along the mixing line for both end members. The range for $^{13}CO_2$ is approximately −10 per mil for pure grassland emissions (C4 grasses) to approximately −30 per mil representing typical C3 based $CO_2$ derived from biomass. Referring to FIG. 34, CO2 leakage can occur along faults 705, 706, 707 and thus a variety of detection methods as described above is required to detect leakage even at very low rates. For example, a leakage rate of 1.0%, 0.1% and 0.01% from a total sequestration of 100,000 tons $CO_2$ will result in loss of 1000, 100 and 10 tons per year respectively. As described previously, sample concentration of $^{14}CO_2$ even at very low levels (e.g., sub ppm) can be accomplished utilizing the cryogenic trap process and thus provide effective leakage rate determination at very low levels.

Thus, a combination of approaches described in previous examples (soil, forest, oceanic, agriculture) can be used in combination to unequivocally identify leakage of $CO_2$ derived from fossil fuel and subsequently buried. Placement of gas sampling locations may include, without limitation, pipe structure gas flow at well head, down hole or in surface structures, land surface locations including soil surface flux, eddy correlation towers and at depth soil sampling of the gas soil profile.

Example 7

Flue Gas Carbon Emissions Trading

Figure 35:
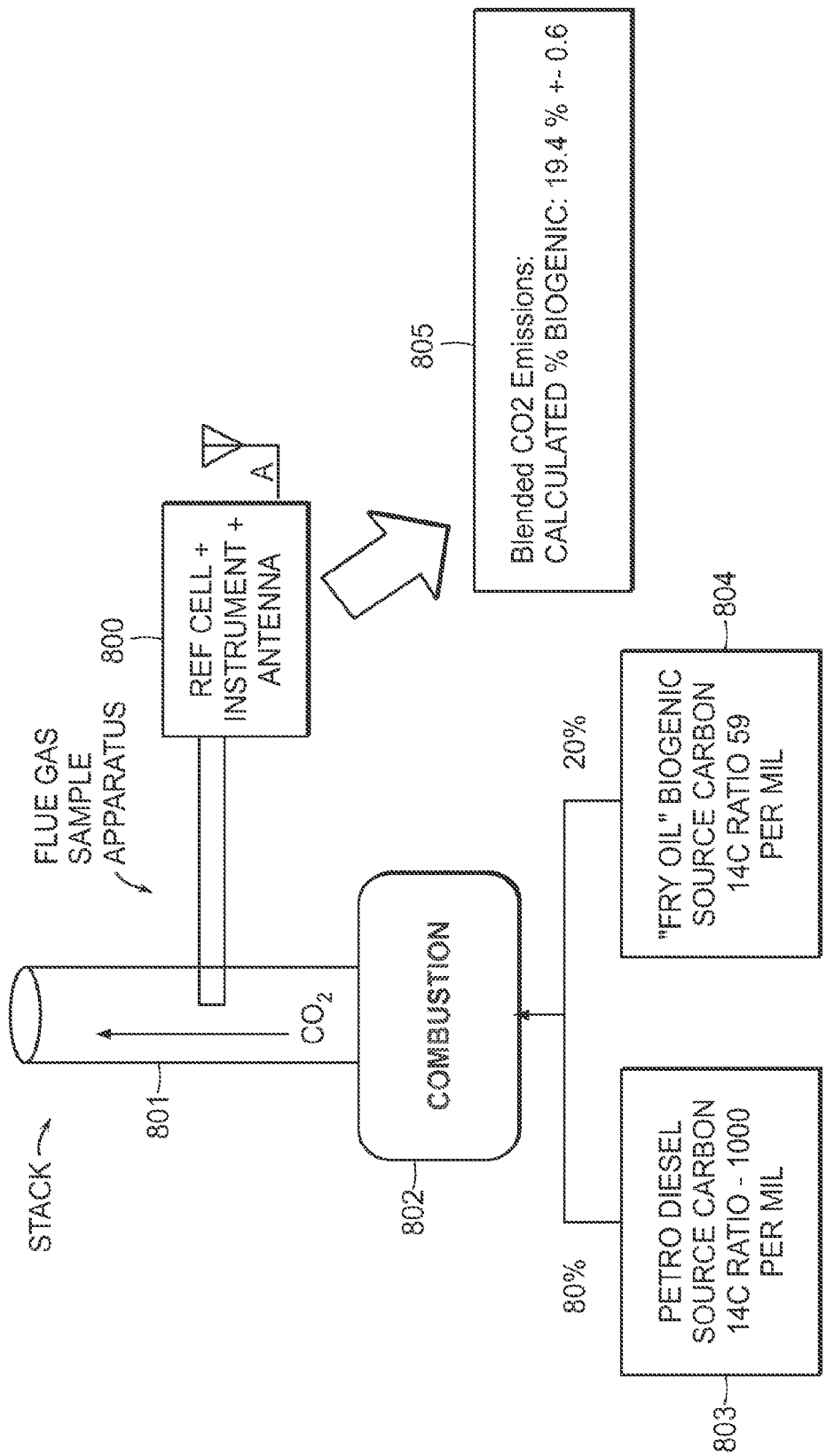
FIG. 35 shows an example of the use of a system of systems to measure, report, verify and provide for carbon exchanges for flue gas. Optional external reference standards may be used as needed.

Referring to FIG. 35 an example of measuring and monitoring to establish relative proportions of biogenic and fossil fuel derived $CO_2$ from power plant and other industrial activities is described. Power plant emissions are among the key sources that are currently identified in existing trading schemes as specified by the Kyoto Protocol and placed into practice in the EU ETS and other trading groups. However, actual emissions data are not the primary source of information on such sources, but rather, estimations are used based on the type of fuel burned, combustion efficiencies and other factors pertaining to fuel burn efficiency, rates of fuel consumption, etc. Thus, for the most visible and directly quantifiable point sources of $CO_2$ emissions under regulatory and voluntary programs, actual measurements are not routinely used to verify budgets and emissions reporting.

In addition, it is increasing clear that the combustion of biogenic materials including all types of biofuels creates a key approach to reduce emissions liability since all biofuel usage is credited as "climate-neutral" and therefore not subject to $CO_2$ emissions regulations or carbon trading caps. Thus, a reliable and continuous flow method to differentiate between fossil and biogenic carbon dioxide emissions would be highly valuable to those utilizing biogenic source materials in power plants and other industrial activities. Currently, either source material as solid or liquid is subjected to manual $^{14}C$ analysis using typical scintillation counting or Accelerator Mass Spectrometry (AMD) according to the standard method of ASTM D6866 (Staber et al. 2008; Reddy et al., 2008). The rationale applicable to this approach is well understood and is based on the mixing of end members from pure fossil derived $CO_2$ and pure biogenic derived $CO_2$ as illustrated graphically in FIG. 2.

A determination that verifies the blend of biogenic and fossil derived source in combustion relies on a direct measurement on the % renewable content vs. % fossil content of, for example, gasoline blends regardless of chemical composition. In doing so, it identifies fuel blends containing renewable ethanol vs. synthetic ethanol derived from coal or natural gas. Thus, a system of systems that samples either flue gas or directly combusts liquid fuel blends and subsequently analyzes the resulting $CO_2$ is valuable. Since renewable ethanol is synthesized from modern day plants and the gasoline itself is synthesized from fossil petroleum, a measure on the blend will directly quantify the amount of renewable ethanol in that blend. For example, a blend containing 10% renewable ethanol will give a result of 10% renewable content, whereas a blend containing 10% synthetic ethanol will give a result of 0% renewable content, even though in both cases 10% ethanol is present in the gasoline blend. This characterization supports the underlying intent behind bio-ethanol use. It also adds protection to domestic stakeholders in the absence of truly verifiable origin of ethanol. The approach employed with the system of systems may also be used for verification of bio-diesel and bio-diesel derived products such as lubricants. As with stationary source combustion, any industrial process that generates $CO_2$ during a combustion process can employ the system of systems to estimate the carbon-neutral fraction of the total $CO_2$ emitted.

Some industrial processes that liberate $CO_2$ include, but are not limited to aluminum production, ammonia production, cement production, clinker production (including $CO_2$ emitted from the production of lime), metal production, hydrogen production, methanol production, iron and steel production, and soda ash production.

Other industrial processes combust waste to generate electricity, liberating $CO_2$ as a resultant byproduct. A GMP quantifies the carbon-neutral $CO_2$ within the facility emissions. Combustion of waste material and wastewater sludge are examples of combusted waste.

Examples of Industries that combust waste to produce electricity are the paper/pulp and medical waste disposal sectors. Crop residue burning is another agricultural application that can use the GMP for monitoring purposes. For example, burning of crop residues in the production of ethanol can be measured and monitored with the GMP, providing new source of carbon credits. As with stationary source combustion, the carbon-neutral $CO_2$ liberated in the combustion process can be determined.

The application of a GMP to derive a "Biomass $CO_2$ content" for carbon dioxide effluents is built on some similar concepts to those used by the US Department of Agriculture to derive the biobased content of manufactured products containing biomass carbon. It is done by comparing a relative amount of radiocarbon ($^{14}C$) in an unknown sample to that of a modern reference standard. The ratio in contemporary biomass will be 100% and the ratio in fossil materials will be zero. Carbon dioxide derived from combustion of a mixture of present day biomass and fossil carbon will yield a GMP result that directly correlates to the amount of biomass carbon combusted and carbon-neutral $CO_2$ generated.

The GMP can be calibrated against the modern reference standard provided by the National Institute of Standards and Technology (NIST) with a defined radiocarbon content of 100% contemporary carbon for the year AD 1950. AD 1950 was chosen since it represented a time prior to thermonuclear weapons testing which introduced large amounts of excess radiocarbon into the atmosphere with each explosion (termed "bomb carbon"). This was a logical point in time to use as a reference since this excess bomb carbon would change with increased or decreased weapons testing. In certain embodiments, fixed correction for this effect would be applied per the GMP applications, applying specifically to carbon removed from the atmospheric $CO_2$ reservoir since about 1996.

GMP results relate directly to the percentage carbon-neutral $CO_2$ in an incineration effluent. A value of 71% renewable content measured on $CO_2$ effluent would indicate that 71% of the exhausted $CO_2$ was from biomass (29% from fossil fuel). It does not represent the weight of biomass combusted or the weight of fossil fuel combusted. This is advantageous since the weight of the fuels only indirectly relate to the up-take of carbon dioxide from the atmosphere. The respiration uptake compound was carbon dioxide and the combustion effluent was carbon dioxide. The GMP result will directly and specifically relate to the amount of biogenic/carbon-neutral $CO_2$ consumed and expelled.

Here we illustrate a specific example of the application referring to FIG. 35. A volume/volume blend percentage of biodiesel in a realistic fuel mixture can be estimated based on its $^{14}C$ content, as follows. First, the carbon of the fuel blend with respect to the modern (biological) component and fossil (petrodiesel) component are used to write a $\Delta^{14}C$ mass balance:

$$\Delta^{14}C_{mixture} = FC_{,bio}\Delta^{14}C_{bio} + (1-FC_{,bio})\Delta^{14}C_{petro} \quad \text{(eq 1)}$$

where $\Delta^{14}C_{mixture}$ is the measured $^{14}C$ content of the biodiesel blend via traditional or AMS radiocarbon determination. The $\Delta^{14}C_{bio}$ can be taken as an average measured value of several typical retail fat and oil sources used in biodiesel preparations—in this case we take a value of 62±7‰ consistent with reported values for modern corn in North America (the primary feedstock for cattle) showing an average range of 55 to 66‰, collected in 2004 (Huseh et al., 2007).

The $\Delta^{14}C_{petro}$ was fixed at a value −1000‰, consistent with measurements of petroleum end members as well known to those skilled in the art of radiocarbon determinations of fossil fuel components and as reported in FIG. 2. Additionally, $FC_{,bio}$ is the mass fraction of the total mixture carbon that is derived from biological components.

Thus, rearranging (eq 1), $FC_{,bio}$ can be expressed as:

$$FC_{,bio} = \Delta^{14}C_{mixture} - \Delta^{14}C_{petro}/\Delta^{14}C_{bio} - \Delta^{14}C_{petro} \quad \text{(eq 2)}$$

Equation 2 shows that the proportion of biological carbon in the sample fuel blend ($FC_{,bio}$) can be easily determined based on the measured $\Delta^{14}C_{mixture}$ of the sample and the a priori known $\Delta^{14}C_{bio}$ and $\Delta^{14}C_{petro}$ values of the end member materials. We assumed that $\Delta^{14}C_{petro}$ (−1000‰) and $\Delta^1C_{bio}$ (62+−7‰) represent reasonably constant end members, such that variation in $FC_{,bio}$ is fully explained by the measured $\Delta^{14}C_{mixture}$ value.

In practice, however, a slight complication may arise in that taking a specific example of B100 biodiesel production the United States and Europe, the transesterification step from fats to fatty acid methyl esters (FAMEs—the common mixture for biodiesel) utilizes fossil methanol. For example, for a C18 FAME, 18/19 of the carbon (fatty chain) is from fats and oils and the other 1/19 (methyl carbon) is petroleum-derived. Thus, in order to relate FC,bio more precisely to the B100 end member one can define the following equation:

$$FC_{,B100} = FC_{,bio}/RC_{,bio/B100} \qquad (eq\ 3)$$

where $FC_{,B100}$ is the mass fraction of B100 carbon in the biodiesel blend, and $RC_{,bio/B100}$ is the ratio of biological carbon to total carbon in the pure component B100. Thus, the blend percentage (v/v) of B100 (B*) in a fuel blend may be calculated as follows:

$$B^* = 100[V_{B100}/V_{B100} + V_{petro}] \qquad (eq\ 4)$$

where $V_{B100}$ and $V_{petro}$ are the extensive volumes of the biological and petroleum-based components, respectively, in a control volume of fuel blend. The individual component volumes can then be expressed as:

$$Vx = [mC,x + mH,x + mO,x/Fx] \qquad (eq\ 5a)$$

which equates to:

$$mC,x/Fx[1 + mH,x/mC,x + mO,x/mC,x) \qquad (5b)$$

where mC,x, mH,x, and mO,x are the total masses of carbon, hydrogen, and oxygen, respectively, for component x in the blend control volume, and Fx is the density of component x.

For notation simplicity, one can write:

$$\theta C_{,B100} = (1 + mH_{,B100}/mC_{,B100} + mO_{,B100}/mC_{,B100}) \qquad (eq\ 6)$$

and, $$\theta C_{,petro} = (1 + mH_{,petro}/mC_{,petro}) \qquad (eq\ 7)$$

where $\theta C_{,B100}$ and $\theta C_{,petro}$ characterize the mass abundances of hydrogen and oxygen relative to carbon in the biological and petroleum-based components, respectively. Combining eqs 4-7 and rearranging, the calculated v/v blend percentage of a biodiesel, B*, can be rewritten as:

$$B^* = 100/[1 + (F_{B100}/F_{petro})(\theta C_{,petro}/\theta C_{,B100})(mC_{,petro}/mC_{,B100}) \qquad (eq\ 8)$$

Now recognizing that $$mC_{,petro}/mC_{,B100} = (RC_{,bio/B100}/FC_{,bio} - 1),$$

(eq 8) can be expressed as $$B^* = 100/[1 + (F_{B100}/F_{petro})(\theta C_{,petro}/\theta C_{,B100})(RC_{,bio/B100}/FC_{,bio} - 1)] \qquad (eq\ 9)$$

where $F_{B100}$, $F_{petro}$, $\theta C_{,B100}$, $\theta C_{,petro}$, and $RC_{,bio/B100}$ are properties of the two pure component liquids (B100 and petrodiesel), and thus $FC_{,bio}$ controls the calculated blend content, B*. One can parameterize $F_{B100}$, $F_{petro}$, $\theta C_{,B100}$, $\theta C_{,petro}$, and $RC_{,bio/B100}$ using the averaged values calculated from a data compilation of retail B100 and petrodiesel products, based on literature surveys (e.g., Reddy et al., 2008). Hence (eq 9) does not require calibration to a designated normative fuel blend; rather, it can be parameterized with pure-component properties that are relatively stable for a wide range of source materials. Thus, (eq 9) can accurately estimate the biodiesel content of any realistic fuel blend based simply on the measured $FC_{,bio}$ value (eq 2).

A further simplification can be made by parameterizing (eq 9) using simple averages of $F_{B100}$, $F_{petro}$, $\theta C_{B100}$, $\theta C_{,petro}$, and $RC_{,bio/B100}$ property values from a broad range of retail petrodiesels and B100's published in the open literature (Reddy et al., 2008). Employing such input parameters, (eq 9) is further simplified to:

$$B^* = 100/[(0.869/FC_{,bio}) + 0.0813] \qquad (eq\ 10)$$

where the lumped parameters, 0.869 and 0.0813, are dimensionless. For clarity, the notation "B*" is used to indicate calculated blend content.

Thus, in the example illustrated in FIG. 35, a GMP 800 is installed to receive stack flue gas resulting from a mixture of petro diesel and biogenic carbon via a combustion chamber 802 with a petro diesel component of $^{14}C$ of −1000 ‰ 803 and a biogenic component consisting of typical restaurant French fry fat of +59‰ 804 the blend 805, or B* can be computed to equal according to the equations above to 19.4%±0.6% (Reddy et al., 2008). The data so obtained combined with volumetric flow measurements also made at the stack will result in the total amount of fossil and biogenic carbon released to the atmosphere. For the sake of illustration, we assume that 80 metric tons of fossil and 20 metric tons of biogenic carbon dioxide were released. Thus, the designation of the emissions so calculated over time for one plant or over a defined spatial scale would be rendered as:

+$^{14}C$ units: 80 metric tons.

+$^{13}C$ units: 20 metric tons.

Any group of power plants by region or by company may be so combined in a GMP network to provide a continuous and accurate record of non-fossil source carbon to the combustion process. The GMP in this usage will be a deterrent to fraud as power production sites that mix fuels of biogenic and fossil could report data with a bias towards the non-fossil.

Pricing may be applied accordingly in relation to market exchange conditions and other factors.

Thus, the system of systems apparatus as described above in conjunction with well known methods practiced in the literature can be used to effectively measure, monitor, report, aggregate and monetize based on isotopic constraints units of carbon to be used in market based systems for greenhouse exchanges, regulatory or compliance frameworks or for voluntary emissions reductions, budgets, and policy makers.

Example 8

A Global Radiocarbon Budget and the Nuclear Fuel Cycle

A consequence of the widespread deployment of GMPs offering high data rate and high precision for $^{14}CO_2$ is a refinement of the global radiocarbon budget itself. Such a budget has applications in the monitoring of nuclear power production offering the potential of generating a global nuclear fuel cycle and the detection of rogue nuclear power plants. This follows from the well know reactions that take place during operation of nuclear power plants and fuel reprocessing (Yim and Caron 2006) that releases the radionuclides of tritium and $^{14}CO_2$. While the pulse of $^{14}C$ after the bomb pulse is well known (e.g., Broecker 200) the background $^{14}C$ is now near natural levels (Broecker 2007) and the production of $^{14}C$ due to nuclear reactors is estimated to be about 0.3% of natural levels (Park et al., 2008). Thus, the addition of $^{14}C$ from nuclear reactors in the areas in which such reactors operate can be used to characterize processing activities of such plants. Carbon-14 is present in virtually all parts of the nuclear reactor primary system and has a high production rate. It is released to the environment through gaseous and liquid discharges and though the disposal of solid radioactive waste. Any nuclear power activity will emit $^{14}CO_2$ as it is difficult to directly contain (e.g., Yim and Caron 2006). In areas where no such nuclear power plants exist the detection of $^{14}C$ above background levels should be possible within the 2 per mil range of the current detection capability of the GMP and with an ensemble of GMPs covering the area. $^{14}C$ values of plant material up to 123 per mil have been reported by Roussel-Debet et al. (2006) in the vicinity of a nuclear power plant over a period of 10 years suggesting feasible detection of $^{14}CO_2$ during periods of reactor activity. Under ideal conditions a nuclear power plant operating without authority should be readily identified. The stripping of $CO_2$ from groundwater and subsequent analysis for $^{14}CO_2$ by the GMP also allows the specific route of detection by ebullition of gaseous emissions from underwater sources or from discharge streams from such facilities.

While a number of radionuclides and analyses are conducted for surveillance of nuclear power activity and for verification of treaty provisions (e.g., Gitzinger et al., 2007), they require close proximity to the source of approximately 25 meters, depending on number of detectors and/or area of detector, for both gamma ray and neutron emitting materials (Kallman 2008). The production and emission of $^{14}CO_2$ released from nuclear power production is not well known but has been estimated for the worlds reactors (e.g., Davis 1977; Yim and Caron 2006). A number of studies have sampled for $^{14}C$ in plant sample from areas surrounding nuclear reactors (e.g., Korashi et al., 2006; Dias, C. M., et al., 2008) and have provided background levels due to release of $^{14}CO_2$ from a variety of reactor types including boiling water reactors and pressurized water reactors (Yim and Caron 2006). However, actual measurements of $^{14}CO_2$ as gaseous $CO_2$ are lacking. Thus, a system of system as disclosed herein constitutes a feasible approach to measuring and monitoring one of the major emissions from nuclear power plants, $^{14}CO_2$, that will increase as the use of nuclear power is more widely adopted.

A system of systems will:
1) Provide $^{14}CO_2$ signal for fossil fuel $CO_2$, $^{13}CO_2$ signal for biogenic $CO_2$ and total $^{12}CO_2$ measured for eddy covariance (sampling rate 1 to 10 Hz ideally, but up to 100 Hz), selected gas streams, soil gas at the surface and at depth and extracted $CO_2$ from groundwater.
2) Provide for an inter-calibrated network of analyzers to ensure comparable results for each device. GMP density and arrangement will depend upon local conditions but be such that the source signal for eddy covariance is detected within the range of +2 to +200 per mil, taking background 14C as approximately 5 to 10 per mil.
3) Provide for a telemetry system to transmit data to a central location.
4) Provide for data analysis and model integration.

The use of a system of systems to quantify $^{14}CO_2$ could be applied to measuring, monitoring, verification and accounting for nuclear power facilities in much the same manner as the system of systems would be used for carbon capture and storage. A variety of eddy covariance, groundwater $CO_2$ sampling, point locations (e.g., different parts of the reactor infrastructure) and soil $CO_2$ sampling sites could be situated near nuclear installations. The specific arrangement and configuration of the GMPs would depend on the source strength of the power plant signal, proximity allowed to a given facility and other factors. The need for a system of systems is recognized by the approach taken in sampling large areas of a given region versus traditional radionuclide analyses that depend on direct access to plant sample locations. The system of systems may be a relatively inexpensive route compared to anti-neutrino detection that while offering potentially far-field monitoring is estimated to cost several trillion dollars (e.g., Guillian 2006).

The following references are cited herein and incorporated by reference herein in their entireties US 2008/0015976 Jan. 17, 2008
U.S. Pat. No. 6,164,129 Dec. 26, 2000
US 2007/0250329 Oct. 25, 2007
US 2007/0224085 Sep. 27, 2007
US 2008/0228632 Sep. 18, 2008
US 2008/0228665 Sep. 18, 2008
US 2008/0228630 Sep. 18, 2008
US 2008/0228628 Sep. 18, 2008
US 2008/0221750, Sep. 11, 2008
US 2008/0015975 Jan. 17, 2008
US 2008/0015976 Jan. 17, 2008
US 2008/0059206 Mar. 6, 2008
U.S. Pat. No. 7,154,595 Dec. 26, 2006
U.S. Pat. No. 5,394,236
U.S. Pat. No. 5,783,445
U.S. Pat. No. 5,818,580
U.S. Pat. No. 5,864,398
WO 99/42814
U.S. Pat. No. 7,616,305
Air Resources Board, State of California. ARB 2009 http://www.arb.ca.gov/cc/factsheets/ab32factsheet.pdf (2009).
Allison, C. E., Francey R. J., and Steele, L. P. The International Atomic Energy Agency circulation of laboratory air standards for stable isotope comparisons: aims, preparation and preliminary results. In: Isotope aided studies of atmospheric carbon dioxide and other greenhouse gases Phase II (IAEA-TEDOC-1269). IAEA, Vienna, Austria, pp 5-23 (2002).
Allison C. E., Francey R. J., White J. W. C, Vaughn B. H., Wahlen M., Bollenbacher A., Nakazawa T. What have we learnt about stable isotope measurements from the IAEA CLASSIC? In: Report of the eleventh WMO/IAEA meeting of experts on carbon dioxide concentration and related tracer measurement techniques, Tokyo, Japan, 25-28 Sep. 2001, MO/GAW Report No. 148, Geneva, pp 17-30 (2003).
Amico di Meane, E., Plassa, M., Rolle, F., Sega, M. Metrological traceability in gas analysis at I.N.Ri.M: gravimetric primary gas mixtures. Accred Qual Assur 14:607-611 (2009).
Amundson, R., Sanderman, J., and Yoo, K. Environmental and geological controls on the soil carbon cycle in a changing world (in Geological Society of America, 2008 annual meeting, Anonymous,) *Abstracts with Programs—Geological Society of America* (October, vol. 40(6):24 (2008).
ASTM D6866-08. Active Standard: D6866-08. Standard Test Methods for Determining the Biobased Content of Solid, Liquid, and Gaseous Samples Using Radiocarbon Analysis. ASTM (2008).
Barford, C., Steven C. Wofsy, Michael L. Goulden, J. William Munger, Elizabeth Hammond Pyle, Shawn P. Urbanski, Lucy Hutyra, Scott R. Saleska, David Fitzjarrald, and Kathleen Moore. *Science* 294: 1688-1691 [DOI: 10.1126/science.1062962 (2001).

Becker, J. F., Sauke, T. B., Loewenstein, M. Appl. Opt. 31: 1921 (1992).

Bonan, G. B. A land surface model (LSM version 1.0) for ecological, hydrological, and atmospheric studies: Technical description and user's guide, 150 pp., Natl. Cent. for Atmos. Res., Boulder, Colo. (1996).

Bradley, L. C., Soohoo, K. L., Freed, C. Absolute frequencies of lasing transitions in nine CO2 isotopic species. IEEE Journal of Quantum Electronics vol. QE-22, No. 2 (1986).

Broecker, W. Radiocarbon. In: Treatise on Geochemistry, Elsevier 2007.

Brown, M. A., Levine' M. D., Short, W., Koomey. J. G., Energy Policy 29(14): 1179-1196 (2001).

Canadell, J., Quere C., Raupach M., Field C., Buitenhuis E., Clais P., Conway T., Gillett N., Houghton R., Marland G. Contributions to accelerating atmospheric CO2 growth from economic activity, carbon intensity and efficiency of natural sinks PNAS early edition, 10.1073 (2007).

Capoor, K., and Ambrosi. 2007. State and Trends of The Carbon Market 2007. World Institute, Washington, D.C., 2007.

Chicago Climate Exchange 2010. http://www.chicagoclimatex.com/content.jsf?id=781.

Ciais P., and four others. A Large northern hemisphere terrestrial CO2 sink indicated by the 13C/12C ratio of atmospheric CO2. Science 269(5227): 1098-1102 (1995).

Convery F. J. and Redmond, L. Market and Price Developments in the European Union Emissions Trading Scheme. Rev Environ Econ Policy 1: 88-111 (2007).

Coplen, T. B. New manuscript guidelines for the reporting of stable hydrogen, carbon, and oxygen isotope-ratio data. Geothermics 24(5-6):707-712 (1995).

Coplen T. B. et al., and five others. New Guidelines for delta $^{13}C$ measurements. Anal. Chem. 78: 2439-2441 (2006).

Davis, W. Carbon-14 production in nuclear reactors. ORNL/NUREG/TM-12 (1977).

Dias, C. M. and 4 others. 14C content in vegetation in the vicinities of Brazilian nuclear power reactors. J. Env. Radio. 99(7): 1095-1101 (2008).

European Union Emissions Trading Scheme. www.euets.com. 2009.

Ellerman, D. A. and Joskow, P. L. The European Union's Emissions Trading System in Perspective. MIT, May 2008.

Flesch, T. K., Wilson, J. D., Harper, L. A., Crenna, B. P., Sharpe, R. R. Deducing ground-to-air emissions from observed trace gas concentrations: a field trial. J. Appl. Meteorol. 43, 487-502 (2004).

FLUXNET. http://www.fluxnet.ornl.gov/fluxnet/index.cfm.

Freed, C. Ultrastable CO2 Lasers. The Lincoln Laboratory Journal. Vol. 3(3): 479-500 (1990).

Freed C. CO2 Isotope Lasers and their applications in tunable laser spectroscopy. Chapter 4, pp. 63-165 in "Tunable Lasers Handbook" (Academic Press, 1995, F. J. Duarte, Editor).

Friedmann, S. J, Geological Carbon Dioxide Sequestration Elements vol. 3, pp 179-184, (2007).

Gitzinger C. and 3 others. Technical Report: Verifications under the terms of article 35 of the euratom treaty. Finnish National Monitoring Network for Environmental Radioactivity. FI-07/02 (2007). Global view. NOAA. http://www.esrl.noaa.gov/gmd/ccgg/globalview/(2010).

Graven, H. D. and 5 others. Vertical profiles of biospheric and fossil fuel-derived CO2 and fossil fuel CO2: CO ratios from airborne measurements of delta 14C, CO2 and CO above Colorado, USA. Tellus 61B, 536-546 (2009).

Grell, G., Dudhia, J., and Stauffer, D. A description of the fifth-generation Penn State/NCAR mesoscale model (MM5), Natl. Cent. For Atmos. Res., Boulder, Colo. (1995).

Guillian, E. H. Far field monitoring of rogue nuclear activity with an array of large anti-neutrino detectors. Earth, Moon, and Planets 99: 309-330 (2006).

Gulden, M. L., et al., and 4 others. Measurements of carbon sequestration by long-term eddy covariance: methods and a critical evaluation of accuracy. Global Change Biology 2: 169-182 (1996).

Ha-Duong, M., and Loisel R. Zero is the only acceptable leakage rate for geologically stored CO2: an editorial comment Climatic Change 93:311-317 (2009).

Hämäläinen, K M; Jungner, H; Antson, O; Räsänen, J; Tormonen, K; Roine, J. Penn State/NCAR mesoscale model (MM5), Natl. Cent. For Atmos. Res., Boulder, Measurement of Biocarbon in Flue Gases Using 14C Radiocarbon, Vol 49(2): 325-330 (2007).

Hamilton, K., Sjardin, M., Marcello, M., and Xu, G. Forging a Frontier: State of the Voluntary Carbon Markets 2008. A report by Ecosystem Marketplace & New Carbon Finance, May 2008.

Heimann, M. and Maier-Reimer, E. On the relations between the oceanic uptake of carbon dioxide and its carbon isotopes. Global Biogeochemical Cycles, 10: 89-110 (1996).

Hsueh, D. Y., and 6 others. Regional patterns of radiocarbon and fossil fuel-derived CO2 in surface air across North America. Geophys. Res. Lttrs. VOL. 34, L02816, doi: 10.1029/2006GL027032 (2007).

Humphries, S. D., A. R. Nehrir, C. J. Keith, K. S. Repasky, L. M. Dobeck, J. L. Carlsten, and L. H. Spangler, "Testing carbon sequestration site monitor instruments using a controlled carbon dioxide release facility," Appl. Opt. 47, 548-555 (2008).

Hurley, P. J., Physick, W. L., Luhar, A. K. TAPM: a practical approach to prognostic meteorological and air pollution modeling. Environ. Model. Software 20, 737-752 (2005).

Galik, S. C., Mobley, M. L., Richter, D. A virtual "field test" of forest management carbon offset protocols: in influence of accounting. Mitig. Adapt Strage Glob Change 14:677-690 (2009).

IPCC. Contribution of Working Group I to the Fourth Assessment Report of the IPCC (ISBN 978 0521 88009-1) (2007).

IPCC. Climate Change 2007 and 2008—The Physical Science Basis (2008).

Kallman, C. T. Detection technology in the $21^{st}$ century: the case of nuclear weapons of mass destruction. US Army War College, Carlisle, Pa. (2008).

Keeling, C. D. The concentration and isotopic abundances of atmospheric carbon dioxide in rural areas. Geochem. et Cosmochem. Acta 13 (322-334) (1958).

Keeling, C. D. The Suess effect: 13-Carbon-14-Carbon interrelations. Environment International Vol. 2: 229-300 (1979).

Korashi, J. and 4 others. A simple and reliable monitoring system for 3H and 14C in radioactive airborne effluent. J. Radio. Nuc. Chem. 268(3): 475-479 (2006).

Kosovic, B. Monache, L. D., Cameron-Smith, P., Bergman, D., Grant, K., Guilderson, T. Toward regional fossil fuel CO2 emissions verification using WRF-CHEM. $9^{th}$ WRF users workshop, Boulder, Colo. Jun. 26, 2008.

Lai, C. T., Schauer, A. J., Owensby, C., Ham, J. M., Helliker, B., Tans, P. P., Ehleringer, J. R. Regional CO2 fluxes inferred from mixing ratio measurements: estimates from flask air samples in central Kansas, USA. Tellus Vol. 58b, pp. 523-536 (2006).

Leuning, R., Etheridge, D., Luhar, A., Dunse, B. Atmospheric monitoring and verification technologies for $CO_2$ geosequestration. Intl J. Greenhouse Gas Controls 2: 401-414 (2008).

Levin, I., J. Schuchard, B. Kormer, K. O. Munnich. The continental European Sues effect. *Radiocarbon* 31:431-440 (1989).

Levin, I., R. Graul, N. B. A. Trivett. Long term observations of atmospheric CO2 and carbon isotopes at continental sites in Germany. *Tellus* 47B:23-34 (1995).

Levin, I., Kormer, B., Schmidt, M., Sartorius, H., A novel approach for independent budgeting of fossil fuel CO2 over Europe by 14CO2 observations. Geo. Res. Letters Vol. 30 (23), 2194 (2003).

Levin, I., Rodenbeck, C. Can the envisaged reductions of fossil fuel CO2 emissions be detected by atmospheric observations? Naturwissenschaften 95: 203-208 (2008).

Lewicki, J. L., G. E. Hilley, M. L. Fischer, L. Pan, C. M. Oldenburg, L. Dobeck, and L. Spangler, Eddy covariance observations of surface leakage during shallow subsurface CO2 releases, Journal of Geophysical Research— Atmospheres, 114, D12302 (2009).

Libby W. F., Anderson E. C., and Arnold J. R. Age determination by radiocarbon content: worldwide assay of natural radiocarbon. Science 109, 227-228 (1949).

Lloyd, J. and 12 others. Vertical profiles, boundary layers, and regional flux estimates for CO2 and its 13C/12C ratio for water vapor above a forest/bog mosaic in central Siberia. Global Biogeochemical Cycles, 15(2): 267-284 (2001).

Matsumoto, K., and 30 others. Evaluation of ocean carbon cycle models with data-based metrics. Geophys. Res. Lett. 31, L07303, doi: 10.1029/2003GL018970 (2003).

McNichol, A. P. and 3 others. The rapid preparation of seawater total CO2 for radiocarbon analysis at the national ocean sciences AMS facility. Radiocarbon 36(2): 237-246 (1994).

Midwest Greenhouse Gas Accord. www.midwesternaccord.org. 2009.

Murnick, D. E., and Peer, J. Science 263: 945-947 (1994).

Murnick, D., Dogru, O., Ilkmen E. Nuclear Instruments and Methods in Physics Research B 259 786-789 (2007).

Murnick, D. E., Dogru, O., and Ilkmen, E. Intracavity optogalvanic spectroscopy: An analytical technique for 14C analysis with subattamole sensitivity. Analytical chemistry 80(13):4820-4824 (2008).

Murnick, D. E., Dogru, O, Ilkman, E. Laser based $^{14}C$ counting, an alternative to AMS in biological studies. Nuclear Instruments and Methods in Physics Research Section B: Beam Interactions with Materials and Atoms Volume 259(1): 786-789 (2009).

Oldenburg, C. M., Lewicki, L. L., and Hepple, R. P. Near-surface monitoring strategies for geologic carbon dioxide storage verification. Earth Science Division, Ernesto Orlando LBNL, ReportLBNL-54089, pp. 1-54 (2003).

O'Leary, M. H. Carbon isotopes in photosynthesis. BioScience, 38, 328-336 (1988).

Pacala S. W. Letter Reporting on the Orbiting Carbon Observatory. Committee on Methods for Estimating Greenhouse Gas Emissions; National Research Council (2009).

Park, J. H. and 6 others. Isotopic fractionation during pretreatment for accelerator mass spectrometer measurement of (D3C)2O containing 14C produced by nuclear reaction. J. Radio. Nuc. Chem. 275(3): 627-631 (2008).

Parton, W., and 10 others. Observations and modeling of biomass and soil organic matter dynamics for the grassland biome worldwide. Glob. Biogeochem. Cycles 7:109-131 (1993).

Peters, W. and 15 others. An atmospheric perspective on North American carbon dioxide exchange: Carbon Tracker. Proc. Natl. Acad. Sci. USA, 48, 18925-18930 (2007).

Randerson J. T., and 4 others. Seasonal and latitudinal variability of troposphere delta 14CO2: Post bomb Contributions from fossil fuels, oceans, the stratosphere, and the terrestrial biosphere. Global Biogeochemical Cycles, vol 16(4): 1112 (2002).

Raupach, M., Marland G., Clais P., Quere C., Canadell J., Klepper G., Field C. Global and regional drivers of accelerating CO2 emissions. PNAS, 104(24):10288-10293 (2007).

Reddy, C. M., Demello, J. A., Carmicheal, C. A., Peacock, E. E., Xu, L. Arey, S. J. Determination of biodiesel blending percentages using natural abundance radiocarbon analysis: testing the accuracy of retail biodiesel blends. Environ. Sci. Technol. 42, pp. 2476-2484 (2008).

Regional Greenhouse Gas Initiative. www.RGGI.og. 2009.

Riley W. and 7 others. 2008: Where do fossil fuel carbon dioxide emissions from California go? An analysis based on radiocarbon observations and an atmospheric transport model. Journal Geophysical Research. VOL. 113, G04002, doi:10.1029/2007JG000625 (2007).

Roussel-Debet, S, and 4 others. Distribution of carbon 14 in the terrestrial environment close to French nuclear power plants. J. Env. Radioactivity 87(3): 246-259 (2006).

Rozanski, K. 1991. International Atomic Energy Agency Consultants' Group Meeting on C-14 Reference Materials for Radiocarbon Laboratories, Feb. 18-20, 1991. Report by K. Rozanski, Section of Isotope Hydrology, IAEA, Vienna (1991).

Saleska, S. R., Shorter, J. H., Herndon, S., Jimenez, R., McMannus, J. B., Munger, J. W., Nelson, D. D., Zahniser, M. S. What are the instrumentation requirements for measuring the isotopic composition of net ecosystem exchange of CO2 using eddy covariance methods? Isotopes in Env. Health Studies Vol. 42(2), pp. 115-133 (2006).

Salon, D., Sperling D., Meier, A., Murphy, S., Gorham, G., Barrett, J. City carbon budgets: Aligning incentives for climate-friendly communities. Institute of Transportation Studies, University of California, Davis, Research Report UCD-ITS-RR-08-17 (2008).

Schlesinger, W. H. Carbon sequestration in soils: some cautions amidst optimism. Agriculture, Ecosystems and Environment Vol. 82: (1-3) 121-127 (2000).

Scott, N. A., and 6 others. Changes in carbon storage and net carbon exchange one year after an initial shelterwood harvest at Howland Forest, Me. Environmental management 33(1): S9-S22 (2004).

Scott, M. E. et al., and 11 others. Future needs and requirements for AMS 14C standards and reference materials. Nuclear Instruments and Methods in Physics Research B 223-224: 382-387 (2004).

Staber, S., Flamme S., Fellner J., Methods for determining the biomass content of waste. Waste Management and Research 26: 78-87 (2008).

Steffen W., et al. The Terrestrial Carbon Cycle: Implications for the Kyoto Protocol. Science 280: 1393-1394 (1998).

Stork, A., Witte, R., and Fuhr, F. 14CO2 measurement in air: literature review and a new sensitive method. Env. Sci. and Technology 31(4) 1997.

Stuiver, M., and Polach, H. A. Discussion: Reporting of 14C data. Radiocarbon 19(3):355-363 (1977).

Tans, P. P., P. S. Bakwin, and D. W. Guenther. A feasible global carbon cycle observing system: a plan to decipher today's carbon cycle based on observations. Global Change Biology 2:309-318 (1996).

Turnbull J. C., and 5 others. Comparison of 14CO2, CO and SF6 as tracers for recently added fossil fuel CO2 in the atmosphere and implications for biological CO2 exchange. Geophysical Research Letters, vol 33, L01817 (2006).

Turnbull, J. C. et al., A new High resolution 14CO2 time series for North American continental air. J. Geophysical Research Res. 112, D1130 (2007).

Tuniz, C. Accelerator Mass Spectrometry. Radiation Physics and Chemistry vol. 61(3-6): 317-322 (2001).

Tuzson, B. and 5 others. QCLAS. A compact isotopologue specific analyzer for atmospheric CO2. Geophysical Res. Abstracts 10 (EGU2008-A-07132 (2008).

Uchida, M., and 9 others. Ecosystem-scale carbon isotope ratios of respired CO2 in cool-temperate deciduous forests under Asian monsoon climate. Journal of Geophysical Research vol. 113. G02015 (2008).

UNFCCC: http://unfccc.int/methods_science/redd/items/4531.php (2008).

Updegraff, K., Zimerman, P. R., Price, M., Capehart, W. J. C-Lock: An online system to standardize the estimation of agricultural carbon sequestration credits. Fuel Processing Technology 86:1695-1704 (2005).

Urbanski, S, and 8 others. Factors controlling CO2 exchange on timescales from hourly to decadal at Harvard Forest. J. Geophys. Res. 112, G02020, doi:10.1029/2006JG000293 (2007).

US Climate Change Science Program 2007. Synthesis and Assessment Product 2.2: The First State of the Carbon Cycle Report (2007).

Venteris, E. R. and 8 others. A new digital geologic model for carbon sequestration planning in the Appalachian and Michigan basins. Geological Society of America, Abstracts with programs, Vol. 38(4): 14 (2006).

West, T. O., and Marland, G. Net carbon flux from agricultural ecosystems: methodology for full carbon cycle analyses. Environ. Pollut. 116(3): 439-44 (2002).

Western Climate Initiative. www.westernclimateinitiative.org. 2009.

Werner, A, Brand, W. Referencing strategies and techniques in stable isotope ratio analysis. Rapid Communications in Mass Spectrometry 15: 501-519 (2001).

Widory, D. Combustibles, fuels and their combustion products: a view through carbon isotopes. Combustion Theory and Modelling Vol 10 (5) pp. 831-841 (2006).

World Meteorological Organization. Global Atmosphere Watch Report, ed. Miller, J. B. (World Meteorological Organization, Geneva), no. 168 (2007).

Yim, M, and Caron, F. Life cycle and management of carbon 14 from nuclear power generation. Progress in Nuclear Energy 48: 2-36 (2006).

Zobitz, J. M., and 5 others. Integration of process-based soil respiration models with whole ecosystem CO2 measurements. Ecosystems 11:629-642 (2008).

Zoe, L., and 6 others. Testing Lagrangian atmospheric dispersion modelling to monitor $CO_2$ and $CH_4$ leakage from geosequestration. Atmospheric Environment 43: 2602-2611 (2009).

Zoe Loh, Ray Leuning, Steve Zegelin, David Etheridge, Mei Bai, Travis Naylor, David Griffith, Masarie, K. A., Langenfelds, R. L., Allison, C. E., Conway, T. J., Dlugokemcky, E. J., Francey, R. J., Novelli, P. C., Steele, L. P., Tans, P. P., Vaughn, B., White, J. W. C. NOAA/CSIRO flask air intercomparison experiment: a strategy for directly assessing consistency among atmospheric measurements made by independent laboratories. J. Geo. Res. Vol. 186 (D17), pp., 20445-20464 (2001).

Zwaan B., and Gerlagh R. Effectiveness of CCS with time-dependent CO2 leakage. Energy Procedia 1: 4977-4984 (2009).

It will be understood that other embodiments could be created with variations in function, method and implementation, and various modifications can be made without departing from the invention. Accordingly, the scope of the invention should be determined by the appended claims and not limited to the above-described illustrative embodiments.

The invention claimed is:

1. A system of systems for creating tradable products that separately quantify biogenic and fossil carbon, comprising:

(a) a carbon data collection system for collecting carbon flux data comprising an array of analyzers placed in predetermined representative geographic locations, wherein each analyzer comprises a $^{12}C$ laser device, a $^{13}C$ laser device, a $^{14}C$ laser device, and a sample chamber to measure the individual amounts of $^{12}C$, $^{13}C$, and $^{14}C$ isotopes contained in one or more samples, a modulator to modulate the $^{14}C$ laser device, and a timer to allow measurements of $^{12}C$, $^{13}C$, and $^{14}C$ isotopes at a sampling frequency of at least once an hour over a predetermined time period; and a standard reference gas module for obtaining a standard reference baseline and calibrating the measured amounts of the $^{12}C$, $^{13}C$, and $^{14}C$ isotopes from each of said analyzers based on said standard reference baseline;

(b) a global reference system including a $^{12}C$ laser device, a $^{13}C$ laser device, a $^{14}C$ laser device, and a global reference sample cell to measure the individual amounts of $^{12}C$, $^{13}C$, and $^{14}C$ isotopes contained in a global reference sample;

(c) a calibration system for standardizing the measured amount of $^{12}C$, $^{13}C$, and $^{14}C$ isotopes from the analyzers of said carbon data collection system based on said measured amounts of $^{12}C$, $^{13}C$, and $^{14}C$ isotopes contained in the global reference sample to obtain standardized amounts of $^{12}C$, $^{13}C$, and $^{14}C$ isotopes; and (d) a data processing system for receiving and converting one or more of the measured amounts of $^{12}C$, $^{13}C$, and $^{14}C$ isotopes from each of said analyzers, the standard reference baseline, the standardized amounts of $^{12}C$, $^{13}C$, and $^{14}C$ isotopes and the calibrated measured amounts of the $^{12}C$, $^{13}C$, and $^{14}C$ isotopes to tradable products that separately quantify biogenic and fossil carbon.

2. The system of systems of claim 1, wherein said carbon data collection system further comprises a telemetry device for sending measured amounts of $^{12}C$, $^{13}C$, and $^{14}C$ isotopes from each of said analyzers, the standard reference baseline, and the calibrated measurement amounts of $^{12}C$, $^{13}C$, and $^{14}C$ isotopes to said data processing system.

3. The system of systems of claim 1, wherein said predetermined representative geographic locations comprise surface and sub-surface locations for storage of greenhouse gases and wherein said sampling frequency is at least 1 Hz.

4. The system of systems of claim 1,
wherein said predetermined representative geographic locations comprise above-ground and sub-surface locations in an agricultural area and
wherein said sampling frequency is at least 1 Hz.

5. The system of systems of claim 1,
wherein said predetermined representative geographic locations comprise one or more locations associated with a body of water and
wherein each analyzer further comprises a gas stripping device capable of stripping dissolved gases from the body of water.

6. The system of systems of claim 5, wherein said array of analyzers comprises more than 100 analyzers.

7. The system of systems of claim 1,
wherein said predetermined representative geographic locations comprise locations near a nuclear power plant and
wherein said sampling frequency is at least 1 Hz.

8. The system of systems of claim 1, wherein each analyzer comprises a standard reference gas module.

9. The system of systems of claim 1, wherein said global reference system is located in a satellite.

10. The system of systems of claim 1, wherein said array of analyzers comprises more than 25 analyzers.

11. The system of systems of claim 1,
wherein said predetermined representative geographic locations comprise one or more locations exposed to flue gases and
wherein said sampling frequency is at least 1,440 times a day.

12. The system of systems claim 1, wherein said timer allows measurements of $^{12}C$, $^{13}C$, and $^{14}C$ isotopes at a sampling frequency of up to 100 Hz.

13. The system of systems of claim 1, wherein said data processing system comprises one or more conversion systems parameterized for biogenic and fossil fuel carbon to convert the one or more of the measured amounts of $^{12}C$, $^{13}C$, and $^{14}C$ isotopes from each of said analyzers, the standardized amounts of $^{12}C$, $^{13}C$, and $^{14}C$ isotopes, the standard reference baseline, and the calibrated measured amounts of the $^{12}C$, $^{13}C$, and $^{14}C$ isotopes in the data processing system to tradable products that separately quantify biogenic and fossil carbon.

14. A method for generating tradable products that separately quantify biogenic and fossil carbon flux comprising:
(a) placing an array of analyzers at predetermined representative geographic locations, wherein each analyzer comprises a $^{12}C$ laser device, a $^{13}C$ laser device, a $^{14}C$ laser device, a modulator to modulate the $^{14}C$ laser device, and a sample chamber;
(b) collecting one or more samples in the sample chambers of the analyzers;
(c) measuring the individual amounts of $^{12}C$, $^{13}C$, and $^{14}C$ isotopes contained in the samples at a sampling frequency of at least once an hour over a predetermined time period;
(d) obtaining a standard reference baseline with a standard reference gas module;
(e) calibrating the measured amounts of $^{12}C$, $^{13}C$, and $^{14}C$ isotopes from each of the analyzers based on the standard reference baseline;
(f) standardizing the measured amounts of $^{12}C$, $^{13}C$, and $^{14}C$ isotopes in the at least one forest samples based on measured amounts of $^{12}C$, $^{13}C$, and $^{14}C$ isotopes in a global reference sample;
(g) sending one or more of the measured amounts of $^{12}C$, $^{13}C$, and $^{14}C$ isotopes from each of said analyzers, the standard reference baseline, the calibrated measured amounts of the $^{12}C$, $^{13}C$, and $^{14}C$ isotopes and the standardized amounts of $^{12}C$, $^{13}C$, and $^{14}C$ isotopes to a data processing system;
(h) converting said one or more of the measured amounts of $^{12}C$, $^{13}C$, and $^{14}C$ isotopes from each of said analyzers, the standard reference baseline, the calibrated measured amounts of the $^{12}C$, $^{13}C$, and $^{14}C$ isotopes and the standardized amounts of $^{12}C$, $^{13}C$, and $^{14}C$ isotopes in the data processing system to tradable products that separately quantify biogenic and fossil carbon flux.

15. The method of claim 14,
wherein said predetermined representative geographic locations comprise surface and sub-surface locations for storage of greenhouse gases and
wherein said sampling frequency is at least 1 Hz.

16. The method of claim 14,
wherein said predetermined geographic representative locations comprise above-ground and sub-surface locations in an agricultural area and
wherein said sampling frequency is at least 1 Hz.

17. The method of claim 14,
wherein said predetermined representative geographic locations comprise one or more locations associated with a body of water and
wherein each analyzer further comprises a gas stripping device capable of stripping dissolved gases from the body of water.

18. The method of claim 14,
wherein said predetermined representative geographic locations comprise one or more locations exposed to flue gases and
wherein said sampling frequency is at least 1,440 times a day.

19. The method of claim 14,
wherein said predetermined representative geographic locations comprise geographic locations near a nuclear power plant and
wherein said sampling frequency is at least 1 Hz.

20. The method of claim 14, wherein each analyzer comprises a standard reference gas module.

21. The method of claim 14, wherein said global reference system is located in a satellite.

22. The method of claim 14, wherein said array of analyzers comprises more than 25 analyzers.

23. The method of claim 14, wherein said array of analyzers comprises more than 100 analyzers.

24. The method of claim 14, wherein said measuring the individual amounts of is carried out at a sampling frequency of up to 100 Hz.

25. The method of claim 14, wherein said converting is carried out using one or more conversion systems parameterized for biogenic and fossil carbon to convert the one or more of the measured amounts of $^{12}C$, $^{13}C$, and $^{14}C$ isotopes from each of said analyzers, the standardized amounts of $^{12}C$, $^{13}C$, and $^{14}C$ isotopes, the standard reference baseline, and the calibrated measured amounts of the $^{12}C$, $^{13}C$, and $^{14}C$ isotopes to tradable products that separately quantify biogenic and fossil carbon.

* * * * *